(12) United States Patent
Ma et al.

(10) Patent No.: US 11,912,894 B2
(45) Date of Patent: Feb. 27, 2024

(54) ANTIMICROBIAL AND ANTIFOULING CONFORMAL HYDROGEL COATINGS

(71) Applicant: CORNELL UNIVERSITY, Ithaca, NY (US)

(72) Inventors: Minglin Ma, Ithaca, NY (US); You Yong, Ithaca, NY (US); Mingyu Qiao, Ithaca, NY (US); Qingsheng Liu, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 413 days.

(21) Appl. No.: 16/696,469

(22) Filed: Nov. 26, 2019

(65) Prior Publication Data

US 2020/0172741 A1 Jun. 4, 2020

Related U.S. Application Data

(60) Provisional application No. 62/771,246, filed on Nov. 26, 2018.

(51) Int. Cl.
| | | |
|---|---|---|
| A61L 31/14 | (2006.01) | |
| A61L 15/46 | (2006.01) | |
| A61L 29/14 | (2006.01) | |
| A61L 17/00 | (2006.01) | |
| A61L 31/10 | (2006.01) | |
| A61L 29/08 | (2006.01) | |
| A61L 15/60 | (2006.01) | |
| A61L 29/16 | (2006.01) | |
| A61L 17/14 | (2006.01) | |
| A61L 31/16 | (2006.01) | |
| C09D 5/16 | (2006.01) | |
| B05D 3/10 | (2006.01) | |
| B05D 3/06 | (2006.01) | |

(52) U.S. Cl.
CPC ............ C09D 5/1625 (2013.01); A61L 15/60 (2013.01); A61L 17/005 (2013.01); A61L 29/085 (2013.01); A61L 29/145 (2013.01); A61L 29/16 (2013.01); B05D 3/067 (2013.01); B05D 3/101 (2013.01); B05D 3/108 (2013.01); C09D 5/1662 (2013.01); C09D 5/1687 (2013.01); B05D 2201/02 (2013.01); B05D 2320/00 (2013.01)

(58) Field of Classification Search
CPC .. C09D 5/1625; C09D 5/1662; C09D 5/1687; A61L 15/60; A61L 17/005; A61L 29/085; A61L 29/145; A61L 29/16; B05D 3/067; B05D 3/101; B05D 3/108; B05D 2201/02; B05D 2320/00
See application file for complete search history.

(56) References Cited

U.S. PATENT DOCUMENTS

| | | | |
|---|---|---|---|
| 6,469,177 B1 * | 10/2002 | Worley | |
| 8,110,242 B2 | 2/2012 | Hawkins et al. | |
| 8,835,671 B2 | 9/2014 | Jiang et al. | |
| 2013/0190672 A1 | 7/2013 | Liu | |
| 2017/0355799 A1 * | 12/2017 | Veiseh | |
| 2019/0070826 A1 | 3/2019 | Zhao et al. | |
| 2019/0125934 A1 | 5/2019 | Zhao et al. | |

FOREIGN PATENT DOCUMENTS

| | | | |
|---|---|---|---|
| JP | 2008178654 A | * | 8/2008 |
| WO | 2015/042717 A1 | | 4/2015 |
| WO | 2019/246123 A1 | | 12/2019 |

OTHER PUBLICATIONS

Demir et al., "N-Halamine Biocidal Materials with Superior Antimicrobial Efficacies for Wound Dressings." Molecules 22(10):1582 (2017).
Gao et al., "Construction of Antibacterial N-Halamine Polymer Nanomaterials Capable of Bacterial Membrane Disruption for Efficient Anti-Infective Wound Therapy," Macromol. Biosci. 19(4):1800453 (2019).
Ma et al., "Novel ZnO/N-Halamine-Mediated Multifunctional Dressings as Quick Antibacterial Agent for Biomedical Applications," ACS Appl. Mater. Interfaces 11(34):31411-31420 (2019).
Huang et al., "Non-Sticky and Antimicrobial Zwitterionic Nanocomposite Dressings for Infected Chronic Wounds," Biomater. Sci. 5(6):1072-1081 (2017).
Lin et al., "Self-Healing Zwitterionic Sulfobetaine Nanocomposite Hydrogels with Good Mechanical Properties," RSC Adv. 9:31806-31811 (2019).
Zhu et al., "One-Step Synthesis of an Antibacterial and Pro-Healing Wound Dressing That Can Treat Wound Infections," J. Mater. Chem. B 5:8451-8458 (2017).
Zhu et al., "Zwitterionic Hydrogels Promote Skin Wound Healing," J. Mater. Chem. B 4:5105-5111 (2016).
Wu et al., "Sulfated Zwitterionic Poly(Sulfobetaine Methacrylate) Hydrogels Promote Complete Skin Regeneration," Acta Biomater. 71:293-305 (2018).

(Continued)

Primary Examiner — Alma Pipic
(74) Attorney, Agent, or Firm — Troutman Pepper Hamilton Sanders LLP (Rochester)

(57) ABSTRACT

The present application discloses a method of forming a hydrogel-coated substrate, wherein the hydrogel has antifouling and antimicrobial properties. The method comprises applying an aqueous pre-hydrogel solution to a substrate, polymerizing the aqueous pre-hydrogel solution, thereby forming a coated substrate having a conformal hydrogel coating and a non-conformal hydrogel coating, contacting the coated substrate with a swelling agent, and removing the non-conformal hydrogel coating from the coated substrate, thereby leaving the conformal hydrogel coating on the substrate to form the hydrogel-coated substrate. The aqueous pre-hydrogel solution comprises a monomer with antimicrobial activity, a monomer with antifouling activity, and either a polymer, oligomer, or macromer which, when polymerized together, form a hydrogel. Also disclosed is a coated substrate and a hydrogel coating.

14 Claims, 54 Drawing Sheets

(56) References Cited

OTHER PUBLICATIONS

Guvendiren et al., "Swelling-Induced Surface Patterns in Hydrogels with Gradient Crosslinking Density," Advanced Functional Materials 19:3038-3045 (2009).
Son et al., "Hydro-Nanofibrous Mesh Deep Cell Penetration: A Strategy Based on Peeling of Electrospun Coaxial Nanofibers" Nanoscale 13:6051-6059 (2018).
Yong et al., "Conformal Hydrogel Coatings on Catheters To Reduce Biofouling," Langmuir 35(5):1927-1934 (2018).
Hui et al., "Antimicrobial N-Halamine Polymers and Coatings: A Review of Their Synthesis, Characterization, and Applications," Biomacromolecules 14(3):585-601 (2013).
Chen and Sun, "N-Halamine-Based Antimicrobial Additives for Polymers: Preparation, Characterization and Antimicrobial Activity," Ind. Eng. Chem. Res. 45(8):2634-2640 (2006).
Singha et al., "A Review of the Recent Advances in Antimicrobial Coatings for Urinary Catheters," Acta Biomater. 50:20-40 (2017).
Dong et al., "Chemical Insights into Antibacterial N-Halamines," Chemical Review 117:4806-4962 (2017).
Parada et al., "Impermeable Robust Hydrogels via Hybrid Lamination," Adv. Healthcare Mater., 6:1700520 (2017).
Yu et al., "Multifunctional "Hydrogel Skins" on Divers Polymers with Arbitrary Shapes," Advanced Materials, 31: 1807101 (2018).

\* cited by examiner

ANTIMICROBIAL AND ANTIFOULING CONFORMAL HYDROGEL COATINGS

This application claims benefit of U.S. Provisional Application Ser. No. 62/771,246, filed Nov. 26, 2018, which is incorporated herein by reference in its entirety.

This invention was made with government support under Contract 2017-18-107 awarded by the National Institute of Food and Agriculture, U.S. Department of Agriculture. The government has certain rights in the invention.

FIELD

The present application relates to antimicrobial and antifouling conformal hydrogel coatings.

BACKGROUND

Medical devices, such as catheters, are used extensively in the medical and veterinary fields. In the U.S., for example, more than 30 million urinary catheters are inserted annually to drain urine from patients' urinary bladders. There is a very high chance, about 12-25%, that an inserted catheter will cause a urinary tract infection. Such an infection is even observed with catheters made of materials that are said to resist bacterial adhesion, including silicone, polyurethane, and the like. A conditioning film can be formed quickly on these catheters by organic molecules and electrolytes in urine on the surface of the catheter after insertion, followed by a microbial colonization.

To combat this problem, significant efforts have been made to coat catheters with hydrophilic, antifouling, or antibacterial functional polymers. While antifouling and biocidal polymer coatings may be effective in reducing microorganism adhesion, these thin coatings, typically between 10 and 100 nm thick, may not possess the appropriate mechanical stability for long-term use in dynamic environments in vivo.

Similarly, wound dressings are widely used to treat traumatic, thermal, acute, and chronic wounds affecting millions of people globally. Wound healing requires different tissues and cells to cooperate and communicate effectively to promote cell proliferation and tissue remodeling. Wound dressings should protect wounds from infection, have high adsorption ability, promote cell proliferation, enhance anti-inflammation, maintain desirable humidity levels, and be easily removed without pain. Conventional wound dressings fall short of these requirements.

Hydrogels, which are known to have promising biocompatibility, functional groups, density, and lubricity, have also been tested in the coating of medical devices. However, hydrogel coatings are often fragile, primarily due to the weak interaction between the hydrogel and its substrate. Forming a stable, thin, conformal (i.e., relatively uniform in structure) hydrogel coating can be challenging for several reasons, particularly when the substrate is highly curved. First, the curvature of the substrate can lead to de-wetting of the pre-hydrogel solution, making conformal coating difficult. Second, oxygen from the environment can inhibit free radical cross-linking, especially when the coating is thin, necessitating an oxygen-free environment in which to coat the substrate.

Hydrogels may also be appropriate for wound dressing materials because of their relatively high water content, desirable mechanical properties, and other features that allow them to mimic soft tissues. However, conventional hydrogels may be subject to bacterial contamination and infection.

Therefore, there exists a need for conformal hydrogel coatings having antimicrobial and antifouling properties while maintaining appropriate lubricity. In addition, there exists a need for such hydrogel coatings to be formed in open air, without the need for a low-oxygen environment. Furthermore, there exists a need for wound dressings that protect wounds from infection, have high adsorption ability, promote cell proliferation, enhance anti-inflammation, maintain desirable humidity levels, and be easily removed without pain.

SUMMARY

One embodiment of the present application relates to a method of forming a hydrogel-coated substrate, wherein the hydrogel has both antifouling properties and antimicrobial properties. This method comprises applying an aqueous pre-hydrogel solution to a substrate. The aqueous pre-hydrogel solution comprises a mixture of a monomer with antimicrobial activity, a monomer with antifouling activity, and either a polymer, oligomer, or macromer which, when polymerized together, are able to form a hydrogel. The method further comprises polymerizing the aqueous pre-hydrogel solution, thereby forming a coated substrate having a conformal hydrogel coating and a non-conformal hydrogel coating. The coated substrate is contacted with a swelling agent, and the non-conformal hydrogel coating is removed from the coated substrate, thereby leaving the conformal hydrogel coating on the substrate to form the hydrogel-coated substrate.

A further embodiment relates to a coated substrate including a substrate and a conformal hydrogel coating on the substrate. The conformal hydrogel coating comprises an antimicrobial agent, a zwitterionic antifouling agent, and either a backbone polymer, oligomer, or macromer, wherein the antimicrobial agent, the zwitterionic antifouling agent, and either the backbone polymer, oligomer, or macromer are polymerized together.

A further embodiment of the present application is directed to a hydrogel coating that may comprise a N-halamine antimicrobial agent, a zwitterionic antifouling agent, and either a backbone polymer, oligomer, or macromer, wherein the antimicrobial agent, the zwitterionic antifouling agent, and either the backbone polymer, oligomer, or macromer are polymerized together.

There exists a need for conformal hydrogel coatings having antimicrobial and antifouling properties while maintaining appropriate lubricity. In addition, there exists a need for such hydrogel coatings to be formed in open air, without the need for a low-oxygen environment.

Methods of forming a hydrogel-coated substrate, wherein the hydrogel has both antifouling properties and antimicrobial properties are disclosed here. Substrates having hydrogel coatings formed by such methods are also disclosed here, along with hydrogel coatings including polymerized N-halamine antimicrobial agents and polymerized zwitterionic antifouling agents. Substrates coated with such hydrogel coatings are also disclosed here.

The methods described generally involve a multistep process that includes shape-forming, cross-linking, and swell-peeling. In some methods described here, the cross-linking is performed in open air to allow gradual oxygen inhibition of free radicals, and to generate a gradient of crosslinking density across the hydrogel coating. Such methods may allow for the incorporation of different polymerizable monomers to obtain multifunctionality. In particular, monomers having antimicrobial and antifouling properties were polymerized.

Previously, antimicrobial functionality of hydrogels was focused on incorporating "leaching" antimicrobial compounds (e.g. metal ions, antibiotics, organic molecules, peptides) into the hydrogels. This "leaching" nature can cause toxicity problems for intimate human contact or implanted devices. Additionally, the FDA regulates these hydrogels as a "drug+device". Therefore, only a few options are available (e.g. silver) for approved applications. Although some efforts have been made to immobilize the leaching agents into the hydrogel network, they are not practical or scalable for immediate commercialization. With N-halamine chemistry, it is possible to incorporate the antimicorbial functional group into the cross-linked polymer backbone/network. The N-halamine will be activated through treatment with a chlorine solution, which is also cheap and can provide potent, broad-spectrum and non-resistance antimicrobial function. Additionally, by using N-halamine polymerized into the hydrogel of the present application, the antimicrobial functional moieties are non-leaching. From an FDA regulation point-of-view, it would be a device only (not a drug+device), which will create advantages over existing antimicrobial hydrogel system.

Furthermore, a synergistic effect is accomplished by incorporating both N-halamine and Zwitterion chemistry into the hydrogel of the present application, having both anti-fouling/anti-inflammatory and antimicrobial properties. This provide significant improvements for applications that requires both functions (e.g. urinary catheter or wound dressings). The coating method of the present application allows for the coating of the hydrogel on curved device surfaces (e.g. catheter) in a simple, low-cost and scalable way for mass and automated industry production. This is unlike previous methods that start with only monomers and face the difficulty of fixing the pre-gel solution onto device surfaces without surface treatment and also require long cross-linking times.

A simple hydrogel coating method is described here, which can overcome above-mentioned challenges by achieving tough, thin (~30 μm), and conformal hydrogel coatings on high curvature surfaces like catheters. The method can involve three steps: shape-forming, gradient cross-linking, and swell-peeling (referred as SGS hereafter). First, the high viscosity and fast thermal gelation of an agar solution was used to form a hydrogel layer coating conformal to the catheter at room temperature before de-wetting occurred. Second, to toughen the hydrogel and promote surface binding acrylamide was mixed with agar and the catheter was pre-treated with benzophenone. The crosslinking was performed in open air to purposely allow gradual oxygen inhibition of free radicals, and to generate a gradient of crosslinking density across the hydrogel layer. Third, the coated catheter was immersed in DI water to allow non-crosslinked or loosely crosslinked hydrogel to swell and fall off, leaving only a thin conformal layer of strongly bonded tough hydrogel. The final hydrogel layer, containing ~70% water, remained attached on the catheter (or medical grade silicone tubing) after stretching the catheter to at least three times its original length or after repeated rubbing using tweezers or sandpaper. The hydrogel coating also led to a 10-fold reduction of the surface coefficient of friction. Incorporating a polymerizable zwitterionic sulfobetaine monomer in the hydrogel coating significantly reduced protein adsorption in vitro and fibrotic reaction after subcutaneous implantation in C57BL/6 mice. Furthermore, incorporation of an N-halamine monomer in the coating lead to a six-log-inactivation of *E. coli* O157:H7 and *S. aureus* within 30 minutes of contact, and an over-10-fold-reduction of *E. coli* O157:H7 adhesion in a three-day bacterial adhesion experiment, as compared to uncoated catheters. The simplicity of the SGS coating method and the possibility of incorporating different functional monomers may contribute to the development of next generation catheters and other medical devices.

BRIEF DESCRIPTION OF THE DRAWINGS

FIG. 1A is a schematic representation of the method of forming the hydrogel coating of the present application. FIG. 1B shows a hydrogel coating outside and inside a length of silicone tubing. FIG. 1C shows a hydrogel coated on a 16-inch-long catheter. FIG. 1D shows a hydrogel coating over an inflated balloon catheter. FIG. 1E shows a microscopic image of a hydrogel coating on a catheter. FIG. 1F shows 10-inch-long medical grade silicone tubing coated with a hydrogel.

FIG. 2A is a schematic representation of gradient cross-linking within a hydrogel coating (DN: double-network). FIG. 2B is a graphical representation of the distribution of oxygen and radicals in a hydrogel during cross-linking. FIG. 2C is a graphical representation of the change of radical concentration distribution over time during cross-linking.

FIG. 2D is a schematic representation of radicals in weakly cross-linked hydrogel around a substrate.

FIG. 3A shows FT-IR spectra of various substrate-coating combinations of the present application. FIG. 3B shows the coefficients of friction of the substrate-coating combinations of FIG. 3A. FIG. 3C shows a stretched segment of a hydrogel-coated substrate. FIG. 3D shows the exposure of a hydrogel-coated substrate to friction using sandpaper.

FIG. 4A shows fluorescence images for uncoated and coated silicone tubing samples. FIG. 4B shows normalized fluorescence for the samples of FIG. 4A.

FIG. 4C shows stained slides of retrieved uncoated and coated silicone tubing samples after one month of subcutaneous implantation in vivo. FIG. 4D shows inflammatory cell counts at the tissue-tubing interface for retrieved uncoated and coated silicone tubing samples after one month of subcutaneous implantation in vivo. FIG. 4E shows fibrosis layer thicknesses for retrieved uncoated and coated silicone tubing samples after one month of subcutaneous implantation in vivo.

FIG. 11A is an image of a bent hydrogel-coated tube. FIG. 11B is an image of a knotted hydrogel-coated tube.

FIG. 13A shows a microscopic image of a hydrogel coating on a catheter. FIG. 13B shows a microscopic image of the hydrogel coating of FIG. 13A after being subjected to friction via sandpaper 50 times.

FIG. 18A shows uniaxial tensile testing properties of hydrogels with a 0.5% cross-linker concentration. FIG. 18B shows uniaxial tensile testing properties of hydrogels with a 1.5% cross-linker concentration. FIG. 18C shows uniaxial tensile testing properties of hydrogels with a 5% cross-linker concentration. FIG. 18D shows elastic moduli extracted from the stress-strain curves of FIG. 18A, FIG. 18B, and FIG. 18C.

FIG. 20A shows a fluorescence image of protein adhesion to a halamine-zwitterion conformal hydrogel. FIG. 20B shows a fluorescence image of protein adhesion to a commercially available wound dressing.

FIG. 20C shows a fluorescence image of protein adhesion to a second commercially available wound dressing. FIG. 20D shows the intensity of the fluorescence images of FIG. 20A, FIG. 20B, and FIG. 20C.

FIG. 21A shows vials of wound pathogen strains collected from patients' bodily fluids. FIG. 21B shows a representative in vitro sample of the wound pathogens of FIG. 21A after 30 minutes of contact time.

DETAILED DESCRIPTION

Figure 1A:
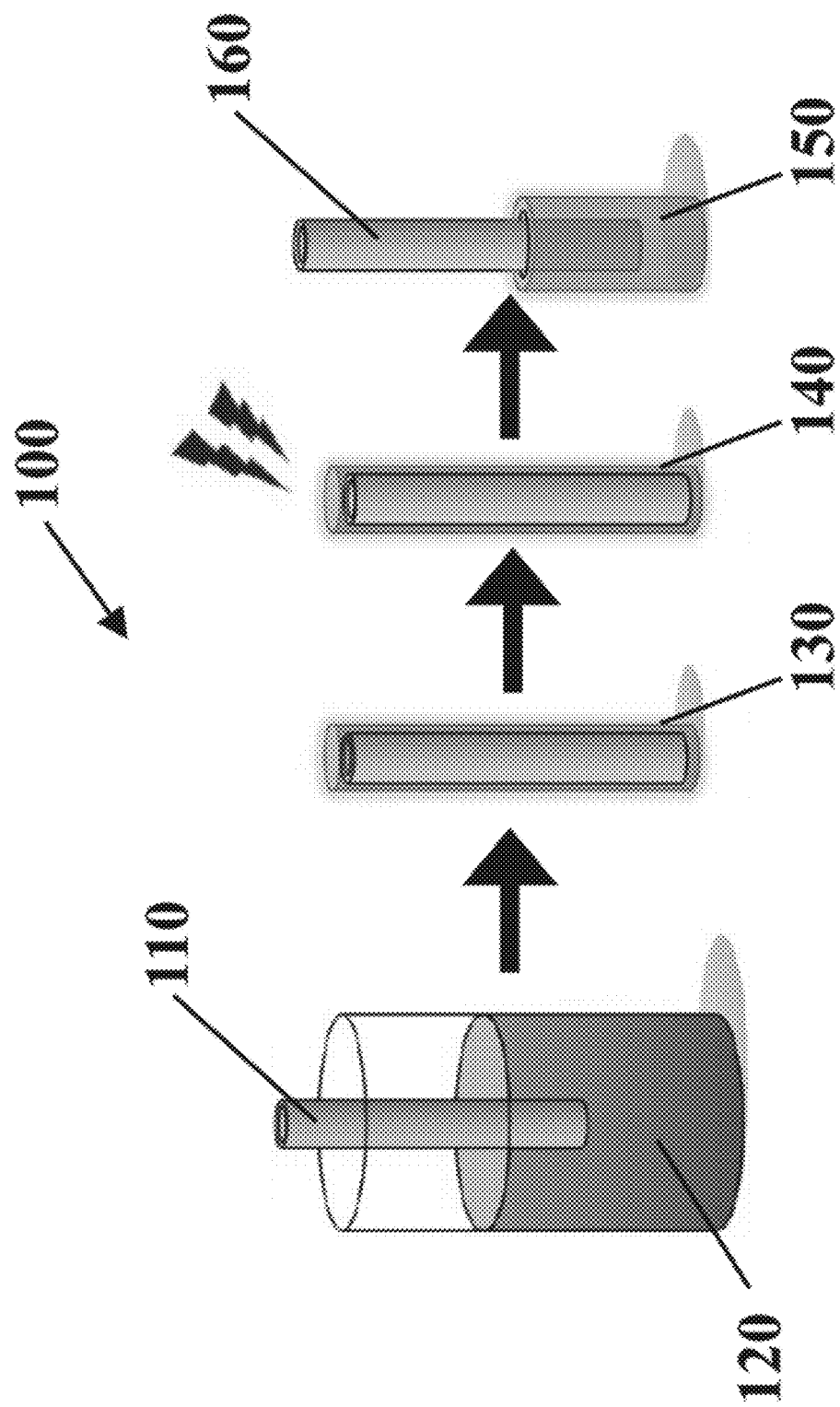
FIGS. 1A-1F are visual representations of the hydrogel coating of the present application and its method of formation.

This application is not limited to the particular systems, devices and methods described, as these may vary. The terminology used in the description is for the purpose of describing the particular versions or embodiments only, and is not intended to limit the scope of the disclosure.

One embodiment of the present application relates to a method of forming a hydrogel-coated substrate, wherein the hydrogel has both antifouling properties and antimicrobial properties. This method comprises applying an aqueous pre-hydrogel solution to a substrate. The aqueous pre-hydrogel solution comprises a mixture of a monomer with antimicrobial activity, a monomer with antifouling activity, and either a polymer, oligomer, or macromer which, when polymerized together, are able to form a hydrogel. The method further comprises polymerizing the aqueous pre-hydrogel solution, thereby forming a coated substrate having a conformal hydrogel coating and a non-conformal hydrogel coating. The coated substrate is contacted with a swelling agent, and the non-conformal hydrogel coating is removed from the coated substrate, thereby leaving the conformal hydrogel coating on the substrate to form the hydrogel-coated substrate.

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term here, those in this section prevail unless stated otherwise.

As used herein, the term "hydrogel" is given its ordinary meaning in the art and refers to a material comprising a polymer network that is able to trap and contain water. The hydrogel may include polymer chains that are crosslinked, either directly or via a crosslinking agent. In certain embodiments, the hydrogel can form a physically-crosslinked network. In certain embodiments, the hydrogel can form a chemically-crosslinked network. The degree of crosslinking may be varied, in some cases, to tailor the extent to which the gel absorbs or retains fluids. In certain embodiments, the hydrogel can be an elastic synthetic hydrogel. Examples of polymers capable of forming hydrogels include but not limited to, collagen, silicon-containing polymers, polyacrylamides, crosslinked polymers (e.g., polyethylene oxide, polyAMPS and polyvinylpyrrolidone), polyvinyl alcohol, acrylate polymers (e.g., sodium polyacrylate), and copolymers with an abundance of hydrophilic groups.

As used herein, the term "de-wetting surface" refers to a surface of a device that would resist water contact and cause difficulties in hydrogel coating. An example of de-wetting surface is the surface of a silicone urinary catheter. The respective surfaces of the other medical devices such as vascular catheters, bandages, gauzes, sutures, implantable insulin pumps, stents, and other types of implantable devices As used herein, the term "swell peeling" refers to non-crosslinked or loosely crosslinked hydrogel to swell and fall off, leaving only a thin conformal layer of strongly bonded tough hydrogel. This is due to different swell ratios along the hydrogel caused by gradient cross-linking.

The term "alkyl" means an aliphatic hydrocarbon group which may be straight or branched. When not otherwise restricted, the term refers to an alkyl of 20 or fewer carbons. Branched means that one or more lower alkyl groups such as methyl, ethyl, or propyl are attached to a linear alkyl chain. Exemplary alkyl groups include methyl, ethyl, n-propyl, propyl, n-butyl, t-butyl, n-pentyl, 3-pentyl, and the like.

The term "carbocycle" means a cyclic hydrocarbon chain having about 5 to about 8 ring carbons such as cyclopentyl, cylcohexyl, etc. These groups can be optionally substituted with one or more functional groups.

The term "aryl" means an aromatic monocyclic or multi-cyclic (polycyclic) ring system of 6 to about 19 carbon atoms, or of 6 to about 10 carbon atoms, and includes arylalkyl groups. The ring system of the aryl group may be optionally substituted. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

"Unsubstituted" atoms bear all of the hydrogen atoms dictated by their valency.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, lower alkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. When a substituent is keto (i.e., =0), then two hydrogens on the atom are replaced. Combinations of substituents and/or variables are permissible only if such combinations result in stable compounds. A "stable compound" is meant to be a compound that is sufficiently robust to survive isolation to a useful degree of purity from a reaction mixture, and formulation into an efficacious therapeutic agent.

The term "halogen" means chloro, bromo, or iodo.

The term "copolymer" refers to a polymer derived from more than one species of monomer.

The term "alternating copolymer" or "alternating polymer" refers to a copolymer consisting of two or more species of monomeric units that are arranged in an alternating sequence in which every other building unit is different $(-M_1M_2-)_n$.

The term "random copolymer" or "random polymer" refers to a copolymer in which there is no definite order for the sequence of the different monomeric building blocks, e.g., $(-M_1M_2M_1M_1M_2M_1M_2M_2-)$.

The term "statistical copolymer" or "statistical polymer" refers to a copolymer in which the sequential distribution of the monomeric units obeys known statistical laws.

The term "block copolymer" or "block polymer" refers to a macromolecule consisting of long sequences of different repeat units. Exemplary block copolymers include, but are not limited to $A_nB_m$, $A_nB_mA_m$, $A_nB_mC_k$, or $A_nB_mC_kA_n$.

The term "a derivative thereof" refers to a salt thereof, an ester thereof, a free acid form thereof, a free base form thereof, a solvate thereof, a deuterated derivative thereof, a hydrate thereof, an N-oxide thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

The term "biocidal" as used here means activity that inactivates microorganisms and/or virus particles.

The term "zwitterion" as used herein refers to a moiety including both positively and negatively charged groups in the same molecule. Without being bound by any theory, it is believed that the zwitterion functional groups may provide improved hydrophilicity and biocompatibility.

Methods of Forming Hydrogel-Coated Substrates

In one embodiment of the present application, the method of forming a hydrogel-coated substrate may include applying an aqueous pre-hydrogel solution to a substrate. In some embodiments, the substrate may be, for example, silicone, latex, rubber, polyethylene, polyether ketone, polyurethane, polyester, a nylon polymer, a block copolymer of polyether and polyester polymers, a thermoplastic hydrocarbon polymer, a copolymer thereof, or a combination thereof. In some embodiments, the substrate may be selected from a variety of materials including, for example, siloxanes, polydimethylsiloxanes, polysiloxanes, ultra-high molecular weight polyethylenes, polyetherketones (including polyetheretherketone (PEEK) and polyetherketoneketone (PEKK)), thermoplastic polyurethanes (TPU), polyesters such as polyethylene terephthalate (PET), nylon polymers such as nylon-11 and nylon-12, block copolymers of polyether and polyester polymers, synthetic rubbers, natural rubber, or a combination thereof. In certain embodiments, the substrate may be one that resists water contact and is difficult to coat with a conventional hydrogel.

In certain embodiments, the substrate may be a device surface. The device may be, for example, a catheter, a stent, a pump, a bandage, gauze, a suture, an implantable device, or a combination thereof.

In some embodiments, the aqueous pre-hydrogel solution may be applied to the substrate by dip-coating. This may be carried out by heating the solution to a temperature of 20° C. to 100° C. and cooling to a temperature of 20° C. to 0° C. In one non-limiting example, the aqueous pre-hydrogel solution comprises a blend of acrylamide and agarose, dissolved in water. In the non-limiting example, the aqueous pre-hydrogel solution may be heated to 90° C. and cooled to 45° C., forming a hydrogel on the substrate at room temperature.

The polymer included in the aqueous pre-hydrogel solution may be, for example, agar, chitosan, an N-isopropylacrylamide copolymer, a poloxamer, a poly(ethylene oxide)/poly(lactic acid) block copolymer, poly(ethylene oxide)/poly(propylene oxide) block copolymers, alginate, dextran, polysaccharides, amphiphilic copolymers, copolymers thereof, and combinations thereof.

In certain embodiments, the aqueous pre-hydrogel solution may also comprise an initiator. Suitable initiators depend greatly on the details of the polymerization, including the types of monomers being used, the type of catalyst system, the solvent system, and the reaction conditions.

In some embodiments, the initiator may be a photoinitator, a thermal initiator, an ultraviolet initiator, or another type of initiator.

Photo initiators when irradiated with UV light, produce free radicals which initiate photopolymerization. The initiator may be, for example, 2-hydroxy-4'-(2-hydroxyethoxy)-2-methylpropiophenone a benzoin ether, a benzil ketal, an a-dialkoxyacetophenone, an α-hydroxyphenone, an α-amino-alkylphenone, an acylphosphine oxide, a benzophenone/amine, a thioxanthone/amine, azobisisobutyronitrile, lithium phenyl-2,4,6-trimethylbenzoylphosphinate, or a combination thereof. Other examples of suitable photo initiators include acetophenone; anisoin; anthraquinone; anthraquinone-2-sulfonic acid, sodium salt monohydrate; tricarbonylchromium; benzil; benzoin, sublimed; benzoin ethyl ether; benzoin isobutyl ether; benzoin methyl ether; benzophenone; benzophenone/1-hydroxycyclohexyl phenylketone, 50/50 blend; 3,3',4,4'-benzophenonetetracarboxylic dianhydride; 4-benzoylbiphenyl; 2-benzyl-2-(dimethylamino)-4'-morpholinobutyrophenone; 4,4'-bis(diethylamino)benzophenone; 4,4'-bis(dimethylamino)benzophenone; camphorquinone; 2-chlorothioxanthen-9-one; (cumene)cyclopentadienyliron(II) hexafluorophosphate; dibenzosuberenone; 2,2-diethoxyacetophenone; 4,4'-dihydroxybenzophenone; 2,2-dimethoxy-2-phenylacetophenone; 4-(dimethylamino)benzophenone; 4,4'-dimethylbenzil; 2,5-dimethylbenzophenone; 3,4-dimethylbenzophenone; diphenyl (2,4,6-trimethylbenzoyl)phosphine oxide/2-hydroxy-2-methylpropiophenone, 50/50 blend; 4'-ethoxyacetophenone; 2-ethylanthraquinone; ferrocene; 3'-hydroxyacetophenone; 4'-hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methylbenzophenone; methybenzoylformate; 2-methyl-4'-(methylthio)-2-morpholinopropiophenone; phenanthrenequinone; 4'-phenoxyacetophenone; thioxanthen-9-one; triarylsulfonium hexafluoroantimonate salts, mixed, 50% in propylene carbonate; triarylsulfonium hexafluorophosphate salts, mixed, 50% in propylene carbonate, or a combination thereof.

Thermal radical initiators decompose upon heating into radical fragments which initiate polymerization. Exemplary thermal radical initiators include ammonium persulfate; sodium metabisulfite; benzoyl peroxide; di-t-amyl peroxide; t-butyl peroxy benzoate; di-cumyl peroxide; azobisisobutyronitrile (AIBN); 1,1' azobis(cyclohexanecarbonitrile) (ABCN); 4,4'-Azobis(4-cyanovaleric acid) (ACVA); 2,2'-azobis(2,4-dimethylpentanenitrile); and 2,2'-azobis(cyclohexanecarbonitdle).

The initiator in the pre-gel solution can range from about 0.01 wt % to 10 wt %.

In certain embodiments, the aqueous pre-hydrogel solution may further comprise a cross-linking agent. Suitable classes of cross-linkers are selected from the group consisting of diisocynates, anhydrides, multiply (meth)acrylated cross linkers, polyacids, and acid halides. The cross-linking agent may be, for example, poly(ethylene glycol)dimethacrylate, tetramethylethylenediamine, carboxybetaine diacrylamide cross-linker, carboxybetaine diacrylate, other bifunctional and multi-functional monomers and macromers, or a combination thereof. The crosslinking agent may range from 0.01 wt % to 80 wt % of the pre-hydrogel solution.

The crosslinking agents interact with the pendent reactive groups on the polymer, oligomer, or macromer.

The crosslinking agents may be diisocynates. Exemplary diisocyanates suitable for the present invention include polymeric methylene diphenyl diisocyanate (PMDI), 1,4-tetramethylene diisocyanate, 1,6-hexamethylene diisocyanate (HDI), 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanato-methyl-3,5,5-trimethylcyclohexane (isophorone diisocyanate or IPDI), 4,4'- and/or 2,4'-diisocyanato-dicyclohexylmethane, 1,3- and 1,4-bis(isocyanato-methyl)-cyclohexane, bis-(4-isocyanato-3-methyl-cyclohexyl)-methane, xylylene diisocyanate, α,α,α',α'-tetramethyl-1,3- and/or -1,4-xylylene diisocyanate, 1-isocyanato-1-methyl-4(3)-isocyanatomethyl cyclohexane, 2,4- and/or 2,6-hexahydrotoluylene diisocyanate, 2,4- and/or 2,6-toluene diisocyanate, 2,4- and/or 4,4'-diphenylmethane diisocyanate, or 4,4'-Methylenebis(cyclohexyl isocyanate), etc. Additionally, mixtures of these diisocyanates may also be used.

Other crosslinking agents that could interact with the residual reactive groups on the hydrogel polymer include multiply (meth)acylated cross-linkers such as diethyleneglycol dimethacrylate (DEGDMA), diethylene glycol diacrylate, triethylene glycol dimethacrylate (TEGDMA), ethyleneglycol dimethacrylate (EGDMA), hexane-1,6-diol diacrylate (HDDA), ethylene glycol diacrylate, ethylene glycol dimethacrylate, poly(ethylene glycol) diacrylate, poly(ethylene glycol) dimethacrylate, tetra(ethylene glycol) diacrylate, or triethylene glycol dimethacrylate.

Furthermore, crosslinking agents such as poly acids, anhydrides, and acid halides may also be used. Exemplary cross linkers of these types include maleic acid, 2-methylmaleic acid, itaconic acid, 2-methylitaconic acid, α,β-methyleneglutaric acid, maleic anhydride, itaconic anhydride, acrylic anhydride, methacrylic anhydride, 1, 4-Phenylenediacryloyl chloride, etc.

The concentration of the monomer with antimicrobial activity and the monomer with antifouling activity used in any of the above described polymerization reactions depends partially on the solubility of the monomer and the polymer products as well as the evaporation temperature of the solvent. Solvent concentration can also affect the gelation of the polymer. Insufficient solvent can cause the polymer to crosslink in a shorter time period without ever reaching high enough conversions. The concentration of the monomer dissolved in the solvent in reactions may range from 1% to 100% weight percentage monomer. Typically, a monomer concentration of less than 90 wt % is suitable to ensure the solubility of the resulting hydrogelable polymers and additionally to prevent premature cross-linking and gelation.

Suitable solvents for use in the process of preparing the hydrogelable polymer of the present application is selected based the requirements of monomer solubility and a boiling point compatible with the type of polymerization being used and the polymerization temperature. Exemplary solvents useful for the formation of the copolymers described herein include, but are not limited water, methanol, ethanol, methylene chloride, toluene, dioxane, THF, chloroform, cyclohexane, dimethyl sulfoxide, dimethyl formamide, acetone, acetonitrile, n-butanol, n-pentanol, chlorobenzene, diethylether, tert butanol, 1,2,-dichloroethylene, diisopropylether, ethanol, ethylacetate, ethylmethylketone, heptane, hexane, isopropylalcohol, isoamylalcohol, methanol, pentane, n-propylalcohol, pentachloroethane, 1,1,2,2,-tetrachloroethane, 1,1,1,-trichloroethane, tetrachloroethylene, tetrachloromethane, trichloroethylene, water, xylene, benzene, nitromethane, glycerol, and mixtures thereof.

The solvent can further include stabilizers, surfactants, or dispersants. Suitable surfactants include ionic and nonionic surfactants such as alkyl polyglycol ethers such as ethoxylation products of lauryl, oleyl, and stearyl alcohols; alkyl phenol polyglycol ethers such as ethoxylation products of octyl- or nonylphenol, diisopropyl phenol, triisopropyl phenol; alkali metal ammonium salts of alkyl, aryl or alkylaryl sulfonates, sulfates, phosphates, and the like, including sodium lauryl sulfate, sodium octylphenol glycolether sulfate, sodium dodecylbenzene sulfonate, sodium lauryldiglycol sulfate, and ammonium tritertiarybutyl phenol and penta- and octa-glycol sulfonates, sulfosuccinate salts such as disodium ethoxylated nonylphenol half ester of sulfosuccinic acid, disodium n-octyldecyl sulfosuccinate, sodium dioctyl sulfosuccinate, and the like.

In certain embodiments, the monomer with antimicrobial activity may be, for example, N-halamine, hydantoin acrylamide, 2,2,6,6-tetramethyl-4-piperidinyl methacrylate, N-halimides, N-halamides, or a combination thereof.

Suitable N-halamine monomers include, without limitation,

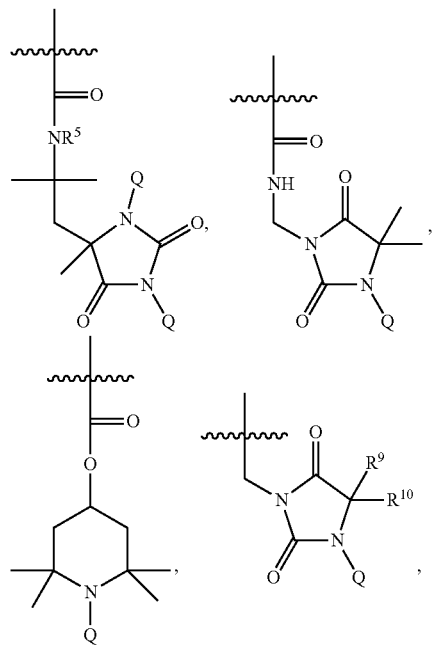

and derivatives thereof, wherein
  $R^5$ is H, Cl, Br, or I;
  $R^9$ and $R^{10}$ and the carbon to which they are bound join to form a carbocyclic ring, or are individually $CH_3$; and
  Q is independently H, Cl, Br, or I, and
  wherein

indicates a point of attachment to a polymerizable moiety, such as a carbon-carbon double bond.

Additional N-halamine monomers that are suitable for use in the hydrogel described herein are disclosed in Dong et al., "Chemical Insights into Antibacterial N-Halamines," *Chemical Review* 117:4806-4962 (2017), which is hereby incorporated by reference in its entirety. In particular, exemplary N-halamine monomer moieties that can be incorporated into the copolymers described herein include, but are not limited to,

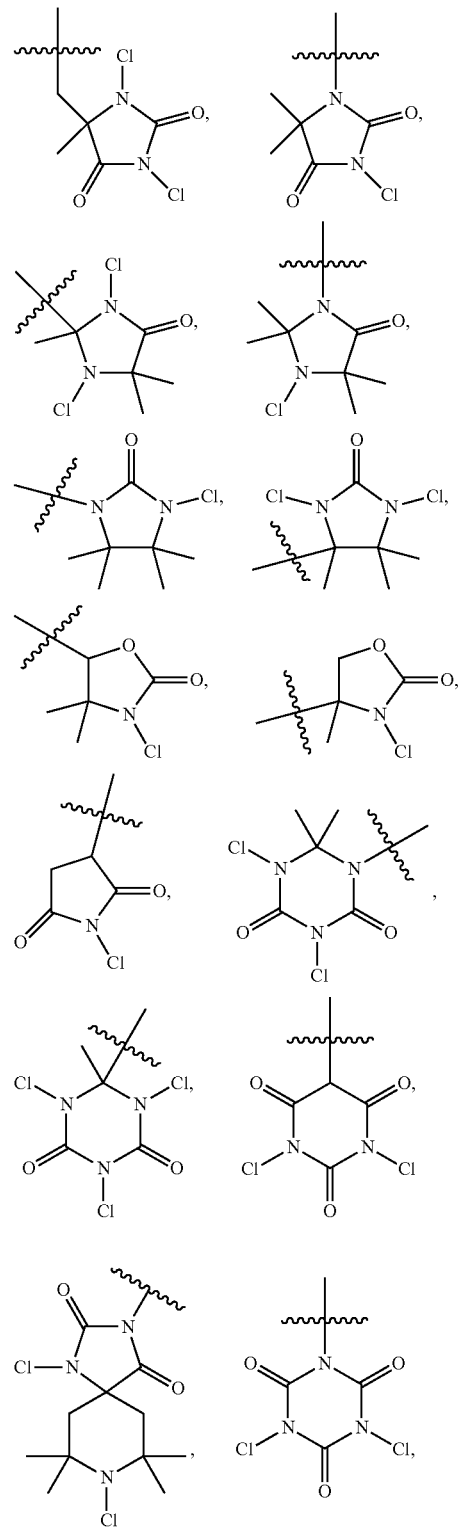

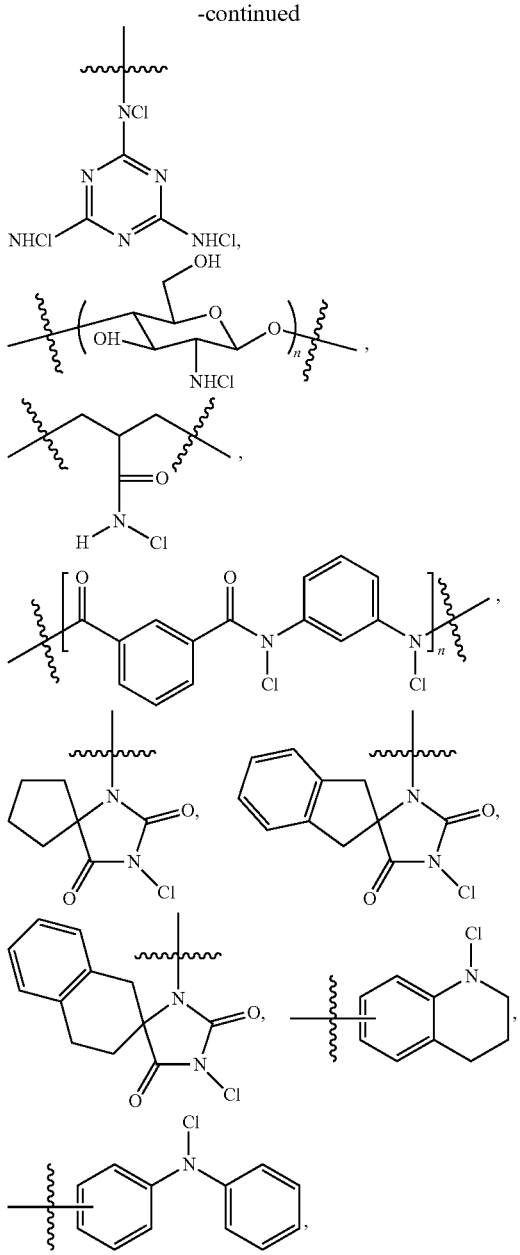

and derivatives thereof, wherein

indicates a point of attachment to a polymerizable moiety, such as a carbon-carbon double bond, amide, acrylate, or methacrylate group.

Additional N-halamine monomers that are suitable for incorporation into the copolymers as described herein include those disclosed in U.S. Pat. No. 8,496,920 to Worley et al., U.S. Pat. No. 6,969,769 to Worley et al., U.S. Pat. No. 6,768,009 to Sun et al., U.S. Pat. No. 5,882,357 to Sun et al., U.S. Pat. No. 7,084,208 to Sun et al., U.S. Pat. No. 6,482,756 to Li et al., U.S. Pat. No. 7,858,539 to Li et al., U.S. Patent Appl. Publ. No. 2015/0315389 to Cao et al., U.S. Patent Appl. Publ. No. 2016/0106098 to Worley et al., and U.S. Patent Appl. Publ. No. 2015/0166796 to Sun et al., all of which are hereby incorporated by reference in their entirety.

The monomers with antimicrobial activity, the monomers with antifouling activity, and the polymers incorporated into the hydrogel as described here may be unsubstituted, or may be optionally substituted.

In some embodiments, monomer with antifouling activity may be, for example, sulfobetaine, [2-methacryloyloxy) ethyl] dimethyl-(3-sulfopropyl) ammonia hyroxide, carboxybetaine methacrylate, methacryloyloxyethyl phosphorylcholine, serine methacrylate, lysine methacrylamide, ornithine methacrylamide, 3-[[2-(Methacryloyloxy)ethyl]-dimethylammonio]propane-1-sulfonate, 3-[[2-(Methacryloyloxy)ethyl]dimethylammonio]propionate, 3-[(3-Acrylamidopropyl)dimethylammonio]propanoate, sulfobetaine acrylate, sulfobetaine methacrylamide, sulfobetaine acrylamide, carboxybetaine acrylate, carboxybetaine acrylamide, carboxybetaine methacrylamide, serine acrylate, lysine acrylamide, ornithine acrylamide or a combination thereof.

The ratio of the monomer with antimicrobial activity to the monomer with antifouling activity in the pre-hydrogel solution can range from 99:1 to 1:99.

In some embodiments, the aqueous pre-hydrogel solution may be de-gassed before it is applied to the substrate to avoid the effect of dissolved oxygen. The aqueous pre-hydrogel solution may be de-gassed using an ultra-sonic bath or vacuum.

In polymerizing the aqueous pre-hydrogel solution, thereby forming a coated substrate having a conformal hydrogel coating and a non-conformal hydrogel coating, the polymerizing may be carried out with, for example, ultra-violet irradiation, oxidative polymerization, thermal polymerization, delayed gel-cross-linking, or a combination thereof. In one non-limiting embodiment, the irradiation may be operable at a wavelength of 365 nm and approximately an energy level of 7300 mW/cm$^2$. In certain embodiments, the irradiating is carried out in the presence of oxygen, and in some embodiments, the irradiating is carried out in open air.

In some embodiments, the polymerizing may achieve gradient cross-linking. During cross-linking, exposing the surface to oxygen-containing gases, optionally air, in the presence of argon (Ar) and/or other inert gases may allow oxygen to quench and inhibit radicals in the hydrogel and cause gradient cross-linking. In another embodiment, gradient cross-linking may be achieved by chemical cross-linking. For example, water soluble monomers may be converted into hydrogels using crosslinking agents such as tetramethylethylenediamine. Gradient cross-linking may result in a conformal hydrogel coating adjacent to the substrate, with the degree of cross-linking decreasing with distance from the substrate. Gradient cross-linking may, therefore, aid removal of the non-conformal hydrogel coating.

The conformal hydrogel coating may be adjacent to the substrate, and the non-conformal hydrogel coating may be adjacent to the conformal hydrogel coating. In certain embodiments, the conformal hydrogel coating may have a thickness from about 10 µm to about 200 µm. The conformal hydrogel coating may have a thickness of, for example, about 10 µm, about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170

µm, about 180 µm, about 190 µm, about 200 µm, or any range between these values, including endpoints.

In contacting the coated substrate with a swelling agent, the swelling agent may comprise an aqueous solution. In one embodiment, the aqueous solution may be water, a buffer, a mixture of water and a miscible solvent (e.g., methanol, or ethanol), or a combination thereof. In further embodiments, the aqueous solution includes halogens. In some embodiments, contacting the coated substrate with the swelling agent may be carried out for between 1 minute and 10 minutes at a temperature of 0° C. to 200° C. The contacting may be carried out for, by way of example, about 1 minute, about 2 minutes, about 3 minutes, about 4 minutes, about 5 minutes, about 6 minutes, about 7 minutes, about 8 minutes, about 9 minutes, about 10 minutes, or any range between these values, including endpoints.

In some embodiments, the hydrogels as disclosed herein are halogenated to assume biocidal activity. Furthermore, upon the loss of biocidal activity due to extensive use, the activity can be recharged by subsequent halogenation. Halogenation of the hydrogels can be accomplished by exposure to a source of free halogen. For chlorination the process can be conducted in aqueous solution using such sources as gaseous chlorine, sodium hypochlorite bleach, calcium hypochlorite, chloroisocyanurates, and chlorinated hydantoins. Likewise, for bromination the process can be accomplished by exposure in aqueous solution to sources, such as molecular bromine liquid, sodium bromide in the presence of an oxidizer, such as potassium peroxy monosulfate or hypochlorite bleach, and brominated hydantoins. Halogenation can also be affected in organic solvents, such as methylene chloride, or by employing free radical halogenating agents, such as tert-butyl hypochlorite. Additionally, The halogenation process can optionally be combined with the swelling process by incorporating a source of halogens into the aqueous solution used to swell the hydrogel. For example, the swelling agent can be an aqueous solution of sodium hypochlorite (bleach).

Optionally, the halogenation of the hydrogel can be accomplished after the swelling process. The process for the formation of the hydrogel coating can include treating the conformal hydrogel coating with a halogen solution after said removing the non-conformal hydrogel coating from the coated substrate.

In removing the non-conformal hydrogel coating from the coated substrate, thereby leaving the conformal hydrogel coating on the substrate to form the hydrogel-coated substrate, the non-conformal hydrogel coating can be peeled away from the substrate. The non-conformal hydrogel coating may include non-cross-linked and/or loosely cross-linked hydrogel components. When the non-conformal hydrogel coating is contacted with the swelling agent, it may swell and peel or be easily removable from the conformal hydrogel coating, thereby easing removal of the non-conformal hydrogel coating. Removal of the non-conformal hydrogel may be carried out at a temperature of 0° C. to 200° C.

In certain embodiments, the method of the present application may further comprise treating the substrate with a radical initiator, before applying the aqueous pre-hydrogel solution. The radical initiator can be selected from the group consisting of 2-hydroxy-4'-(2-hydroxyethoxy)-2-methylpropiophenone, a benzoin ether, a benzil ketal, an a-dialkoxyacetophenone, an α-hydroxyphenone, an α-amino-alkylphenone, an acylphosphine oxide, a benzophenone/amine, a thioxanthone/amine, azobisisobutyronitrile, poly(ethylene glycol) dimethacrylate, 2-hydroxy-2-methylpropiophenone and combinations thereof. Such treatment may be carried out at a temperature of 0° C. to 200° C. In one embodiment, treating the substrate with the radical initiator before applying the aqueous pre-hydrogel solution can result in formation of one or more chemical bonding sites on the substrate. Such chemical bonding sites may promote chemical bonding, such as covalent bonds, ionic bonds and/or hydrogen bonds, between the between the aqueous pre-hydrogel solution and the substrate.

In some embodiments, the method may further comprise treating the substrate with a cross-linker, an oligomer, a macromer, polyacrylamide, polyvinyl alcohol, polyethylene glycol, polyethylene oxide, or a combination thereof before applying the aqueous pre-hydrogel solution. Such treatment may be carried out at a temperature of 0° C. to 200° C.

FIG. 1A illustrates a schematic representation of an embodiment of a method as described herein. In the embodiment 100, an aqueous pre-hydrogel solution 120 is applied to a substrate 110, resulting in the solution-coated substrate 130. The aqueous pre-hydrogel solution 120 comprises a mixture of a monomer with antimicrobial activity, and a monomer with antifouling activity that when polymerized together are able to form a hydrogel. The embodiment 100 further comprises polymerizing the solution-coated substrate 130, thereby forming a coated substrate 140 having a conformal hydrogel coating and a non-conformal hydrogel coating. The embodiment 100 further comprises contacting the coated substrate 140 with a swelling agent, and removing the non-conformal hydrogel coating 150 from the coated substrate 140, thereby leaving the conformal hydrogel coating 160 on the substrate to form the hydrogel-coated substrate.

The present application provides hydrogels with antimicrobial and antifouling properties. These hydrogels can be based on copolymers of N-halamine monomers and zwitterionic monomers. When polymerized together the copolymer structure of the hydrogel can include alternating copolymers, random copolymers, statistical copolymers, segmented polymers, block copolymers, multiblock copolymers, gradient copolymers, graft copolymers, star copolymers, branched copolymers, hyperbranched copolymers and combinations thereof. The hydrogeled copolymers can be used alone or they can be included in a composition, i.e., blended/mixed with other materials.

Coated Substrates and Coatings

A further embodiment relates to a coated substrate including a substrate and a conformal hydrogel coating on the substrate. The conformal hydrogel coating comprises an antimicrobial agent, a zwitterionic antifouling agent, and either a backbone polymer, oligomer, or macromer wherein the antimicrobial agent, the zwitterionic antifouling agent, and either the backbone polymer, oligomer, or macromer are polymerized together.

A further embodiment of the present application is directed to a hydrogel coating that may comprise a N-halamine antimicrobial agent, a zwitterionic antifouling agent, and either a backbone polymer, oligomer, or macromer, wherein the antimicrobial agent, the zwitterionic antifouling agent, and either the backbone polymer, oligomer, or macromer are polymerized together.

In some embodiments, the substrate may be, for example, silicone, latex, rubber, polyethylene, polyether ketone, polyurethane, polyester, a nylon polymer, a block copolymer of polyether and polyester polymers, a thermoplastic hydrocarbon polymer, a copolymer thereof, or a combination thereof. In certain embodiments, the substrate may be a device surface. The device may be, for example, a catheter, a stent, a pump, a bandage, gauze, a suture, an implantable device, or a combination thereof.

In certain embodiments, the antimicrobial agent may be, for example, N-halamine, hydantoin acrylamide, 2,2,6,6-tetramethyl-4-piperidinyl methacrylate, N-halimides, N-halamides, or a combination thereof. In some embodiments, the antifouling agent may be a zwitterionic moiety. The zwitterionic moiety may be, for example, sulfobetaine, [2-methacryloyloxy)ethyl] dimethyl-(3-sulfopropyl) ammonia hyroxide, carboxybetaine methacrylate, methacryloyloxyethyl phosphorylcholine, serine methacrylate, lysine methacrylamide, ornithine methacrylamide, 3-[[2-(Methacryloyloxy)ethyl]-dimethylammonio]propane-1-sulfonate, 3-[[2-(Methacryloyloxy)ethyl]dimethylammonio]propionate, 3-[(3-Acrylamidopropyl)dimethylammonio]propanoate, sulfobetaine acrylate, sulfobetaine methacrylamide, sulfobetaine acrylamide, carboxybetaine acrylate, carboxybetaine acrylamide, carboxybetaine methacrylamide, serine acrylate, lysine acrylamide, ornithine acrylamide, or a combination thereof.

In certain embodiments, the conformal hydrogel coating may have a thickness from about 10 µm to about 200 µm. The conformal hydrogel coating may have a thickness of, for example, about 10 µm, about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm, or any range between these values, including endpoints.

Figure 22:
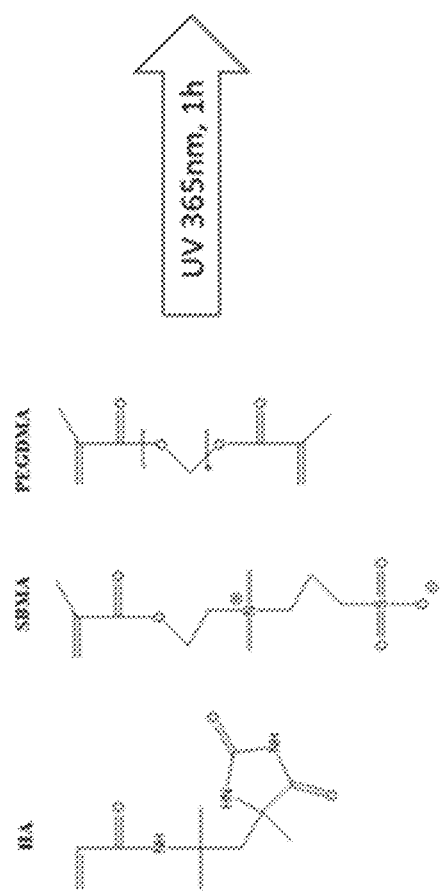
FIG. 22 is a schematic representation of the polymerization of antimicrobial and antifouling monomers to form a conformal hydrogel coating.
Figure 22:
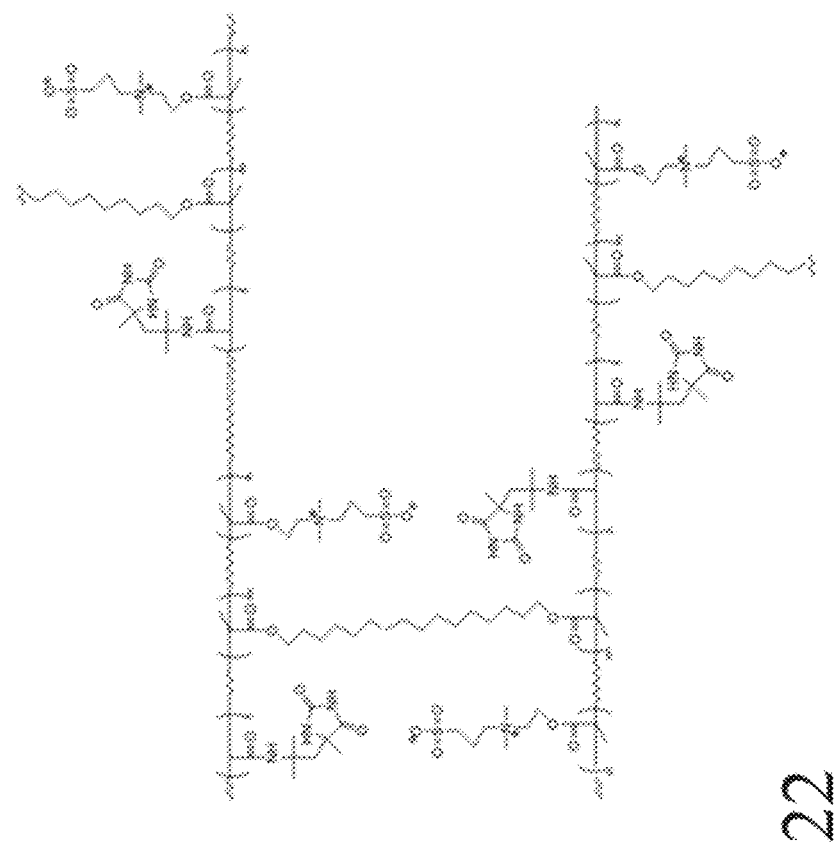
Figure 23:
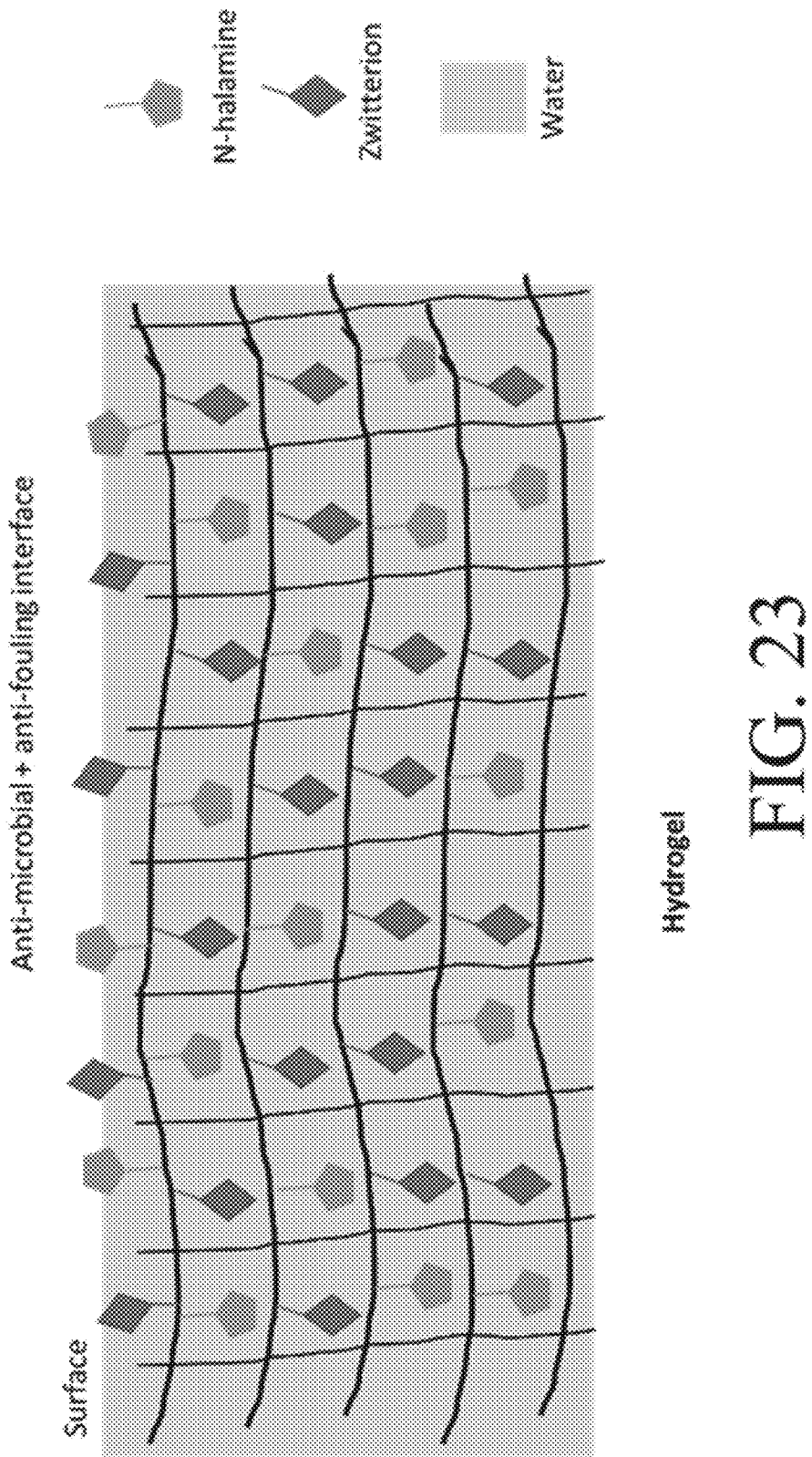
FIG. 23 is a schematic representation of a conformal hydrogel coating having antimicrobial and antifouling properties.
Figure 24:
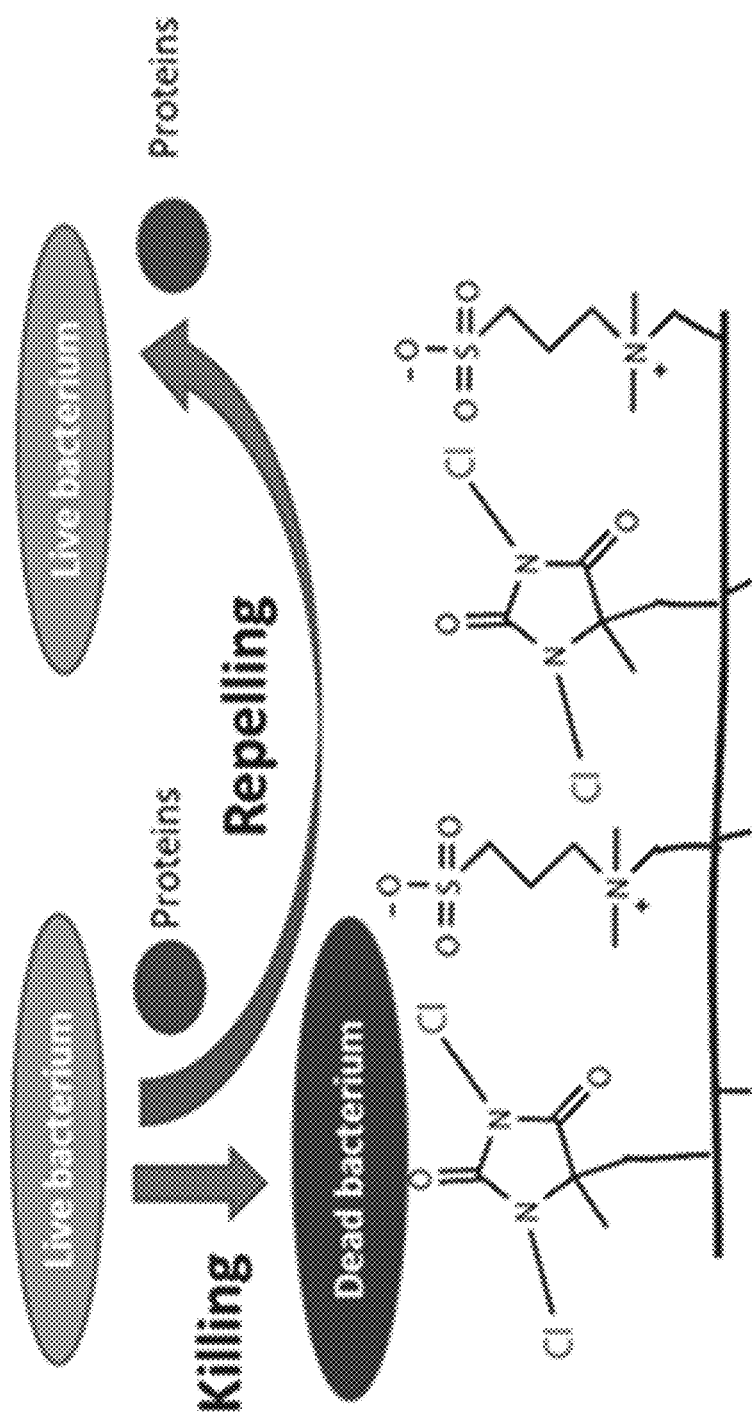
FIG. 24 is a schematic representation of a mechanism of making a conformal hydrogel coating having antimicrobial and antifouling properties.

In some embodiments, a hydrogel coating may comprise a polymerized N-halamine antimicrobial agent and a polymerized zwitterionic antifouling agent, as described herein. FIG. 22 is a schematic representation of the polymerization of an antimicrobial monomer and an antifouling monomer to form a hydrogel coating as described herein. Similarly, FIG. 23 is a schematic representation of a conformal hydrogel coating having antimicrobial properties and antifouling properties, as described herein. FIG. 24 is a schematic representation of a mechanism of making such a conformal hydrogel coating.

Preferences and options for a given aspect, feature, embodiment, or parameter of the application should, unless the context indicates otherwise, be regarded as having been disclosed in combination with any and all preferences and options for all other aspects, features, embodiments, and parameters of the application.

The following examples are presented to illustrate various aspects of the present application, but are not intended to limit the scope of the claimed invention.

EXAMPLES

Example 1—Preparation of Conformal Hydrogel Coatings

Materials

The following chemicals and reagents were used for the preparation of hydrogel coating: Acrylamide (AAm), N,N'-Methylenebis (acrylamide) (MBAA), [3-(Methacryloylamino) propyl] dimethyl(3-sulfopropyl)ammonium hydroxide inner salt (SBMA), FITC-dextran, N-(1, 1-Dimethyl-3-oxobutyl) acrylamide (DA), and $Na_2S_2O_3$ were purchased from Sigma Aldrich (Saint Louis, USA). Agar and benzophenone were purchased from Fisher Bioreagents (Pittsburgh, USA). Irgacure 2959 was purchased from BASF (Florham Park, USA). Hydantoin acrylamide (HA) was synthesized from DA. Commercial Clorox was used as bleach. Fibrinogen-Alexa Fluor™ 488 Conjugate was purchased from Thermo Fisher Scientific (Eugene, USA). Medical grade silicone tubing was purchased from VWR international (Corning, USA). Commercial urinary catheters were purchased from Mohawk hospital equipment, Inc (Mohawk, USA).

Preparation of Hydrogel-Coated Samples

Hydrogel coating on catheter/silicone tubing. Catheter/tubing samples were pretreated with benzophenone solution (10% w.t. in ethanol) for 10 minutes, washed with ethanol three times, and vacuum dried following a previously reported method. The benzophenone pretreatment can be replaced with soaking the catheter in 1% tert-butylperoxy 2-ethylhexyl (TBEC) in isopropyl alcohol (IPA) for 2 hours at room temperature. The pre-gel solution was prepared at 90° C. (concentration shown in Table 1), and was degassed using a VWR® Ultrasonic Cleaner at 45° C. for 30 minutes.

TABLE 1

Weight concentrations of hydrogel coating components

| Type | Weight percentage (wt %) | | | | | |
|---|---|---|---|---|---|---|
| | Acrylamide | Agar | N-halamine | SBMA | MBAA | Irgacure 2959 |
| AAgel | 24.2 | 4 | 0 | 0 | 0.016 | 0.76 |
| AASgel | 14.0 | 4 | 0 | 40 | 0.016 | 0.76 |
| AAHgel | 22.4 | 4 | 6 | 0 | 0.016 | 0.76 |
| AASHgel | 18.7 | 4 | 6 | 15 | 0.016 | 0.76 |

The catheter/tubing/device (substrate) was then dip-coated in the pre-gel solution at a temperature from 15° C. to 50° C. The amount of solution to use can be from not fully covering the substrate to use of excess solution to cover the substrate. In one embodiment of dip-coating, the substrate was dipped into the hydrogel coating solution three times at three seconds each time at room temperature in an excess of solution over the device. In another embodiment, the substrate was placed in a groove, and the hydrogel coating solution was poured onto the substrate at 45° C. The substrate was rolled to ensure the precursor formed a hydrogel coating that fully covered the substrate. In this case, the precursor does not have to cover the substrate.

After the weak hydrogel coating had coated the substrate, UV treatment was then immediately performed using OmniCure® UV Curing System for 120 seconds at a wavelength ranging from 245 to 400 nm. The substrate being rotated to ensure full exposure to UV light. At this step, the substrate need not remain in the hydrogel coating solution.

Following cross-linking, the substrate coated with the cross-linked hydrogel coating is immersed in water for one to ten minutes to induce swell peeling. While immersion in an excess of water is recommended, the substrate can instead be rolled/rotated in a shallow pool of water. After swell-peeling, the coated catheter can be dried, autoclaved and stored. Upon use, the catheter should be rinsed with water or any appropriate buffer. In one embodiment, the buffer can be phosphate-buffered saline (PBS), pH 7.4.

One embodiment of the complete process involves pretreating the substrate by immersing into excess benzophenone solution (10% w.t. in ethanol) for 10 minutes, then washing with ethanol three times, and vacuum dried for 5 minutes. The hydrogel coating solution was prepared at 90° C. in 5 mL water (concentration shown in Table 1), and was degassed using a VWR® Ultrasonic Cleaner at 45° C. for 30 minutes. The sample was dipped into an excess of precursor for three times at three seconds each time. The sample with weak hydrogel coating was immediately taken to UV treatment using an OmniCure® UV Curing System for 120 seconds, the sample was rotated to ensure full exposure to UV light. UV radiation sources may be operable at a wavelength of 365 nm and approximately an energy level of 7300 mW/cm$^2$.

Hydrogel Coating on PDMS

PDMS pads were prepared from similar materials as silicone uretic catheters or tubings to allow a proper characterization of the coating otherwise hampered by the curved surface of the catheter/tubing. PDMS pads prepared in Petri dishes were treated with benzophenone solution (10 w.t. % in ethanol) for 10 minutes, washed three times with ethanol and vacuum dried. The pre-gel solution (45° C.) mentioned above was poured into these Petri dishes (at r.t.), and formed an agar hydrogel layer on the PDMS surface. Next, UV-crosslinking and swell-peeling methods were used to form the thin hydrogel coating layer.

Crosslinking was performed in open air to purposely allow gradual oxygen inhibition of free radicals to generate a gradient of crosslinking density across the hydrogel layer, a step that has not yet been described by others. During the cross-linking, oxygen is not inhibited and is diffused constantly into the hydrogel, thereby quenching free radicals. As a result of oxygen quenching, high radical concentration was only observed in a narrow range near the catheter surface, and the degree of cross-linking along hydrogel thickness was different. Hydrogels prepared with free radical polymerization usually require oxygen inhibition to avoid oxygen quenching which can stop the reaction.

The final step of swell-peeling involves immersing the coated catheter in water to allow non-crosslinked or loosely crosslinked hydrogel to swell and fall off, leaving only a thin conformal layer of strongly bonded tough hydrogel. In one embodiment, the cross-linked device was immersed in water for 3 minutes and swell-peeled. After weak or non-crosslinked hydrogel fell off, the coating left on the catheter/implantable medical device was approximately 30 μm in thickness.

Example 2—Characterizations of Mechanical and Lubrication Properties of Conformal Hydrogel Coatings Fluorescence microscope images were obtained using an EVOS® FL Cell Imaging System. To obtain images of coated silicone tubing, the hydrogel coating was stained with FITC-dextran. Scanning Electron Microscope (SEM) images were taken on a Zeiss Gemini 500 Scanning Electron Microscope (SEM).

Mechanical property tests of the hydrogel coatings were carried out in air at ambient temperature. The stretching of hydrogel-coated silicone tubing was carried out using an Instron 4680 mechanical testing instrument with grip-to-grip separation speed of 10 mm/min. The coating was 1-inch long on a 2.5-inch tubing and was stained with a red food dye for better visualization.

Lubricating properties of hydrogel coatings on PDMS was tested using a ball-on-three-plates method on a TA Instruments DHR3 Rheometer; water was used as lubricating liquid to simulate in-vivo conditions for catheters. Frictional forces generated during sliding contact were monitored by a strain gauge and measured as a function of speed (0.001-10 rad/s) at a fixed load of 1.5 N.

Fourier Transformed Infrared (FTIR) analysis was obtained in transmission mode on a Bruker Vertex V80V Vacuum FTIR system.

Protein Adsorption Tests

Protein adsorption tests were carried out using FITC-labeled fibrinogen (1 mg/mL) dissolved in phosphate-buffered saline (PBS), pH 7.4. Silicone tubings (without coating/with AAm-Agar coating/with AAm-Agar-SBMA coating) were cut into ¼ inch segments and equilibrated in PBS buffer for 30 minutes. The PBS solution was then replaced with fibrinogen solution, which remained in contact for another 30 minutes. After this period, the tubing segments were gently washed three times with PBS buffer, and fluorescence microscope images were obtained on an EVOS® FL Cell Imaging System. The adsorbed protein was presented as the relative fluorescence intensity by processing the images with ImageJ.

Implantation, Explantation, and Histological Analyses

The silicone tubing samples were cut into ½ inch segments and plugged with PDMS, before being implanted subcutaneously in C57Bl/6 mice for four weeks. The implantation procedure followed previous reports. Mice were purchased from Jackson Laboratory (Sacramento, USA) and each mouse was subcutaneously implanted with four segments (one without coating, one with AAgel coating, one with AASgel coating, and one with AASHgel coating). Five replicates of each type of coated silicone tubing were implanted into five different mice to provide statistical significance in the histological studies. Mice were anesthetized using isoflurane and shaved. Four longitudinal incisions (no longer than 0.5 cm) were made on either side of the flank using surgical scissors to provide access to subcutaneous space. Subcutaneous pockets on either side of the incision were then created by blunt dissection, followed by implantation of the tubing segments. The incisions were then closed using 5-0 Nylon non-absorbable suture. Mice were monitored until recovery from anesthesia and housed for four weeks. No sign of discomfort after the implantation and no body weight loss were observed before the explantation. After 4 weeks, mice were euthanized by $CO_2$ asphyxiation. The hydrogel samples together with the surrounding tissue were excised by cutting around the area with scissors and scalpels. The explanted samples were then fixed in 10 wt % formalin overnight and embedded in paraffin wax. For each implant, 6-μm sections were cut and mounted onto slides for histological staining. The inflammatory response was examined by staining with hematoxylin & eosin (H&E). The collagen formation and organization was stained using Masson's trichrome stain.

Chlorination and Titration

The chlorination of N-halamine in hydrogel coatings was performed. First, 10 w.t. % bleach (Clorox) was prepared and the pH was adjusted to 7.0 using HCl (6 M). The samples were then immersed in the bleach solution for 1 h, thoroughly washed with deionized (DI) water and dried in a hood overnight to remove any free chlorines. To determine the oxidative chlorine content, a thiosulfate titration method was used. Briefly, two pieces of samples (1 inch each) were put into a cylinder containing 200 mg of KI, 20 mL of DI water and 3 drops of 6 M HCl. The solution then turned blue in color after a starch solution (0.5%) was added. After reacting for 10 minutes, $Na_2S_2O_3$ solution (0.001 N) was used as the titrant and the volume was consumed to turn the color from blue to colorless was recorded. The oxidative chlorine content [$Cl^+$] (atoms/$cm^2$) was calculated based on the following equation: [$Cl^+$] (atoms/$cm^2$)=C×V/2A, where C (mol/L) is the concentration of titrant, V (mL) is the volume of titrant consumed and A is the total area of samples ($cm^2$).

Bacteria Culture and Anti-Bacteria Test

For anti-bacteria tests, a gram-positive strain of *S. aureus* and the gram-negative strain *E. coli* strain O157:H7 were cultured in brain-heart infusion (BHI) buffer for 16 h at 37° C. with 120 rpm rotation. The bacteria were then washed twice with Butterfield's phosphate buffer (BPB) and adjusted to ~$10^6$ colony forming units (CFU) in either PB buffer or LB medium for the following tests. A "sandwich" testing method was used for anti-bacteria test. Briefly, 25 μL of bacterial suspension was inoculated in the center of a 1 $inch^2$PDMS sample. An identical sample was put on the top and a sterile weight was added to ensure full contact. After contact for 10, 30, or 60 minutes, the samples were placed into 5 mL of $Na_2S_2O_3$ solution (0.05 N) to quench all oxidative chlorines on the surface. All samples were vortexed for 2 minutes to detach all survived bacteria from surface into solution. Then, the solution was serially diluted, plated on trypticase soy agar (TSA) plates, and incubated at 37° C. for 24 h. The CFU on the plate was recorded and the number of culturable surviving bacteria was calculated accordingly. Anti-bacterial efficacy was evaluated by comparing the bacterial reduction of control and coated samples. At a fixed time point, a higher log CFU reduction indicated higher antibacterial efficacy.

Dynamic Biofilm Formation Test

A dynamic biofilm formation test was performed. Briefly, a three-chamber parallel flow system was used to evaluate biofilm formation on hydrogel coated catheters. All glassware was sterilized by autoclaving before use. Each glass chamber (φ 1.5 cm*15 cm) contained six 0.5-inch-long sample segments of each type: Uncoated catheter, AASgel coated catheter, and AASHgel coated catheter. The bacterial suspension was first continuously flowed at 1.5 mL/min through each chamber for three hours for initial bacterial attachment. After three hours, sterile LB medium was flowed through all three parallel chambers by pumps at 1.5 mL/min. The medium flow washed away unattached bacteria and provided nutrients for the attached ones. After 24, 48, and 72 hours of medium flow, two samples were taken out of each chamber and rinsed with sterile PBS. One sample of each type was stained with LIVE/DEAD BacLight bacterial viability kit (Invitrogen) for observation. Images were captured by florescence microscopy (Olympus FV1000). The other sample of each type collected was vortexed for two minutes to detach all surviving bacteria from surface into solution. The solution was then serially diluted and plated on Trypticase soy agar (TSA) plates and incubated at 37° C. for 24 h. The CFU on the plate was recorded and the number of culturable surviving bacteria was calculated. Anti-bacterial efficacy was evaluated by comparing the bacterial reduction of control and modified samples: at a fixed time point, a higher log CFU reduction indicated higher antibacterial efficacy.

Simulation and Statistical Analysis

Differential equations were solved and the solution was plotted in 3D mesh format using Matlab 2017b and Comsol Multiphysics 4.3a. Details are included as notes in Supporting Information.

Data were reported as the average±s.e.m. Statistical significance was analyzed using one-way ANOVA with a Tukey HSD post-hoc test. (*: p<0.1, : p<0.05, *: p<0.01).

Model Overview

Figure 16:
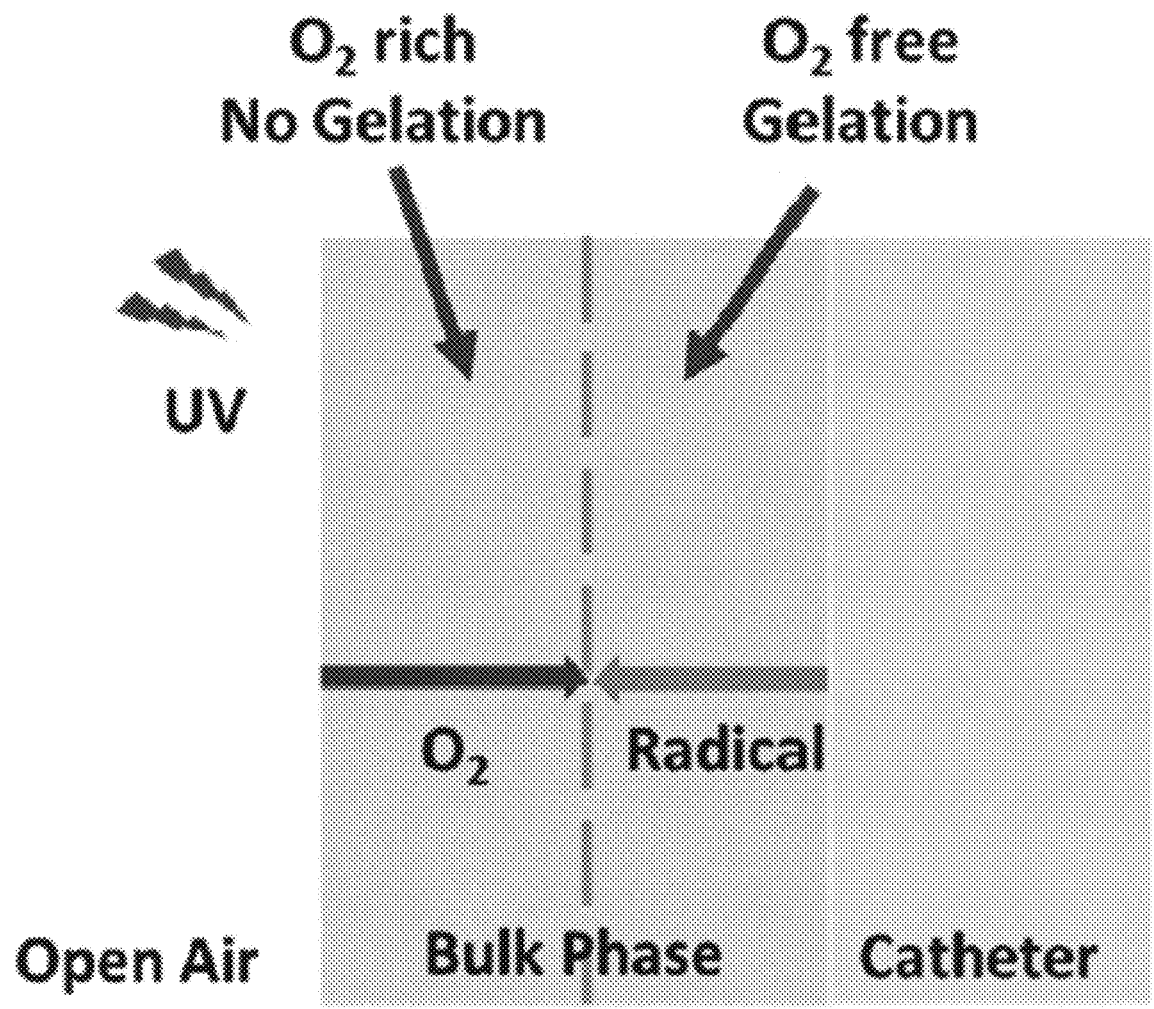
FIG. 16 is a schematic representation of a physical model for counter-diffusion of oxygen and radicals.

Oxygen is well-known for consuming radicals and hence inhibiting photopolymerization and cross-linking of polymers until dissolved oxygen is consumed to a minimal level. When exposed to air, oxygen constantly diffuses into the hydrogel from the air-hydrogel interface, and reacts with radicals at a constant k. Here, the catheter was pre-treated with benzophenone which can provide radicals that react with oxygen and enable cross-linking. Therefore radicals diffused into the bulk phase at the opposite direction of oxygen, enabling a small area to be oxygen free, and allowed gelation. This process is shown in FIG. 16, which is a schematic representation of a physical model for counter-diffusion of oxygen and radicals.

Governing Equations

Due to the low concentration of oxygen and radicals in water, Fick's law was used to calculate the counter diffusion. The equations are as follows:

$$\frac{d[O_2]}{dt} = \frac{D_{O2}}{r} \cdot \frac{d}{dr}\left(r\frac{d[O_2]}{dr}\right) - k[O_2][R] \quad (1)$$

$$\frac{d[R]}{dt} = \frac{D_R}{r} \cdot \frac{d}{dr}\left(r\frac{d[R]}{dr}\right) - k[O_2][R] + r_d \quad (2)$$

where the $D_{O2}$ and $D_R$ are the diffusion constant for oxygen and radicals, respectively. Radius r is the diameter on the catheter, k is the reaction coefficient of the radical quenching reaction, $r_d$ is the decomposition rate for initiators during photopolymerization, and [R] and [$O_2$] denotes the concentration of radicals and oxygen, respectively.

Equation (1) and (2) are transformed into following difference equations and solved:

$$\frac{\Delta[O_2]_i}{\Delta t} = D \cdot \left(\frac{[O_2]_{i-1} + [O_2]_{i+1} - 2[O_2]_i}{2\Delta r^2} + \frac{[O_2]_{i+1} - [O_2]_{i-1}}{2r \cdot \Delta r}\right) - k \cdot [O_2]_i \cdot [R]_i \quad (3)$$

$$\frac{\Delta[R]_i}{\Delta t} = D \cdot \left(\frac{[R]_{i-1} + [R]_{i+1} - 2[R]_i}{2\Delta r^2} + \frac{[R]_{i+1} - [R]_{i-1}}{2r \cdot \Delta r}\right) - k \cdot [O_2]_i \cdot [R]_i + rd \quad (4)$$

The distribution of chemicals at certain timepoints are solved using:

$$[O_2]_{i,t+1} = [O_2]_{i,t} + \Delta[O_2]_{i,t} \quad (5)$$

$$[R]_{i,t+1} = [R]_{i,t} + \Delta[R]_{1,t}| \quad (6)$$

Boundary and Initial Conditions

The boundary conditions at the interface represent known values for some physical quantities at the edge of a spatial mesh, in which integration of the differential equations is performed. At the contacts, the boundary conditions reflect the concentration or flux of oxygen or radical molecules. Four independent differential equations correspond to the concentration or flux of radicals and oxygen, two on each interface contacts. On the air-hydrogel interface, the oxygen boundary condition corresponds to the dissolution of oxygen into the hydrogel. No flux should exist with radicals on this interface. On the hydrogel-catheter interface, the boundary condition corresponds to saturated radical concentration on the catheter surface, while the benzophenone on the catheter should inhibit all oxygen at the point of contact. Thus the boundary conditions are as follows:

Air-hydrogel interface:

$$N_{O_2} = k_L([O_2^g] - [O_2])$$
$$\frac{d[R]}{dr} = 0$$

Hydrogel-catheter interface:

$$[O_2] = 0$$

[R]=saturate benzophenone concentration (Assume all dissolved benzophenone were initiated to provide radicals)

Assumptions and Parameters

The initial conditions are set as follows:

| Parameters | | |
|---|---|---|
| k | 1.50E+06 | L/mol · s |
| $D_{O2}$ | 2.50E+03 | µm²/s |
| $D_R$ | 5.00E+02 | µm²/s |
| $[O_2^\theta]_{air-hydrogel}$ | 2.50E−04 | mol/L |
| $[O_2]_{initial-hydrogel}$ | 2.10E−04 | mol/L |
| $[O_2]_{hydrogel-catheter}$ | 0 | mol/L |
| $[R]_{hydrogel-catheter}$ | 7.52E−04 | mol/L |
| $[R]_{initial-hydrogel}$ | 0 | mol/L |
| $r_{catheter}$ | 2667 | µm |
| $r_d$ | 1.00E−7 | mol/L/s |
| Oxygen $k_L$ | 1.58E−04 | m/s |

Numerical Solution

The simulation process was run with either Matlab and Comsol Multiphysics. Both software yielded similar numerical solutions. The diffusion of radicals and oxygen nearly reached steady state after 90 seconds, and would reach full steady state within 300 seconds. The hydrogel was divided into 2 parts: one was radical free and the other was oxygen free. Sensitivity tests were carried out with the assumptions on the decomposition rate of radicals under UV ($r_d$) as well as the air-hydrogel interface mass transfer coefficient of oxygen ($k_L$). This modeling result was consistent with the gradient cross-linking degree observed, with maximum being reached at the adjacent region of the catheter and decreasing with the increase of the gel thickness Sensitivity Analysis Sensitivity analysis is carried out for assumptions made on radical decomposition rate $r_d$ in equation (2) and oxygen transfer coefficient $k_L a$ at air-hydrogel boundary. Both these parameters are expected to influence the thickness of the radical-rich division.

Sensitivity on Radical Decomposition Rate Rd

Figure 8:
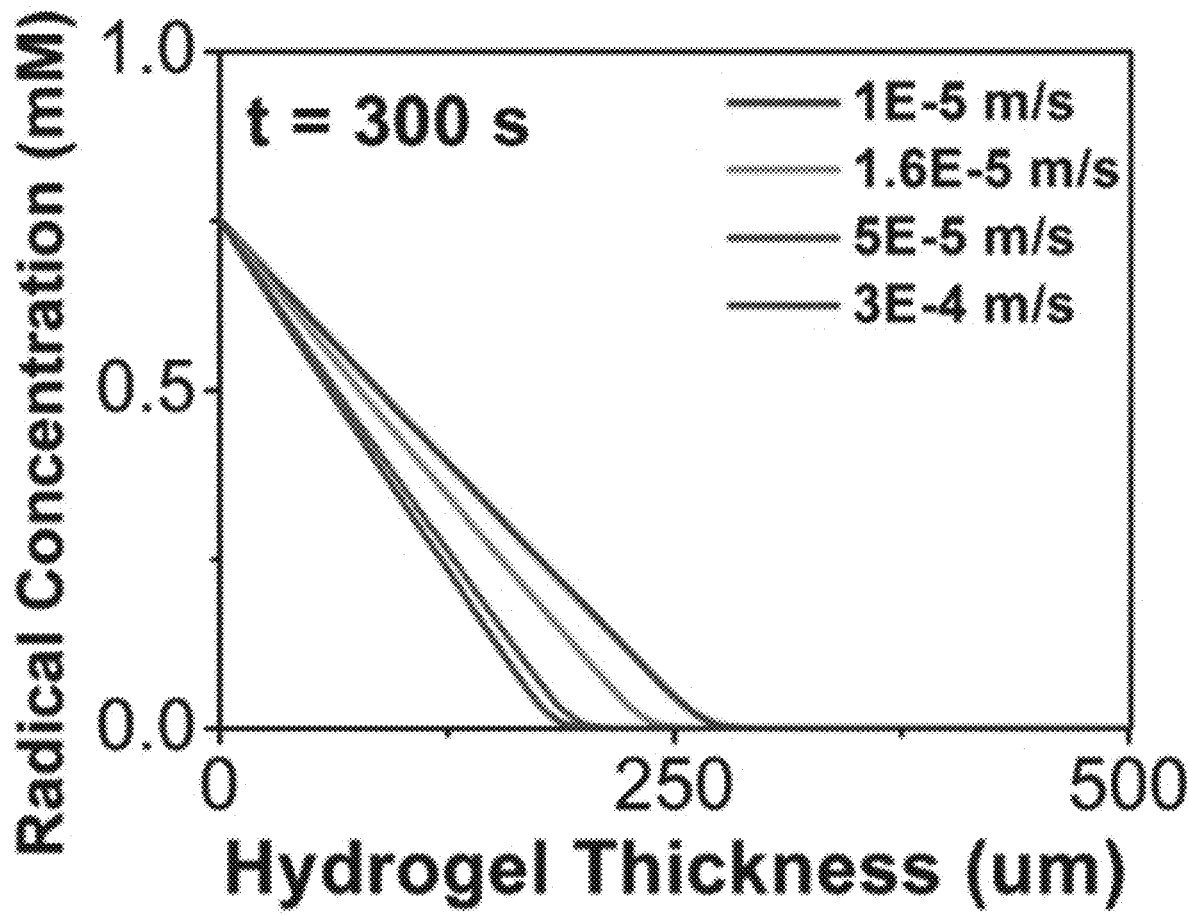
FIG. 8 is a graphical representation showing the sensitivity of the oxygen transfer coefficient kL to the distribution of radicals in a hydrogel as described here.
Figure 9:
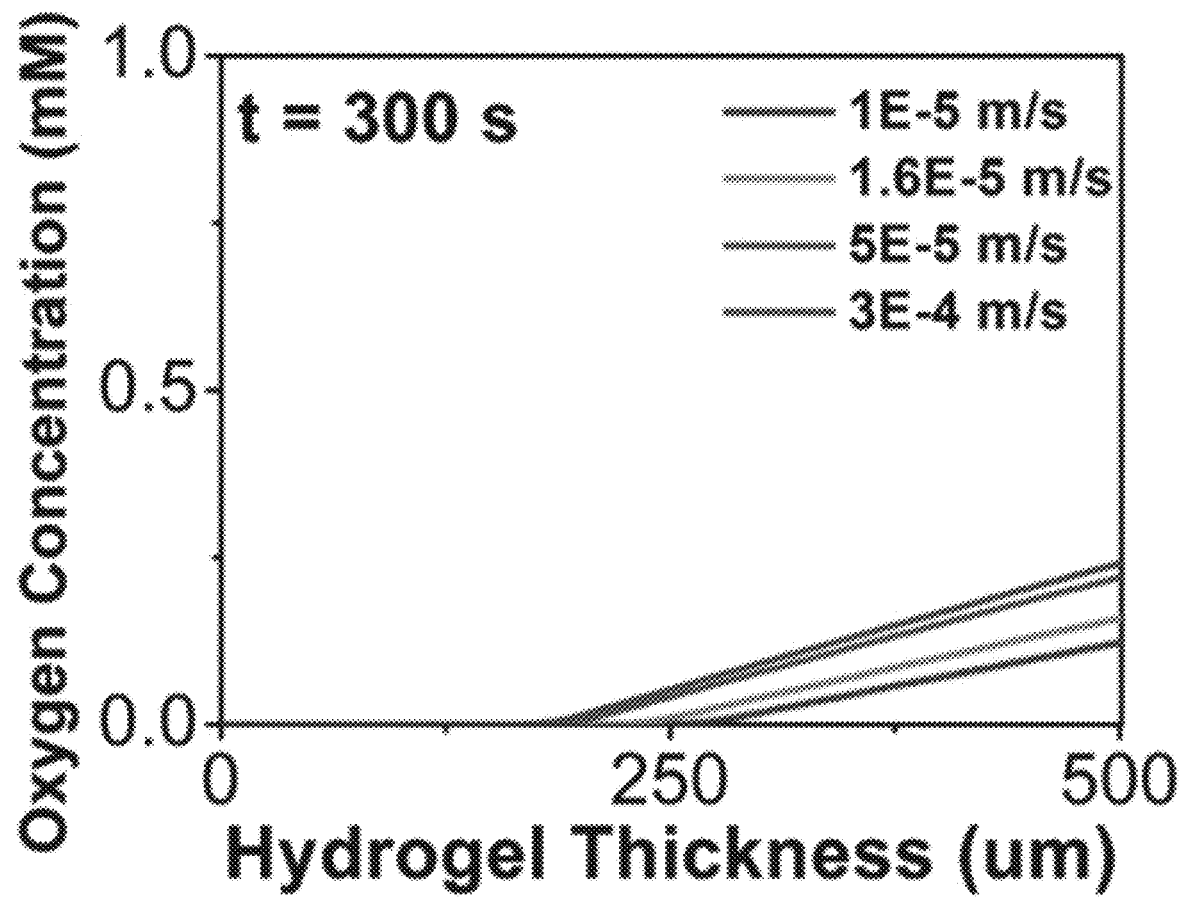
FIG. 9 is a graphical representation showing the sensitivity of the oxygen transfer coefficient kL to the distribution of oxygen in a hydrogel as described here.

The concentration of Iragcure 2959, the initiator added into pre-gel solution for UV cross-linking was 0.034M. The radical decomposition coefficient only correlates to the UV light intensity. Based on the reaction coefficient of $10^{-8}$~$10^{-6}$ per second, the reaction rate is assumed to be around $3\times10^{-8}$ to $3\times10^{-6}$ M/s. A sensitivity test for $r_d$ from $1\times10^{-8}$ to $5\times10^{-6}$ M/s was carried out. The results are shown in FIG. 8 and FIG. 9. FIG. 8 shows the sensitivity of the oxygen transfer coefficient $k_L$ to the distribution of radicals in the hydrogel after 300 seconds of cross-linking. FIG. 9 shows the sensitivity of the oxygen transfer coefficient $k_L$ to the distribution of oxygen in the hydrogel after 300 seconds of cross-linking. The difference on the radical decomposition rate only caused minor changes to the simulation results.

Sensitivity on Oxygen kL

Figure 10:
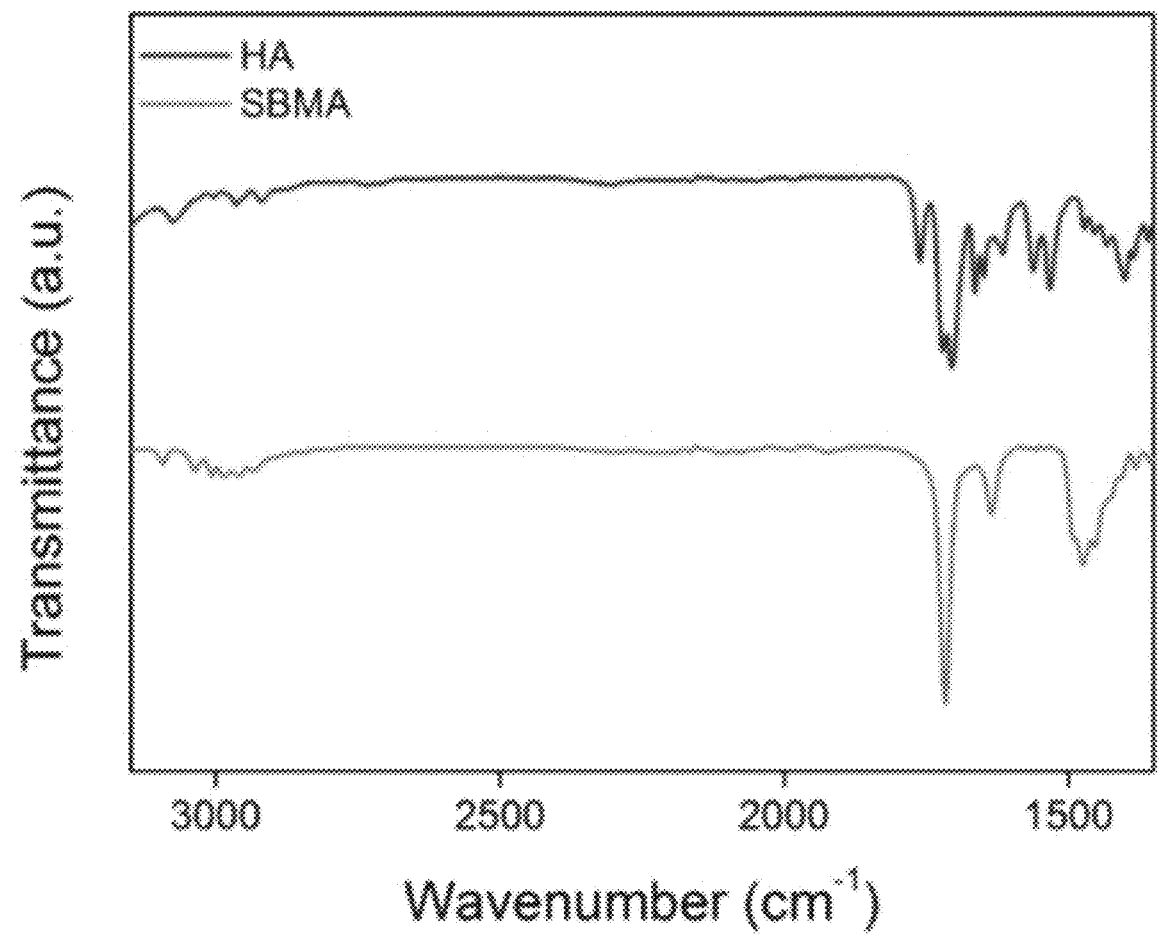
FIG. 10 shows FT-IR spectra results for N-halamine and sulfobetaine monomers in a conformal hydrogel as described here.

Oxygen was expected to constantly diffuse into hydrogel during cross-linking from the hydrogel-air interface. It was assumed that the diffusion parameter of oxygen into hydrogel was similar to that of oxygen into water, which was reported to be around 0.02~0.1 per second for the parameter $k_L a$ depending on the oxygen transfer environment. The "a", which refers to the specific surface area of column, equals to 2/r which is 0.632 mm. Thus, the possible phase transfer coefficient $k_L$ range expected should be around $1.58\times10^{-5}$ to $3.2\times10^{-4}$ m/s. The sensitivity test was carried out with $k_L$ from $1\times10^{-5}$ to $3\times10^{-4}$ m/s. As shown in FIG. 10, a lower oxygen transfer coefficient would decrease total oxygen transfer into hydrogel, leading to around 50 µm fluctuation for the thickness of the radical-rich part, which was also a minor change. $1.58\times10^{-4}$ m/s was chosen as the $k_L$ regarding to a commonly used transfer coefficient for oxygen form air into water. FIG. 10 shows FT-IR spectra results for N-halamine (HA, top) and sulfobetaine (SBMA, bottom) monomers.

The SGS coating method is schematically illustrated in FIG. 1A. A catheter or silicone tubing was first treated with benzophenone, to provide free radical groups on the surface, followed by dip-coating with an AAm pre-gel solution at 45° C. The solution formed a weak but conformal layer of hydrogel on the tubing at room temperature. The surface functionalized catheter or tubing was then exposed to UV light to form a robust coating layer. The photocurable formulation was exposed to UV light while open to air, and oxygen inhibition of the radical polymerization at the surface created a gradient of crosslinking with depth. The loosely attached hydrogel swelled and fell off when immersed in water, leaving a mostly uniform ~30 µm thick hydrogel layer on the catheter surface. This coating method is applicable to elastomer substrates with irregular shapes or high curvatures, which would otherwise be difficult to coat due to the de-wetting on curved surfaces. In total, four different hydrogels were prepared and coated on catheters or medical grade silicone tubings, including AAm-Agar (AAgel), AAm-Agar-SBMA (AASgel), AAm-Agar-HA (AAHgel), and AAm-Agar-SBMA-HA (AASHgel). The concentrations of the monomers in each hydrogel coating are listed in Table 1.

Figure 1B:
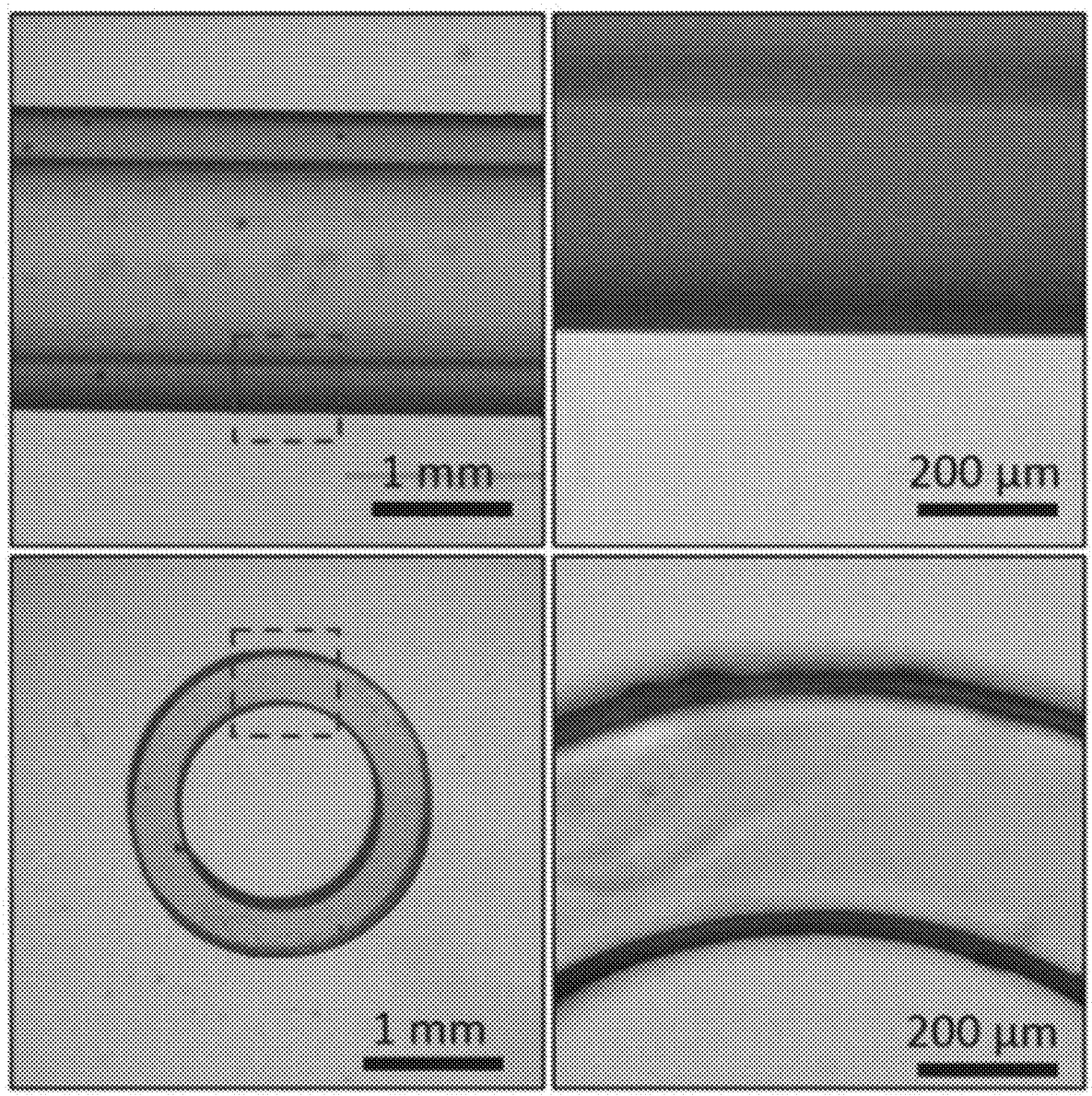
Figure 1C:
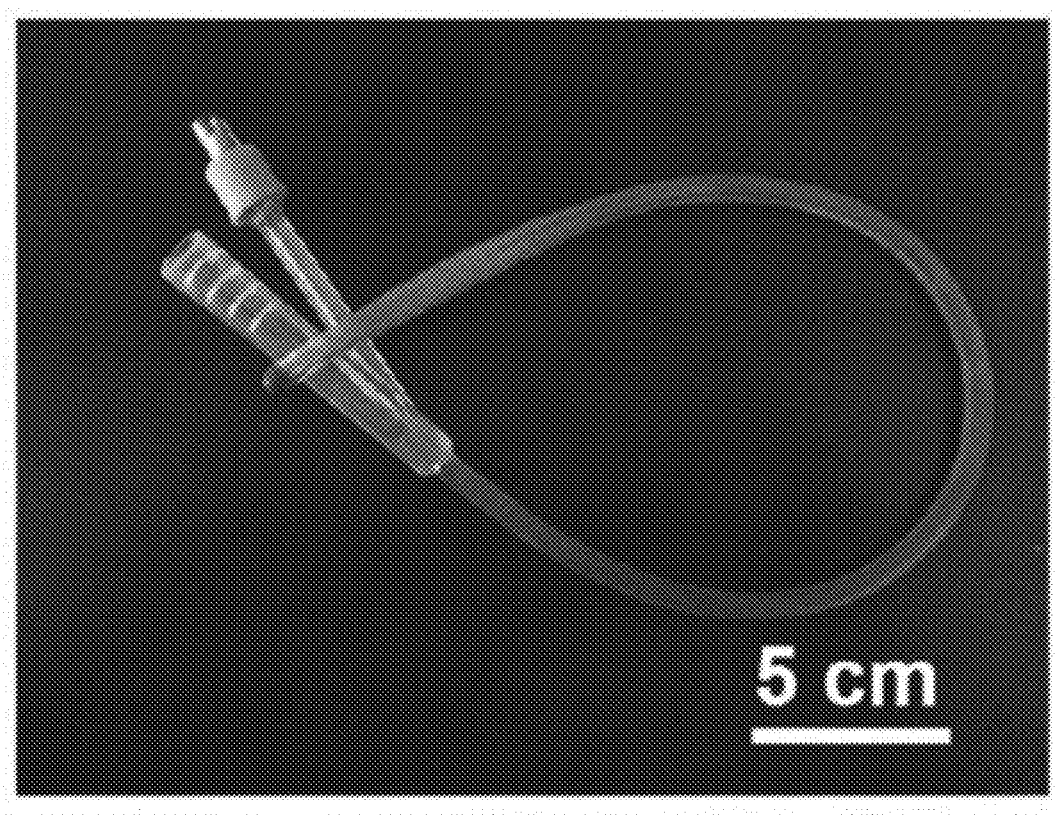
Figure 1D:
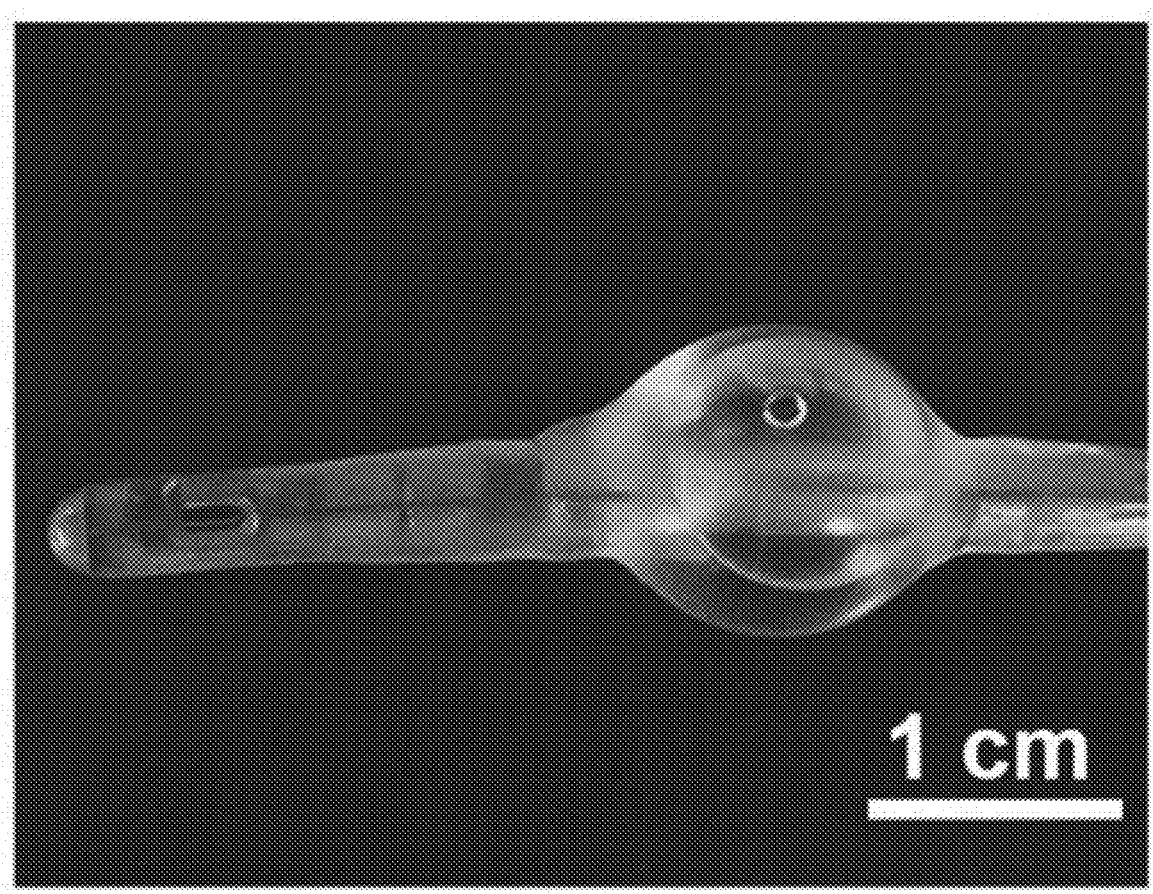
Figure 1E:
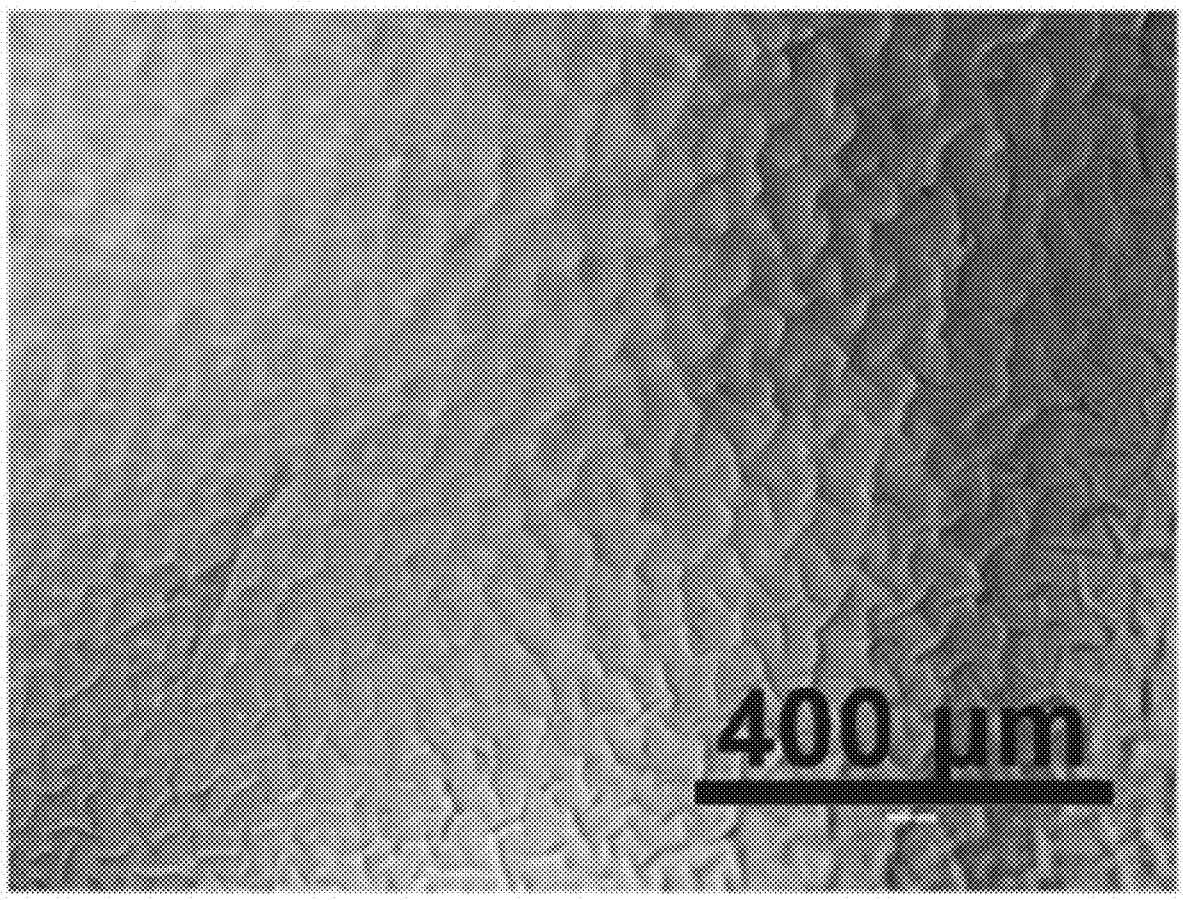
Figure 1F:
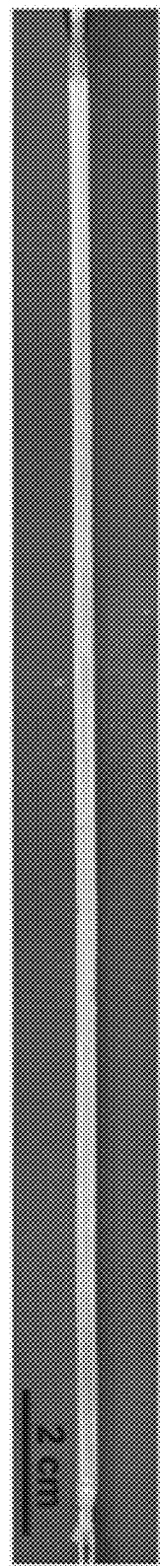
Figure 6A:
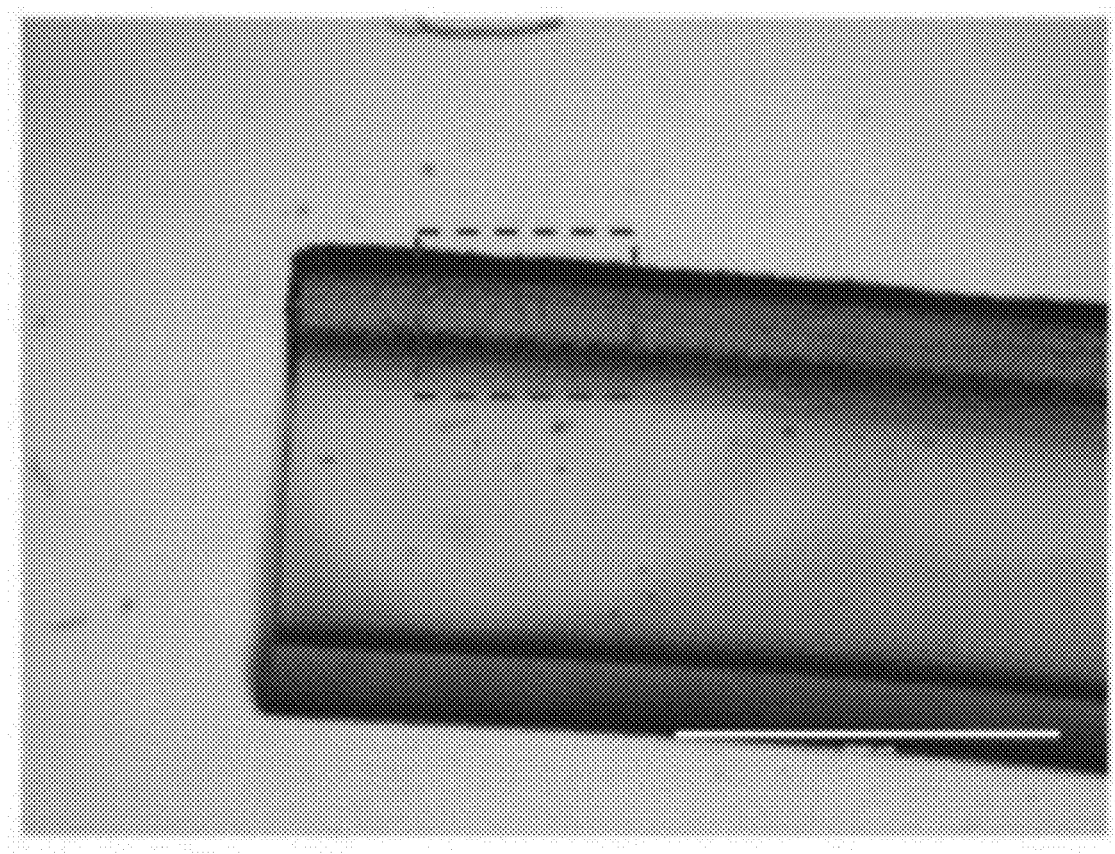
FIG. 6A shows a microscopic image of a hydrogel layer on a tubing surface.
Figure 6B:
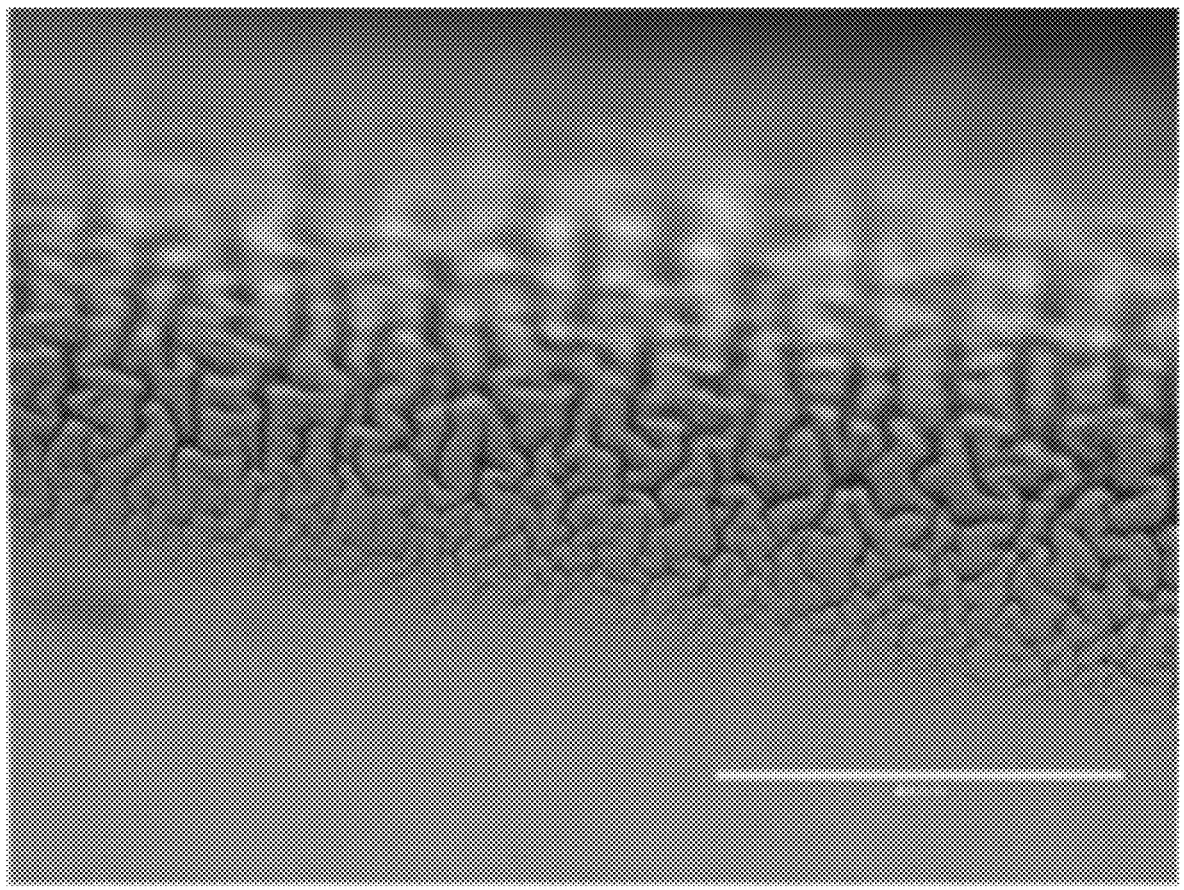
FIG. 6B shows a magnified image of the swollen hydrogel layer on the tubing surface of FIG. 6A.

The coated silicone tubing was observed under a fluorescence microscope with hydrogel layer stained with FITC-dextran. A ~30 µm thick layer of AASgel was coated on both the outside and inside of the silicone tubing (FIG. 1B). This hydrogel was also coated (stained with a red food dye) on a 16-inch-long catheter (FIG. 1C), proving the scalability of the method. The hydrogel coating (stained with a red food dye) remained relatively uniform and attached to the balloon as it was inflated (FIG. 1D). The hydrogel coating on the catheter was observed under a microscope. The self-wrinkled pattern on the catheter was a result of swelling of the hydrogel coating (FIG. 1E). In addition, a 10-inch-long medical grade silicone tubing was coated (FIG. 1F) and used to measure the water content of the hydrogel coating. A 9% water content was observed in silicone tubing coated with hydrogels, suggesting 70-80% water content in the hydrogel coating. Uncoated substrates did not contain water content. This also proved the existence of the hydrogel layer on the tubing surface. (FIG. 6A and FIG. 6B). Although the hydrogel coating was thin and mostly uniform, thickness variation (e.g. FIG. 1B) was sometimes observed. The uniformity may be improved by controlling the coating process.

Figure 2A:
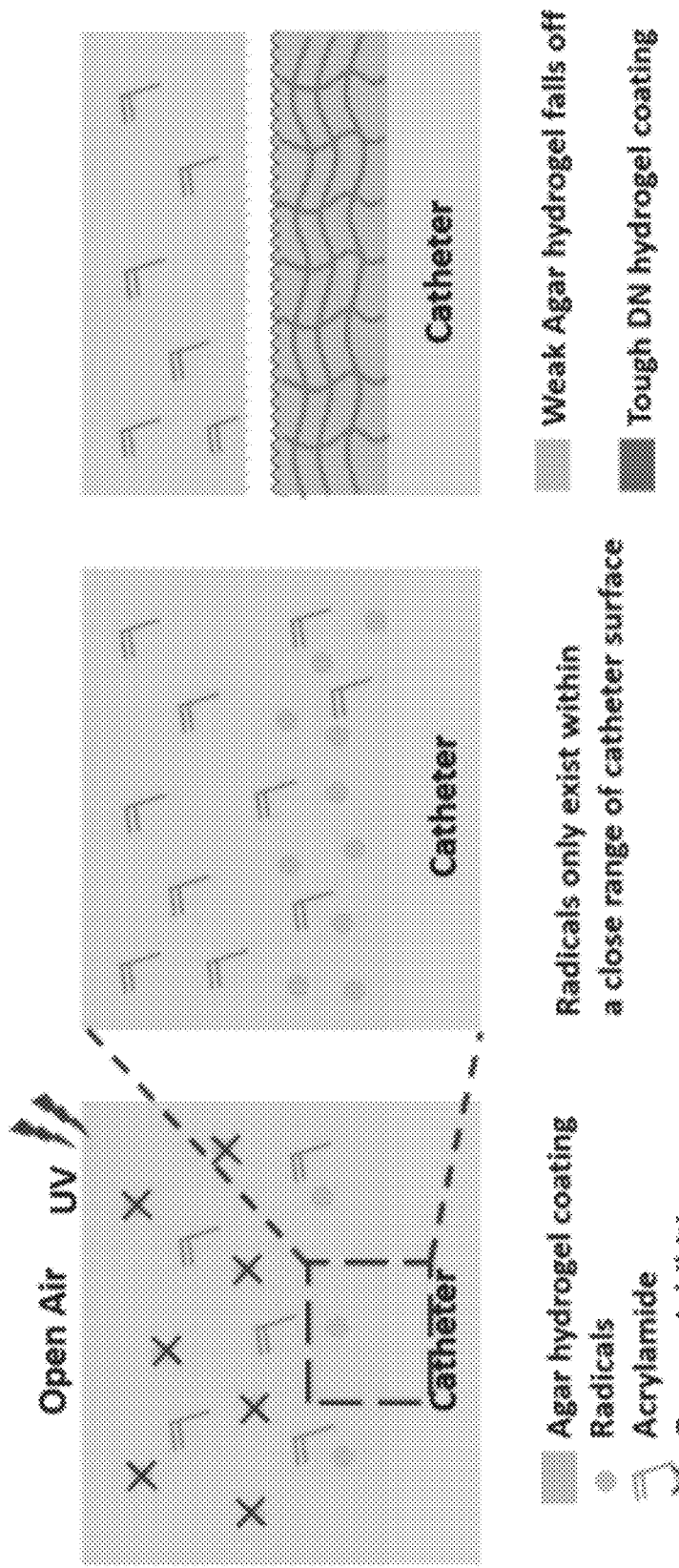
FIGS. 2A-2D are visual representations of the cross-linking of the hydrogel coating of the present application.

To better understand the swelling and falling-off behavior of hydrogel coatings after UV treatment, studied the gradient of cross-linking density by UV cross-linking in open air was studied. When exposed to air, oxygen constantly diffuses into the hydrogel from the air-hydrogel interface, and quenches radicals; only the region near the catheter surface has sufficient radicals and crosslinking to form a tough hydrogel (FIG. 2A). Below is a proposed reaction model describing this UV-induced cross-linking process. It was assumed that oxygen from open air and radicals from the catheter's surface are constantly diffusing into the agar hydrogel (ring cylinder shape) from opposite directions under the dominance of Fick's law, thus giving:

$$\frac{d[O_2]}{dt} = \frac{D_{O2}}{r} \cdot \frac{d}{dr}\left(r\frac{d[O_2]}{dr}\right) - k[O_2][R] \quad (1)$$

$$\frac{d[R]}{dt} = \frac{D_R}{r} \cdot \frac{d}{dr}\left(r\frac{d[R]}{dr}\right) - k[O_2][R] + r_d \quad (2)$$

where $D_{O2}$ and $D_R$ stands for the diffusion constant of $O_2$ and radicals, respectively; r is the radius from center of the catheter, k is the quenching reaction coefficient, and $r_d$ is the initiator decomposition rate for Irgacure 2959 in the agar hydrogel. This model was run with either Matlab or Comsol Multiphysics; both yielded similar results. Details for getting the numerical solutions of these differential equations are presented below.

Figure 2B:
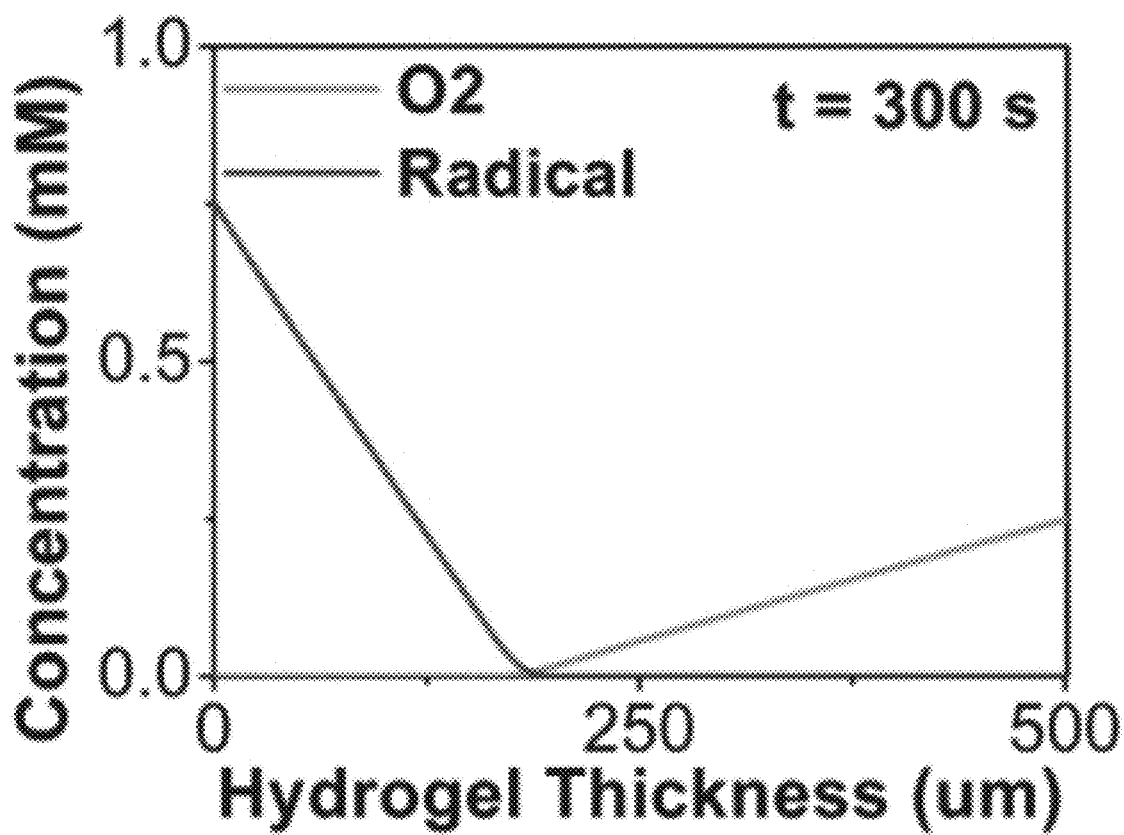
Figure 2C:
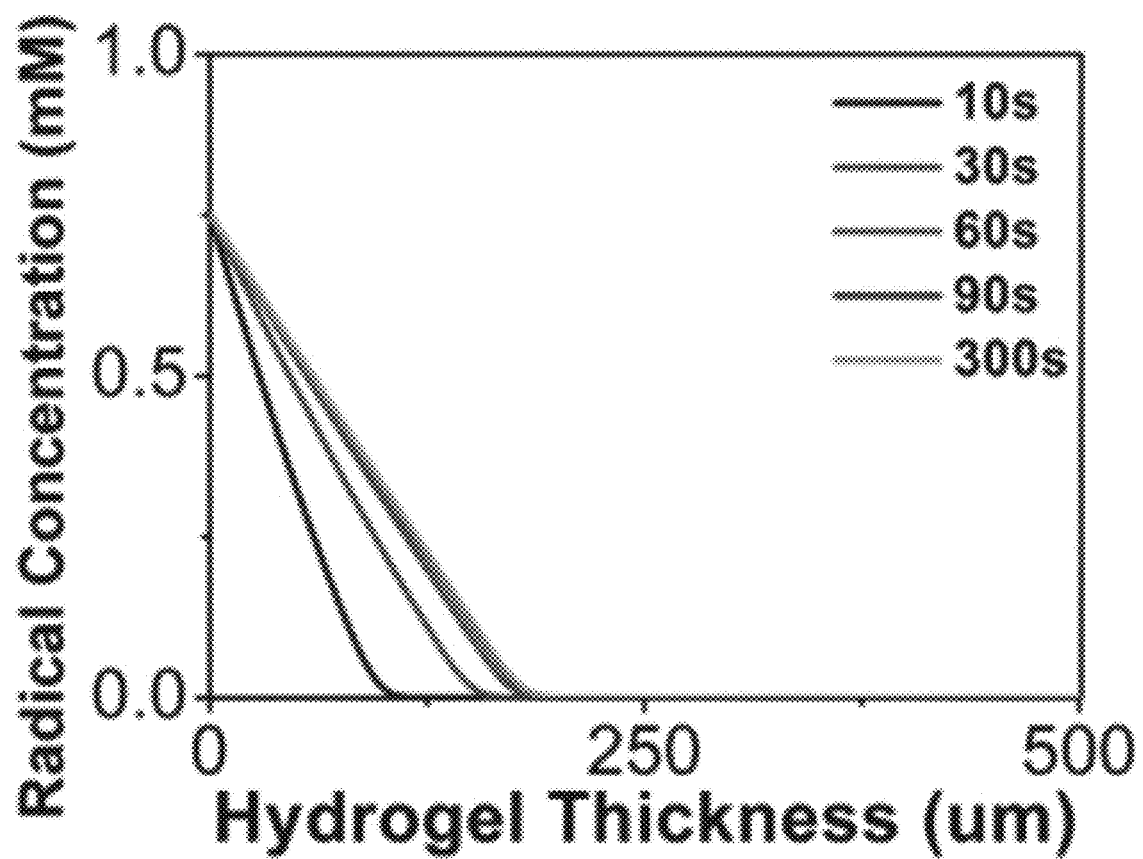
Figure 2D:
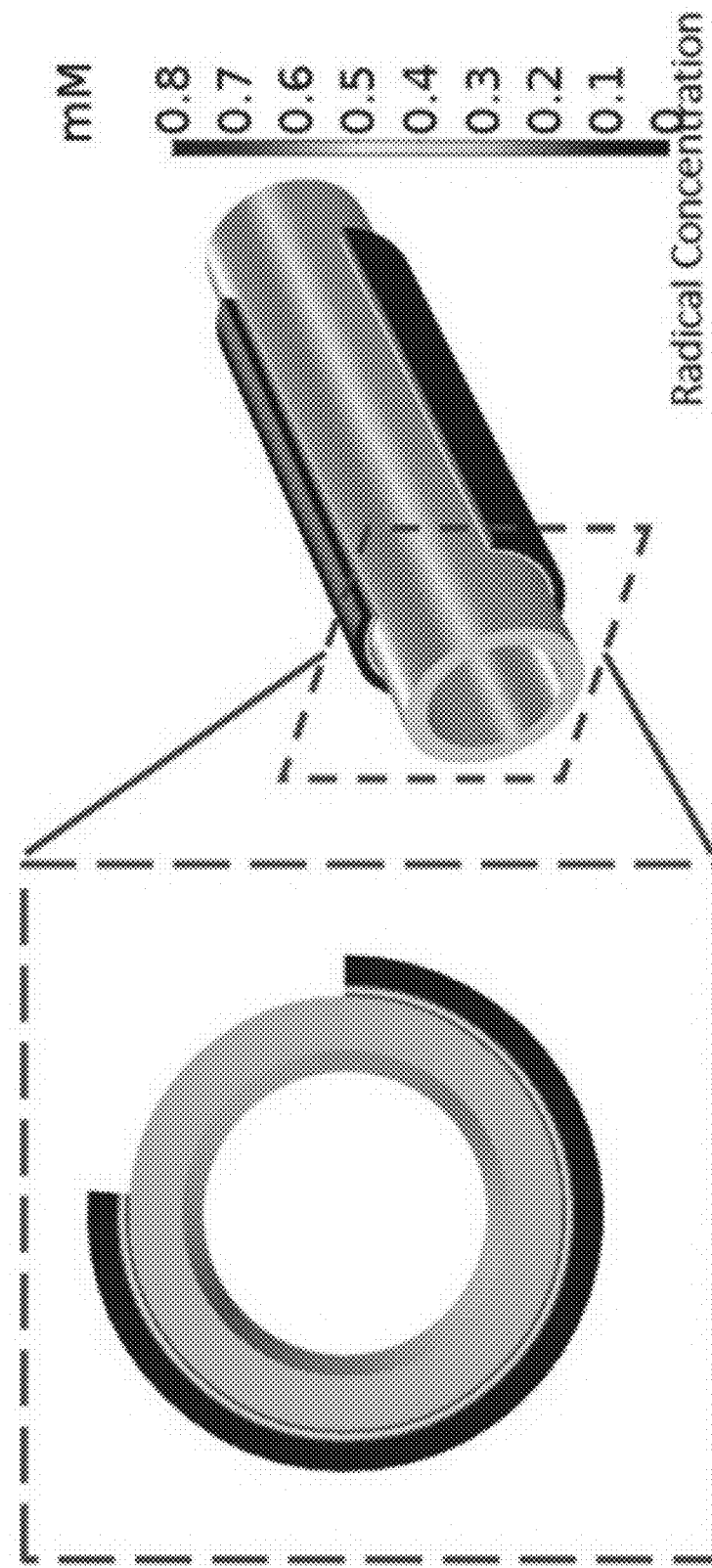
Figure 7:
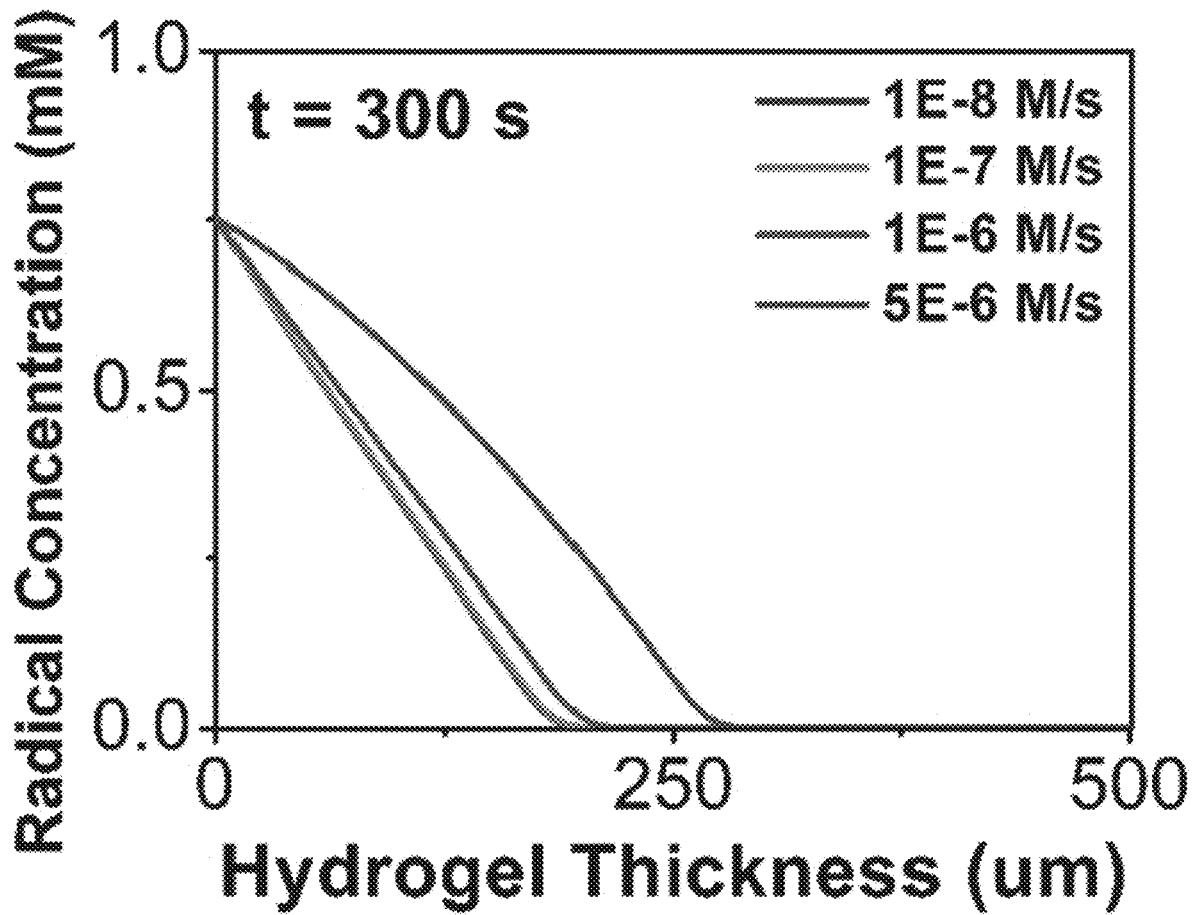
FIG. 7 is a graphical representation showing radical concentration as a function of hydrogel thickness.

For a typical 500-μm-thick initial hydrogel coating, the results suggested that the agar hydrogel was divided into two parts: a radical-rich region near the catheter surface and a radical-free region near the air-hydrogel interface (FIG. 2A and FIG. 2B); and that the diffusion of oxygen and radicals into the hydrogel reached a nearly steady state within 90 s (FIG. 2C). As a result of oxygen quenching, high radical concentration was only observed in a narrow range near the catheter surface. If 0.5 mM was taken as the critical radical concentration for forming the tough hydrogel, the critical thickness would be 30-80 μm. This distribution would show only ~20 μm shift from changes in assumptions on radical decomposition rate of $10^{-8}$-$10^{-6}$ mol/L·s$^{-1}$ or oxygen transfer coefficient (10 of $1\times10^{-5}$-$3\times10^{-4}$ m/s (FIG. 7 and FIG. 8). Therefore, a gradient of cross-linking density was generated, with maximum being reached at the adjacent region of the catheter and decreasing with the increase of the gel thickness (FIG. 2D). The critical thickness can be modulated by the initiator decomposition rate, exposure time, monomer concentration, or total hydrogel thickness.

Figure 3A:
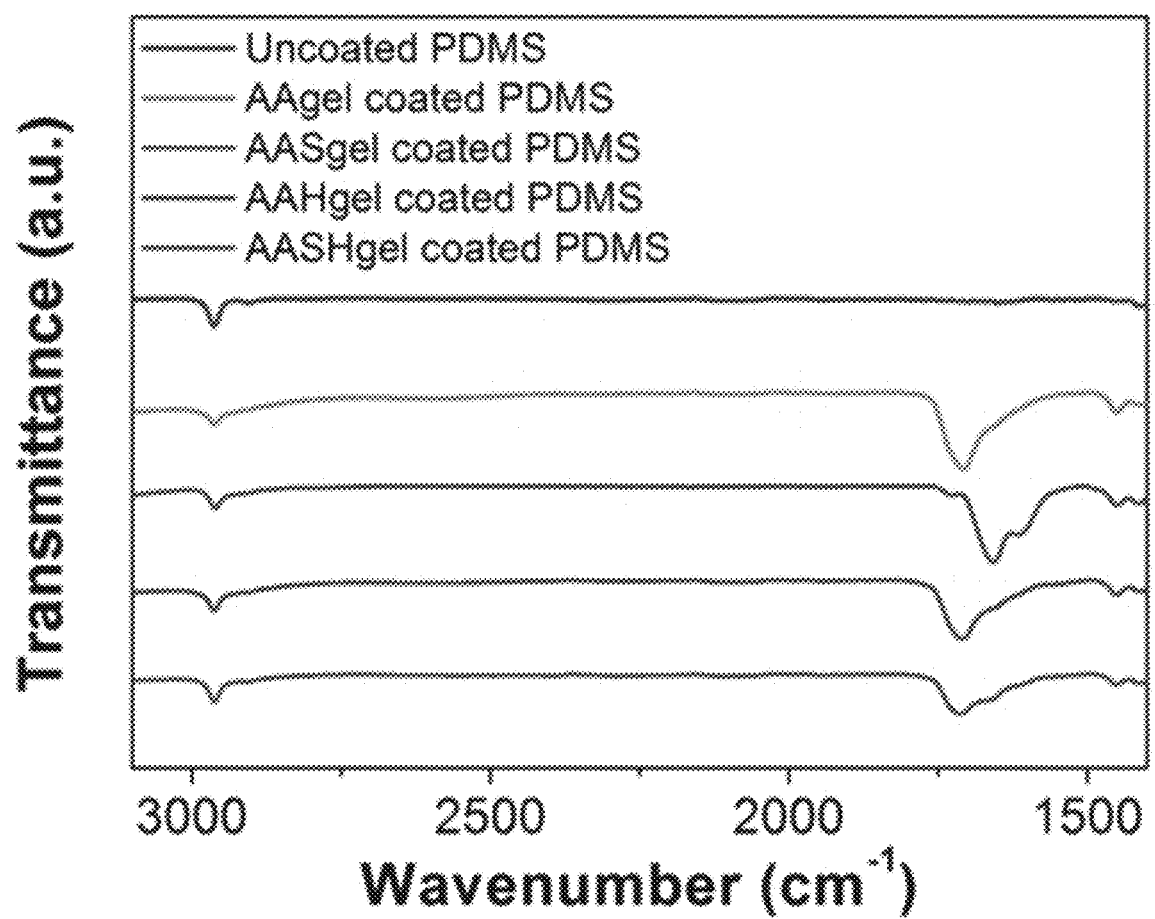
FIGS. 3A-3D show the IR, coefficient of friction and the robustness of the hydrogel coating of the present application.

The composition of the hydrogel coatings were characterized through FT-IR spectra (FIG. 3A). Significant differences between coated and uncoated PDMS at 1700 cm$^{-1}$ were observed; all coated samples showed C=O double bond peaks that were absent in bare PDMS. The existence of sulfobetaine or hydantoin acrylamide in the hydrogel were confirmed by FT-IR spectra at 1600 cm$^{-1}$, as the C=O double bond in hydantoin acrylamide and sulfobetaine were shifted towards lower wavelength. These shifts were also observed in the FT-IR spectrum results of their monomers (FIG. 10). It is also noted that the sulfobetaine peak in AASgel was higher than that in AASHgel due to the higher sulfobetaine content (40 wt % compared to 15 wt %), and partially masked the acrylamide peak after data normalization, leading to a further shift to the lower wavelength.

Figure 3B:
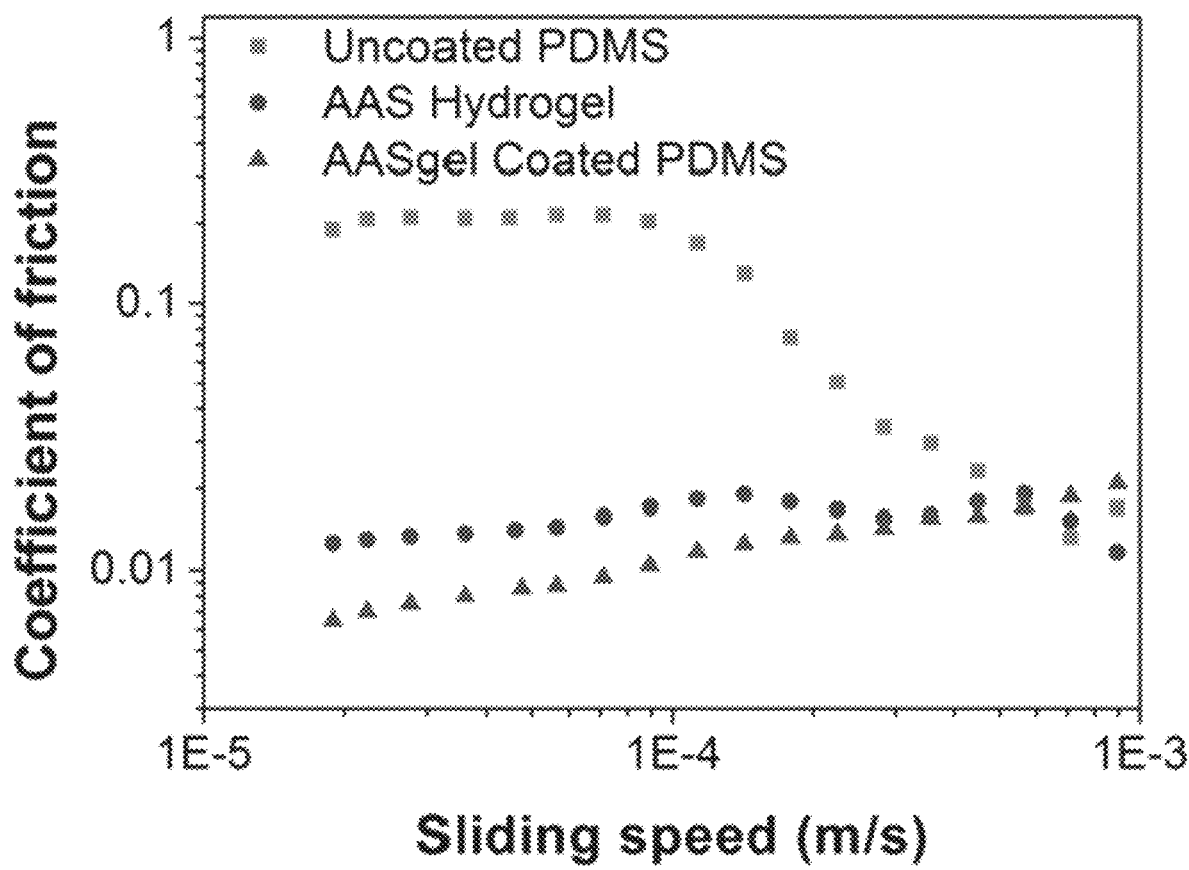
Figure 3C:
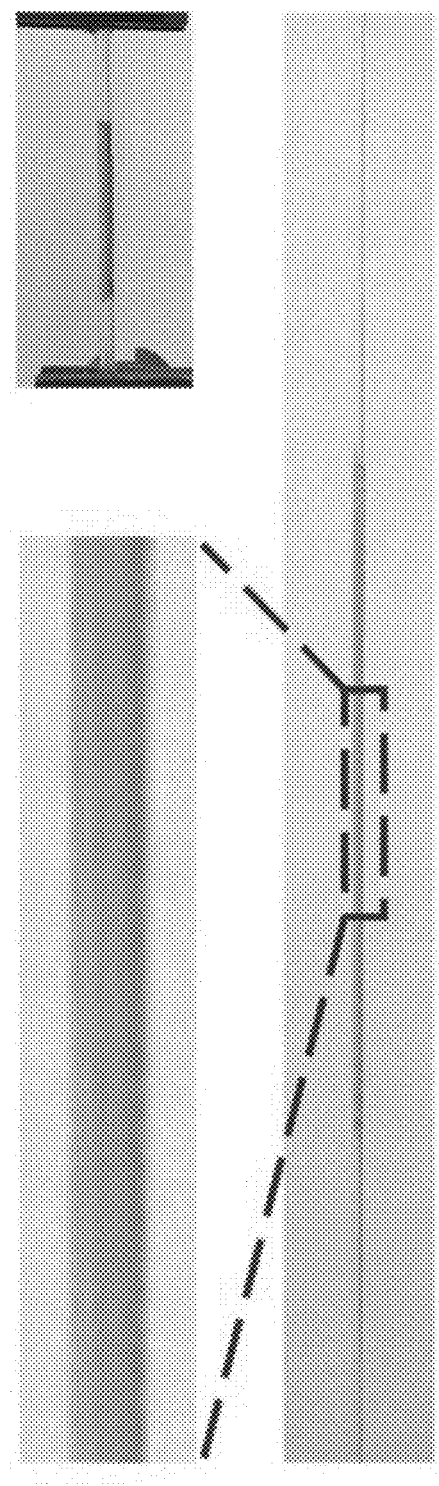
Figure 3D:
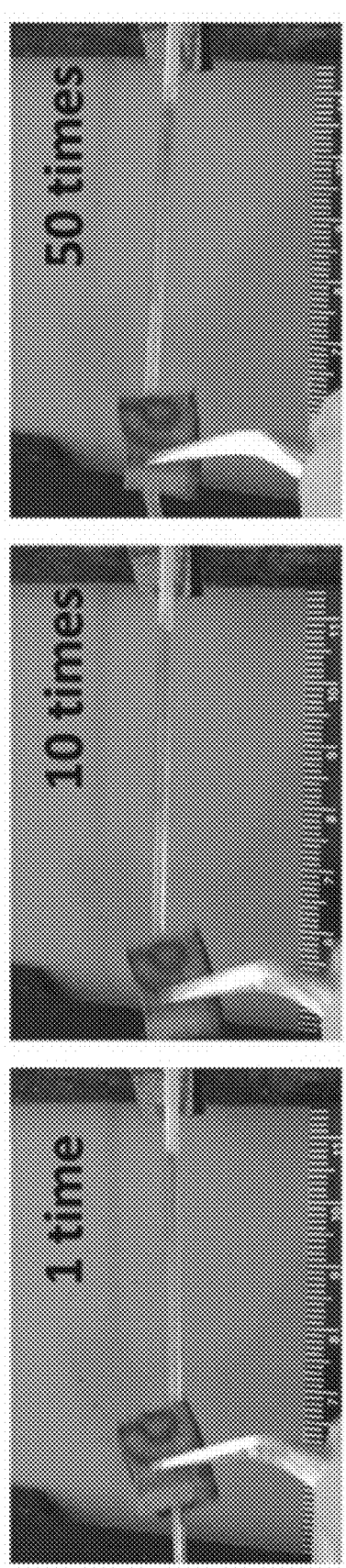
Figure 11A:
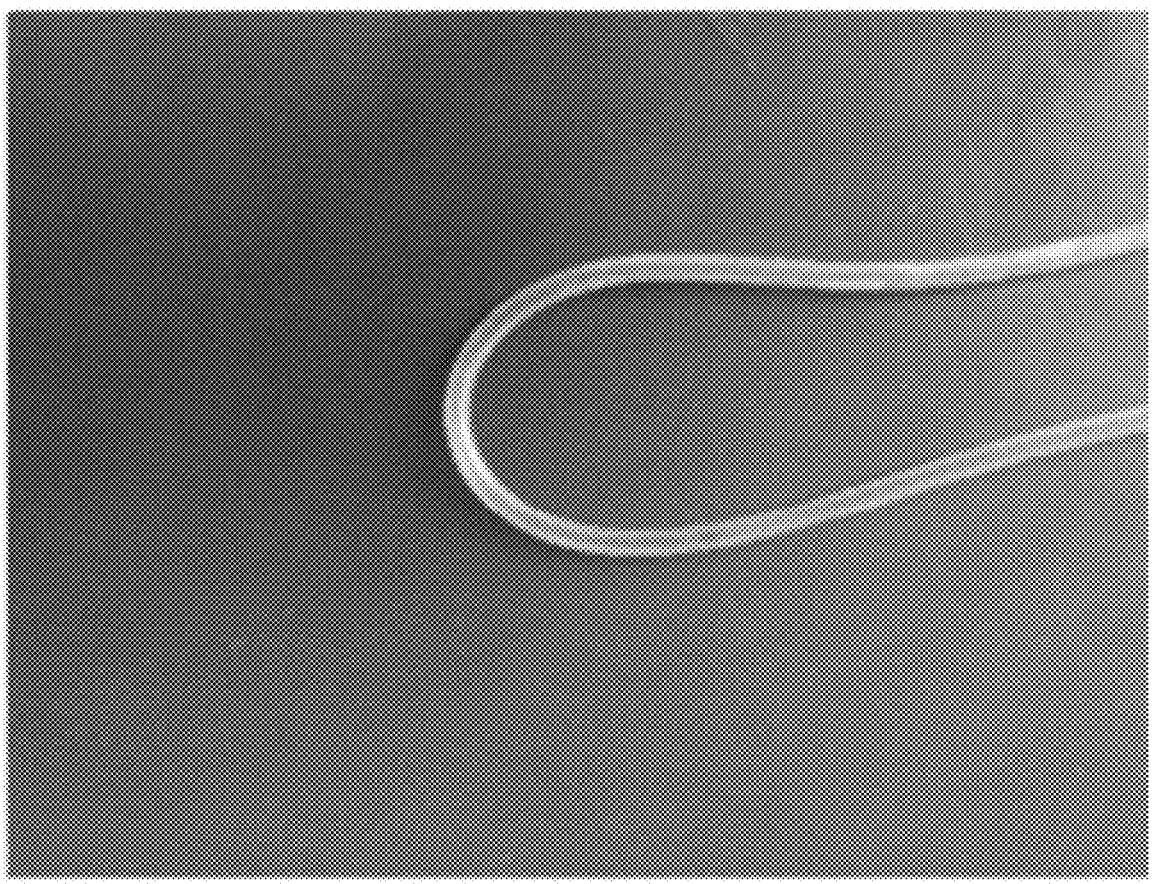
FIGS. 11A-11B are images of the hydrogel of the present application coated onto a tube.
Figure 11B:
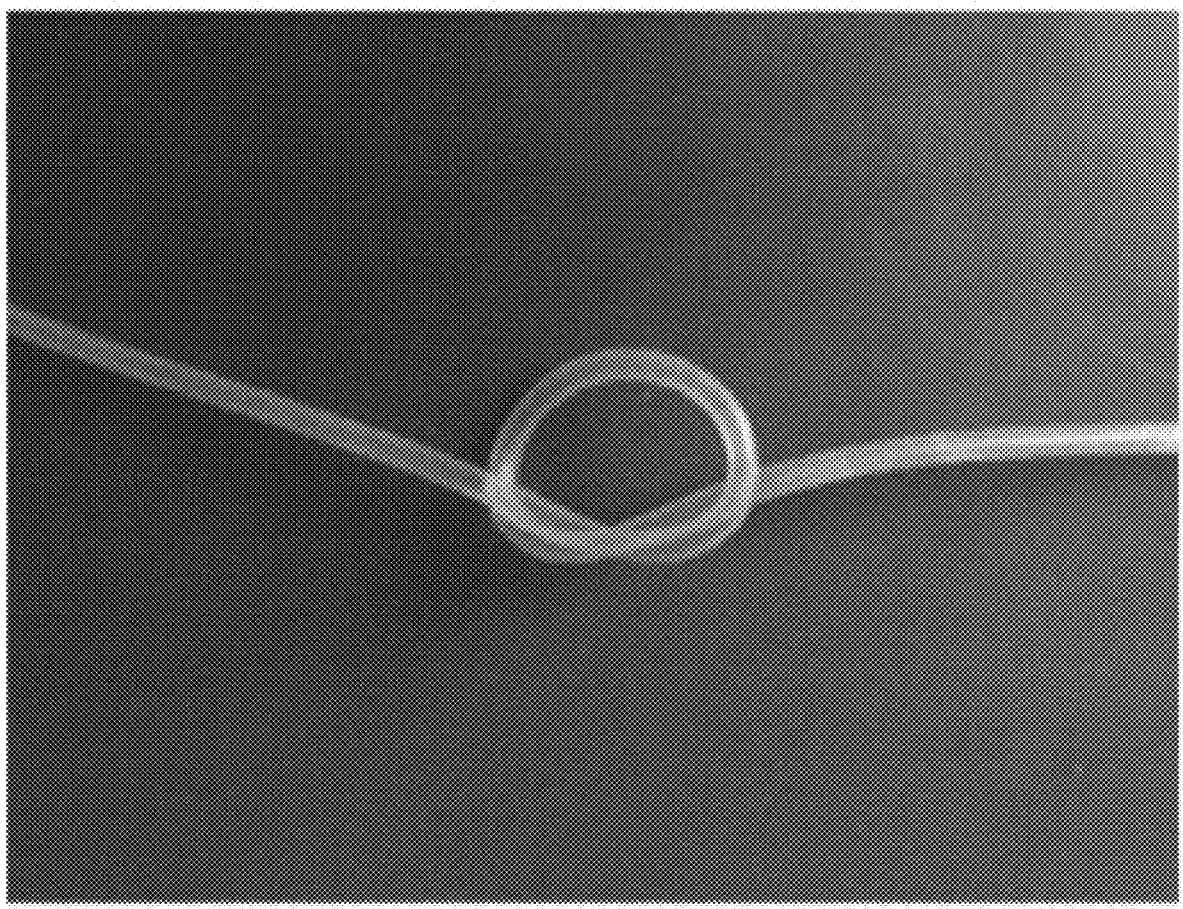
Figure 12:
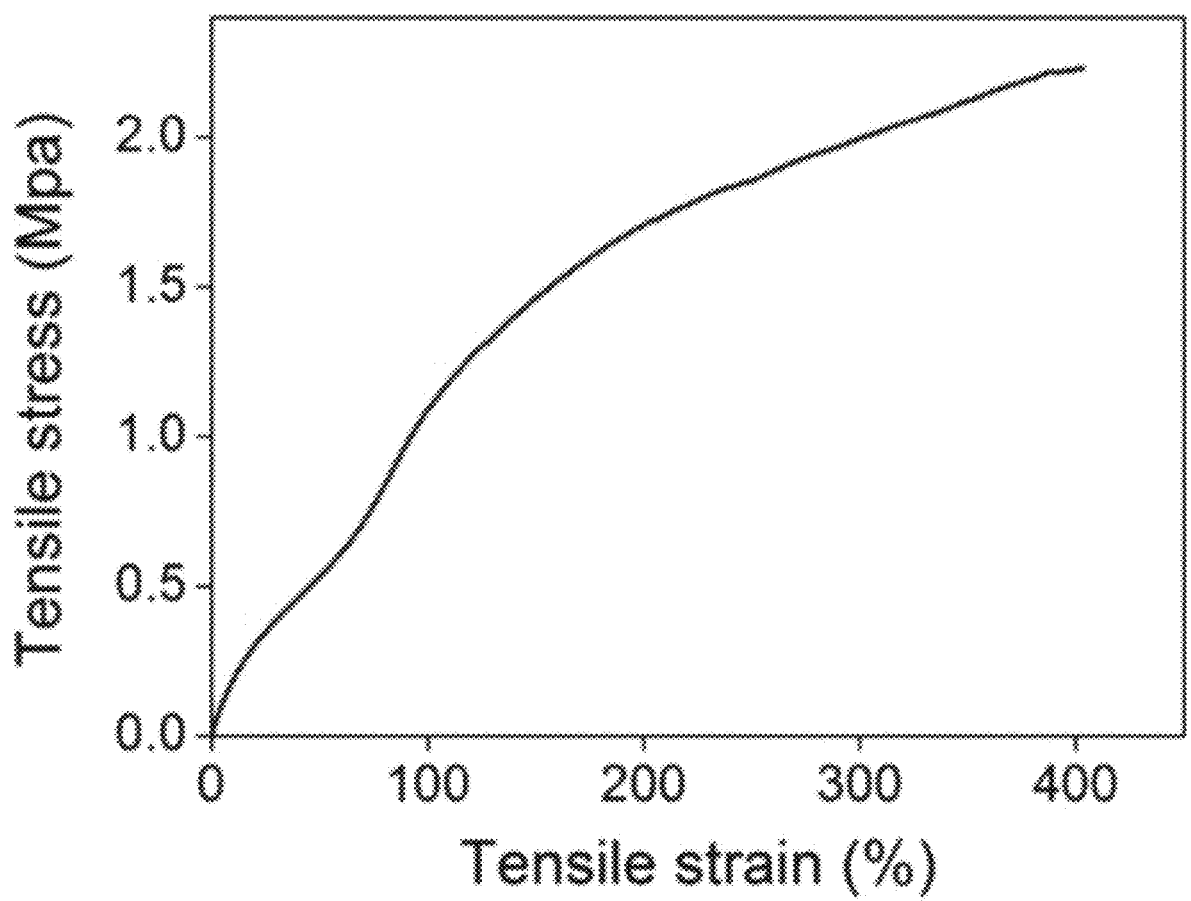
FIG. 12 shows the tensile properties of a hydrogel-coated tube.
Figure 13A:
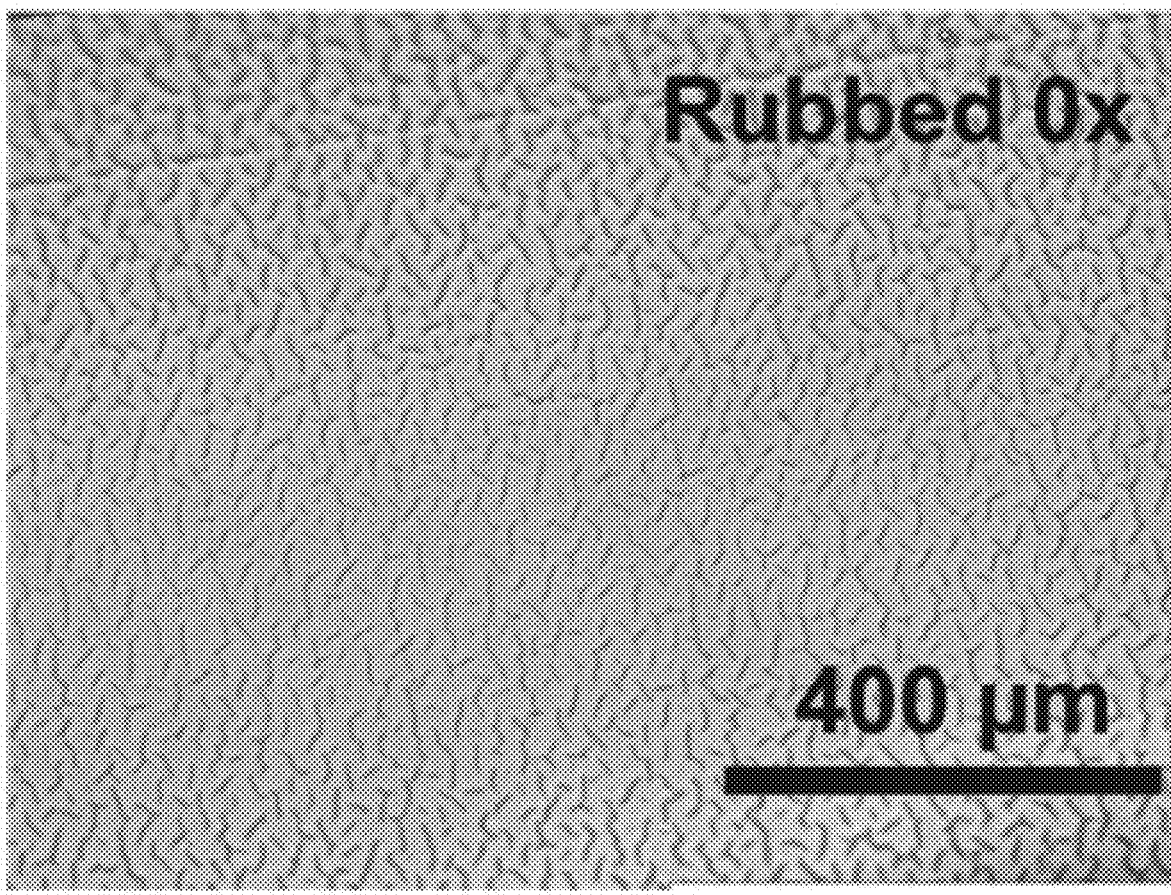
FIGS. 13A-13B are microscopic images of the hydrogel coating of the present application.
Figure 13B:
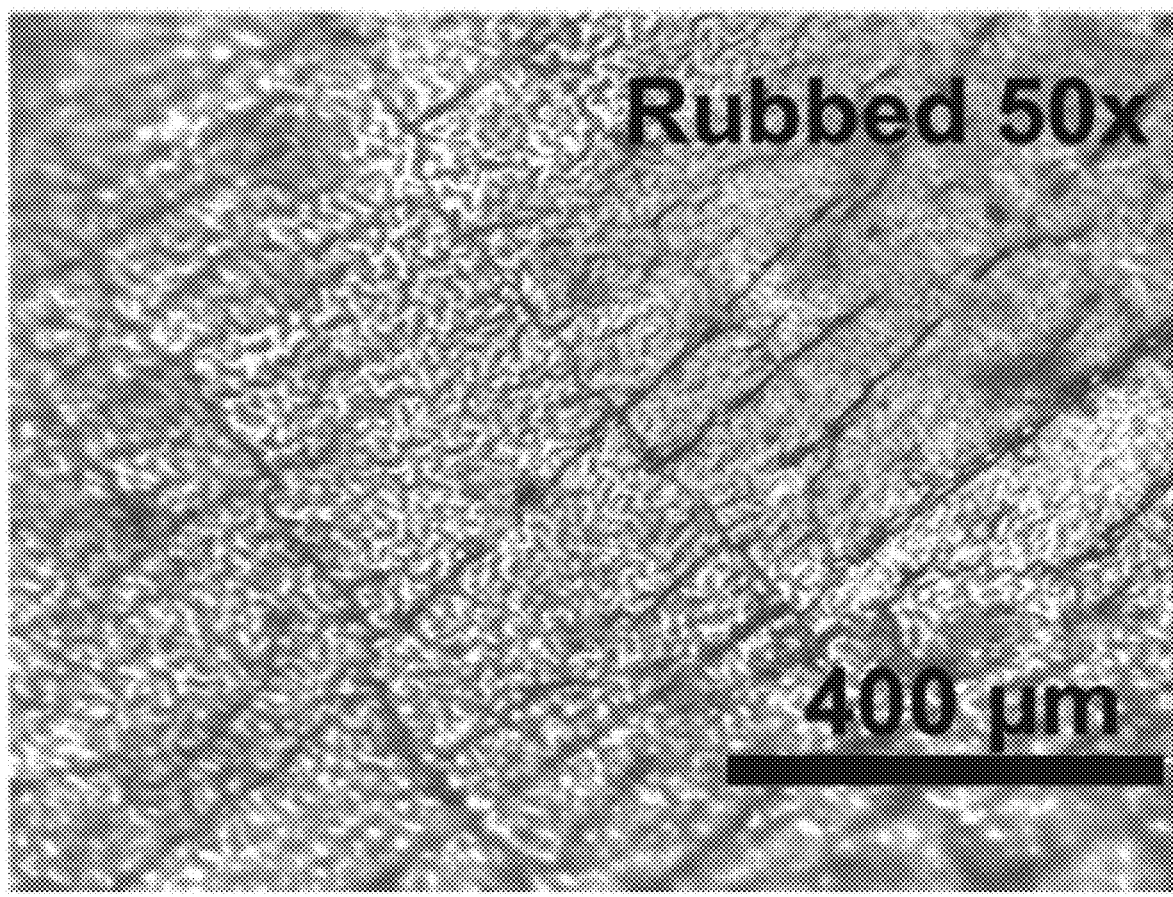

The lubricating property of the hydrogel coated on PDMS was then investigated. The coefficient of friction (COF) results showed over 10 times lower stationary COF compared to that of uncoated PDMS, similar to that of the pure hydrogel (FIG. 3B), and did not seem to be affected by the thickness variation. This low friction is favorable for minimizing the pain associated with insertion or removal of a coated urinary catheter. The coating remained stable after bending or knotting of the catheter (FIG. 11A and FIG. 11B). Next, the toughness of the coating was tested through stretching experiments (FIG. 3C, stained with a red food dye). The hydrogel remained attached on the tubing after being stretched to three times its original length (with a stress of 2 MPa) (FIG. 12). Even when the coated sample was repeatedly scratched with tweezers or a piece of sandpaper, the coating appeared to be unaffected (FIG. 3D). Microscope images taken of a hydrogel coating rubbed with sandpaper showed that scratches could be seen on the surface after 50 rubbing times, but the coating itself remained stable (FIG. 13A and FIG. 13B). This hydrogel coating showed superior mechanical properties, such as lubricity and robustness, and would be advantageous in minimizing the discomfort associated with catheter insertion and removal.

Figure 4A:
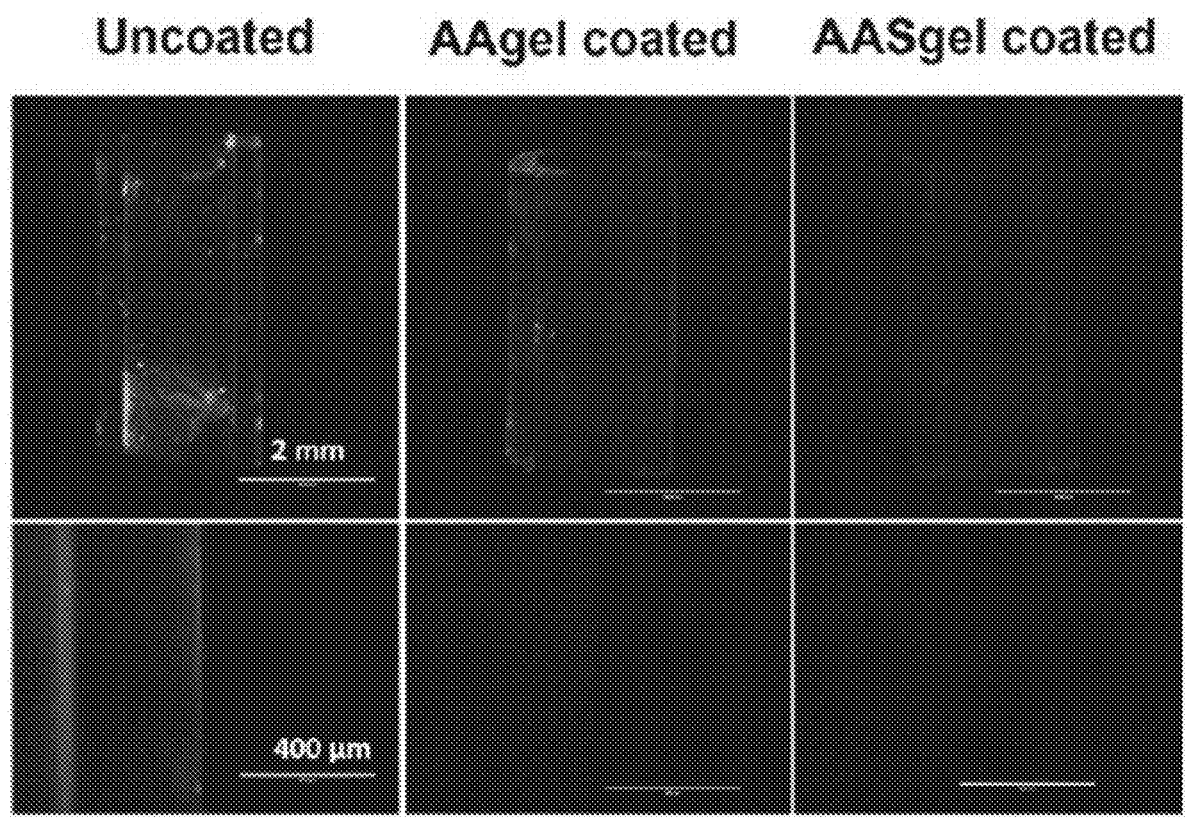
FIGS. 4A-4E show the ability of the hydrogel coating of the present application to resist microbes and fouling.
Figure 4B:
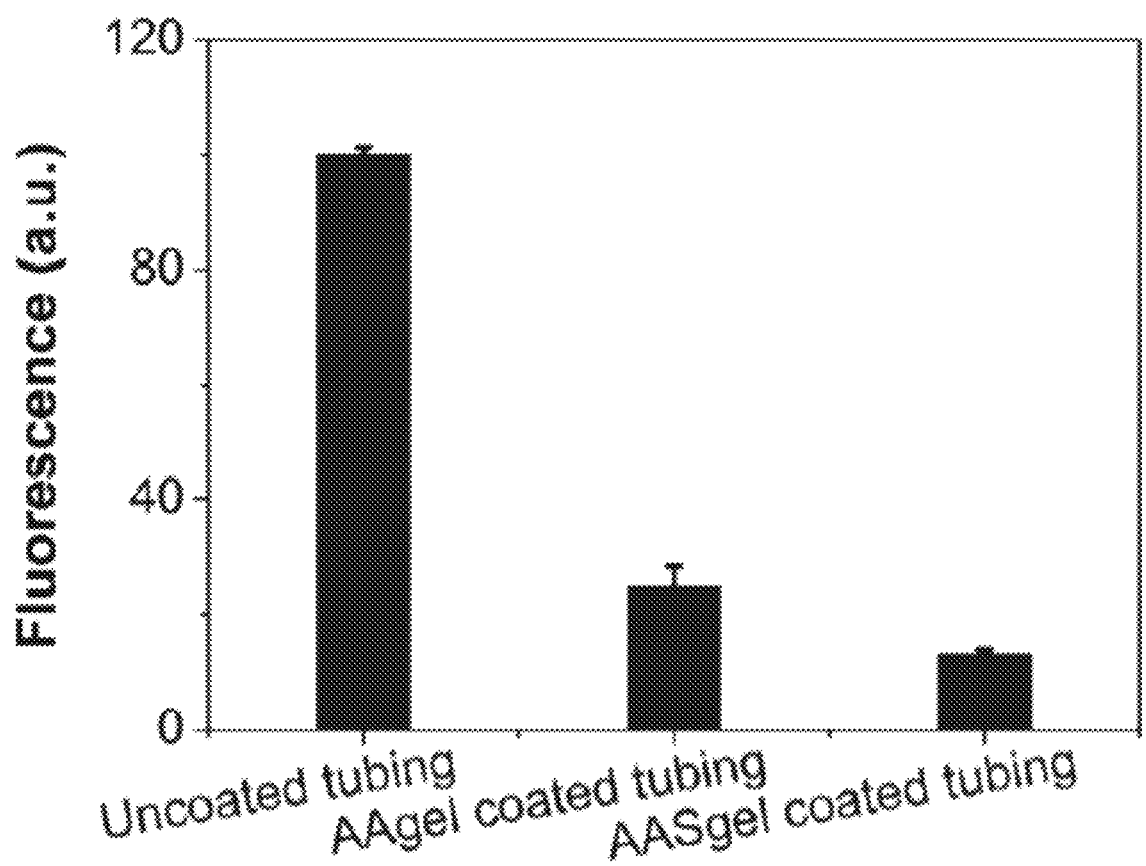

Zwitterionic monomers such as sulfobetaine have shown excellent anti-fouling properties and are thus often used as co-monomers in polymers and hydrogels. Sulfobetaine methacrylate (SBMA) was added as a co-monomer to enhance the anti-fouling property of the hydrogel coating on catheters or silicone tubing. Fluorescence microscopy was used to evaluate the protein adsorption on the uncoated and coated silicone tubing. The samples were soaked in 1 mg/mL FITC-fibrinogen for 30 minutes, washed three times with PBS, and observed. FITC-labeled fibrinogen adhered to blank, AAgel, and AASgel coated samples (FIG. 4A and FIG. 4B). Greater fluorescence intensity was observed with the uncoated control group, suggesting that there was a larger amount of fibrinogen adhesion compared to the hydrogel-coated tubing. Adding SBMA as a co-monomer in the hydrogel further improved the anti-fouling property of this hydrogel coating.

Figure 4C:
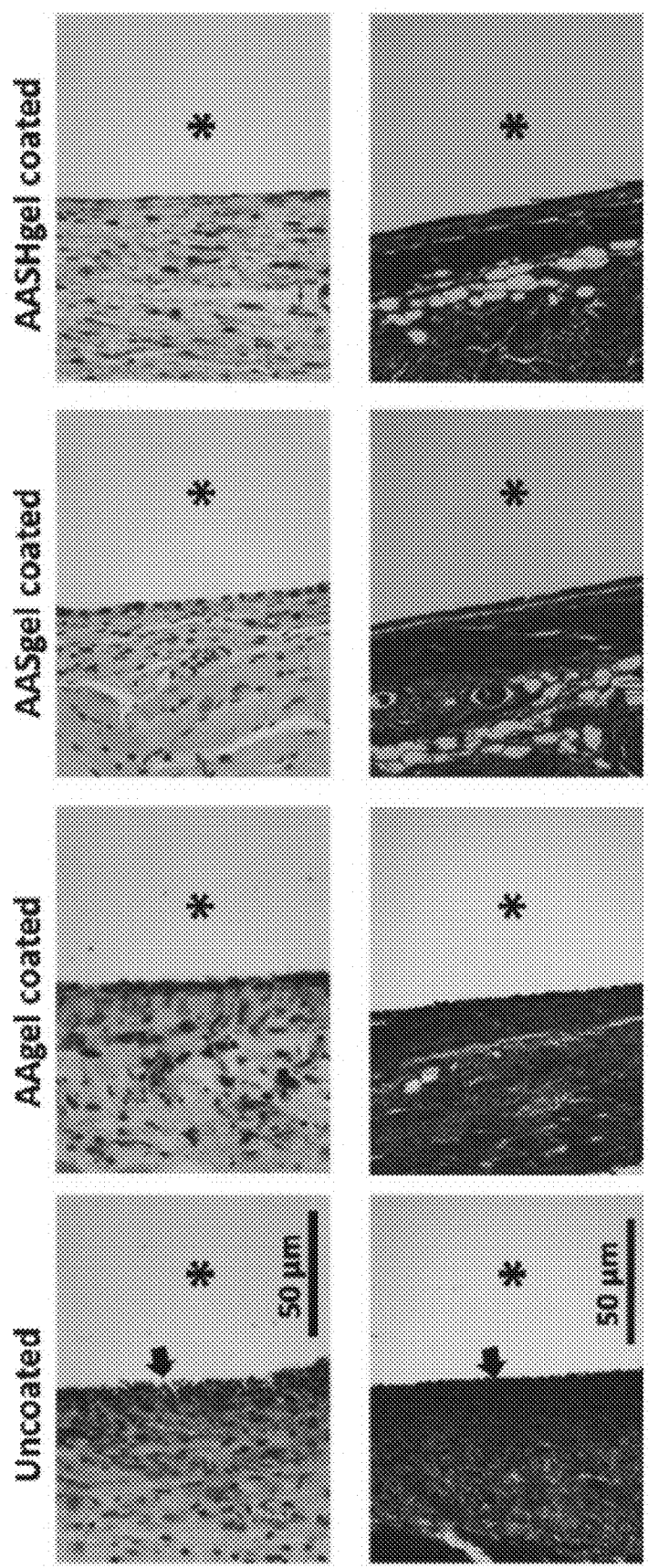
Figure 4D:
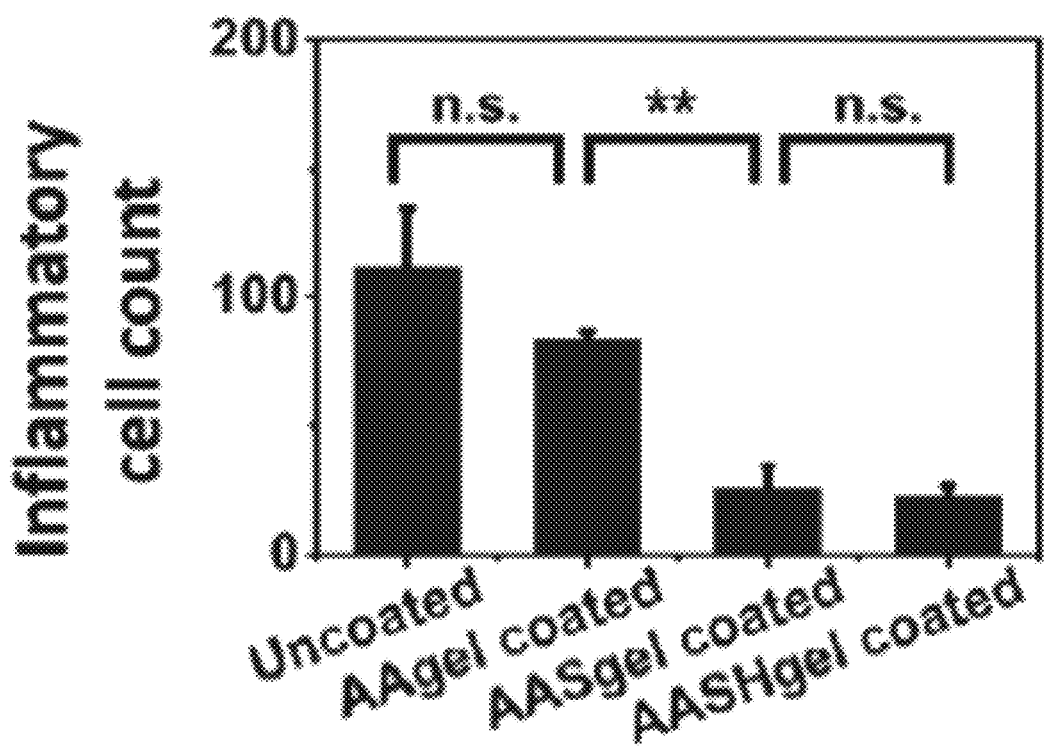
Figure 4E:
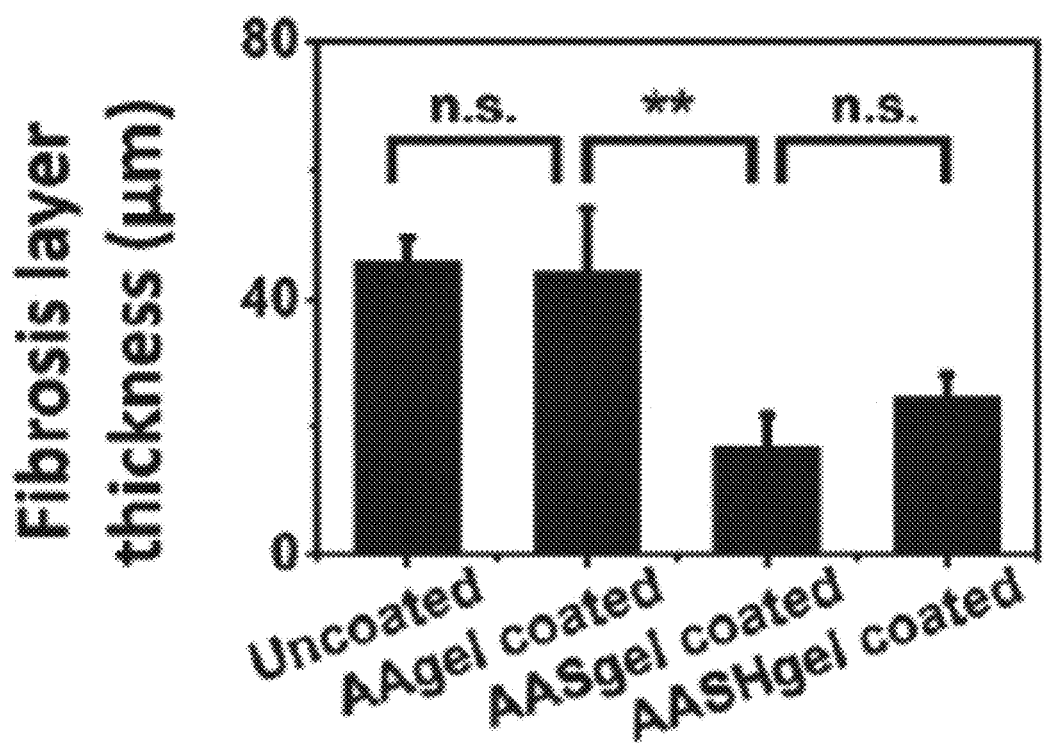

To evaluate the fibrosis-mitigating property of the hydrogel coating, segments of silicone tubing were implanted subcutaneously in mice for four weeks. Samples coated with AAgel, AASgel, or AASHgel were implanted with uncoated silicone tubing as control. The retrieved segments were fixed, sliced and stained with H&E staining and Masson's Trichrome. The representative H&E staining images showed more inflammatory cells at the tissue-tubing interface in the control group, while fewer inflammatory cells were observed on the interface for samples coated with hydrogel. The sample coated with AASgel and AASHgel showed the lowest amount of inflammatory cells (FIG. 4C (top row) and FIG. 4D). Masson's trichrome stain was used to assess fibrotic capsule formation in all samples by measuring the fibrosis layer thickness on the tubing-tissue interface. Much lower capsule thickness was observed for samples coated with AASgel and AASHgel (FIG. 4C (bottom row) and FIG. 4E). This suggests that incorporating sulfobetaine groups in the coating reduced both accumulation of proteins in vitro as well as foreign-body reaction in vivo.

N-halamine-based polymers and coatings have shown anti-bacterial properties. When coated onto catheters, they have the potential to reduce the incidence of catheter-associated uretic infection. In this work, N-halamine was added in the hydrogel coating to obtain anti-bacterial properties. Hydantoin acrylamide (HA) was used as the N-halamine monomer in the hydrogel coating. HA was synthesized by the Bucherer-Berg reaction from N-(1, 1-Dimethyl-3-oxobutyl) acrylamide (DA) by reacting with potassium cyanide and ammonium carbonate at a 1:2:6 M ratio in a 1:1 water/ethanol solvent for four days. Six wt % of HA was added in AAHgel and AASHgel coating on samples. After coating, the oxidative chlorine content [$Cl^+$] in the coating was determined using a thiosulfate titration method; the immobilized [$Cl^+$] in hydrogel coating was $4 \times 10^{17}$ Cl atoms/$cm^2$, while no [$Cl^+$] was observed in uncoated samples.

Figure 5A:
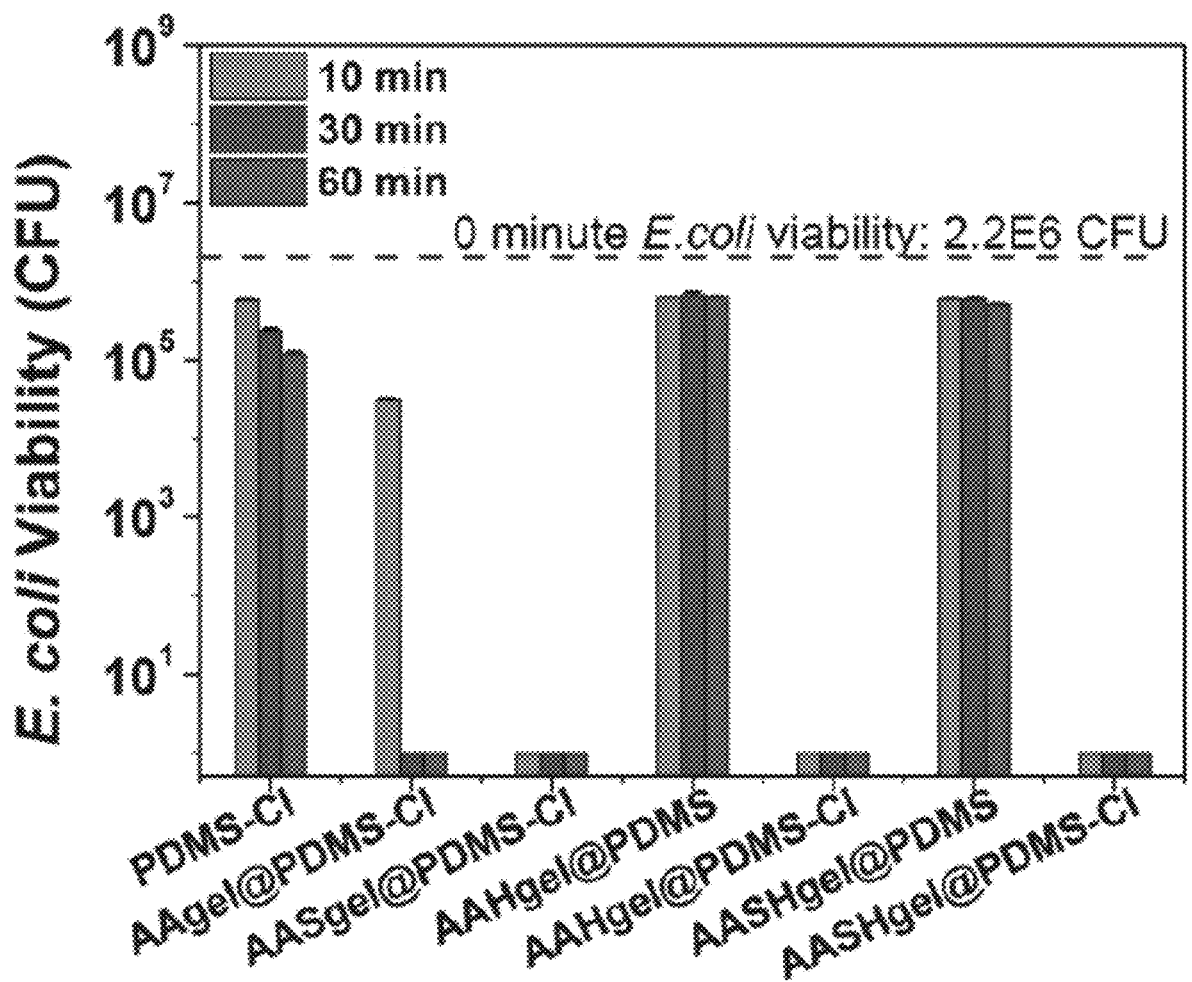
FIG. 5A shows *E. coli* viability after distribution on chlorinated hydrogel-coated substrates.
Figure 5B:
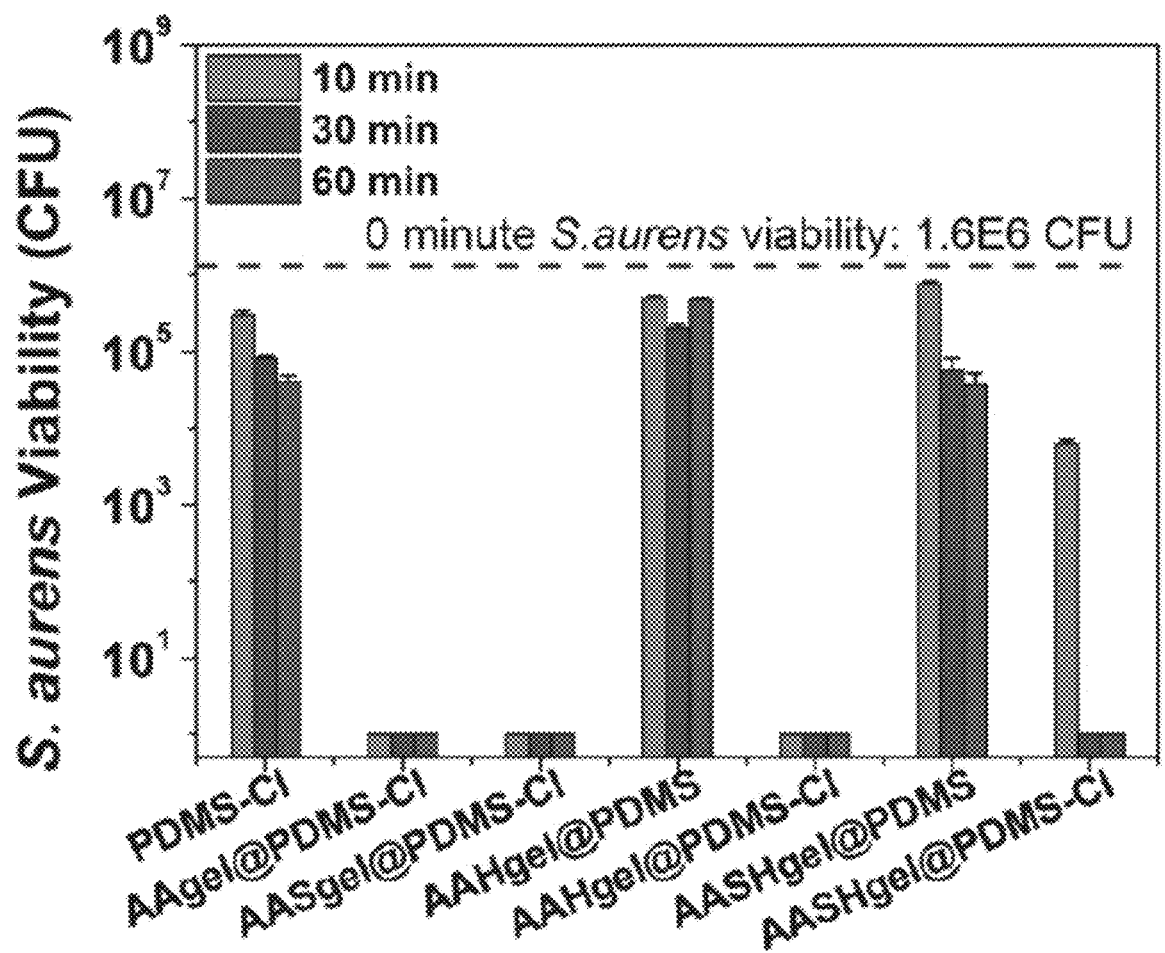
FIG. 5B shows *S. aureus* viability after distribution on chlorinated hydrogel-coated substrates.
Figure 14:
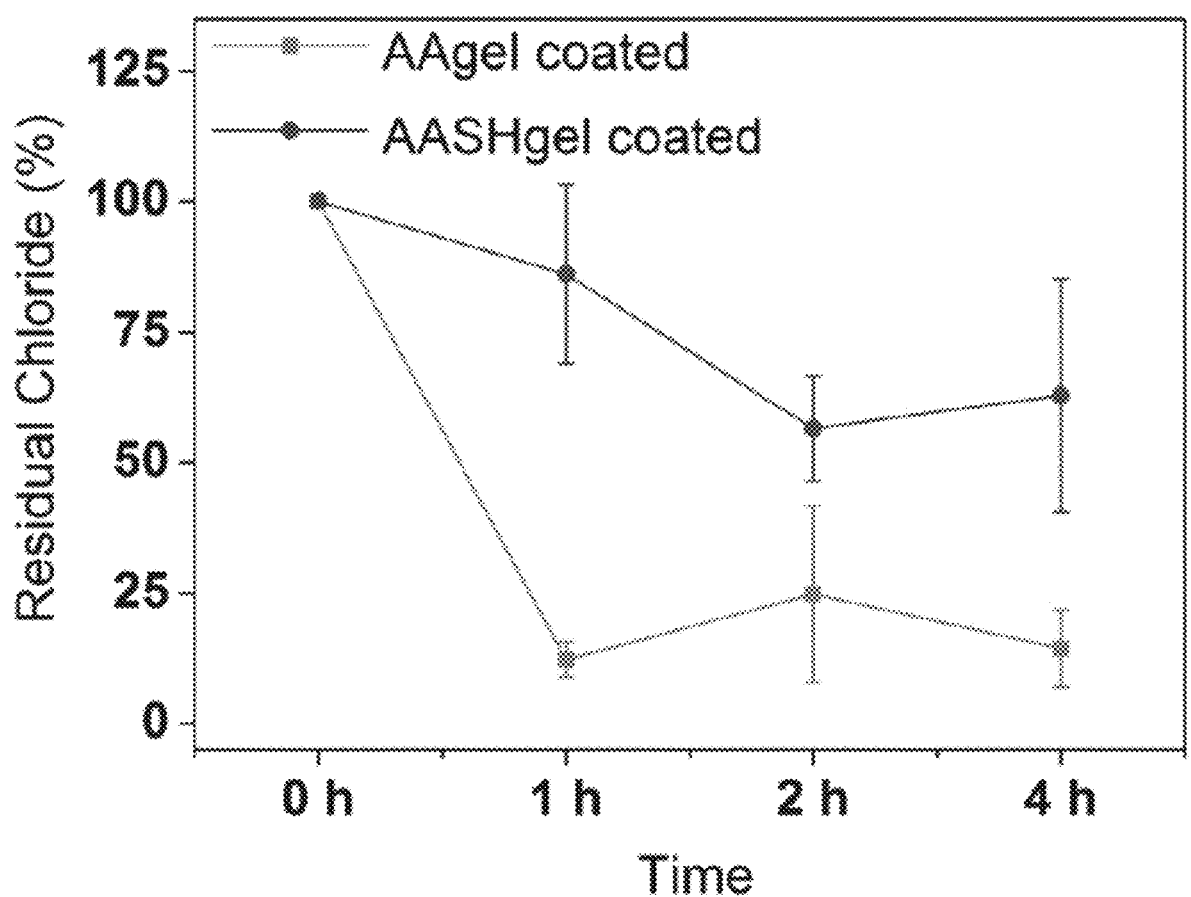
FIG. 14 is a graphical representation showing the UV stability for chlorinated hydrogel-coated samples.

Short-period anti-bacterial assays were carried out with chlorinated-HA-containing hydrogel coated onto standard 1 $inch^2$ PDMS pads. Samples were chlorinated using 10 wt % commercial bleach for one hour. In this experiment, uncoated PDMS-Cl was used as a control, chlorinated AAgel@PDMS-Cl, AASgel@PDMS-Cl, AAHgel@PDMS-Cl, and AASHgel@PDMS-Cl samples were tested, and unchlorinated AAHgel@PDMS and AASHgel@PDMS samples were used as additional negative controls. To avoid any inactivation caused by free chlorine after the chlorination process, the chlorinated samples were washed with distilled water three times during one hour, and dried overnight at room temperature. After extensive washing, samples were challenged with *E. coli* O157:H7 (gram-negative) and *S. aureus* (gram-positive) bacteria, two model bacteria commonly present in urinary tract infections. A total amount of 25 µL of bacteria suspension of ~$10^6$ CFU was uniformly distributed between a pair of coated PDMS pads. After 10, 30, and 60 minutes of treatment, the bacteria were washed off with 5 mL of $Na_2S_2O_3$ buffer, and the suspension was diluted, plated, and counted after 16 hours. All chlorinated hydrogel coated PDMS pads showed significant anti-bacterial properties by providing complete inactivation of *S. aureus* and *E. coli* O157:H7 bacteria within 30 minutes (FIG. 5A and FIG. 5B). In contrast, less than one log of bacteria reduction was observed for chlorinated PDMS pad with no coating or hydrogel coated PDMS pads without chlorination. The acrylamide monomer in the hydrogel can also react with chloride to form unstable chemical bonds and showed anti-bacterial property. After four hours of UV-light stability test, only 10% of chloride was observed on chlorinated AAgel coated samples. In contrast, over 50% of chloride was observed on chlorinated AASHgel coated samples (FIG. 14).

Figure 5C:
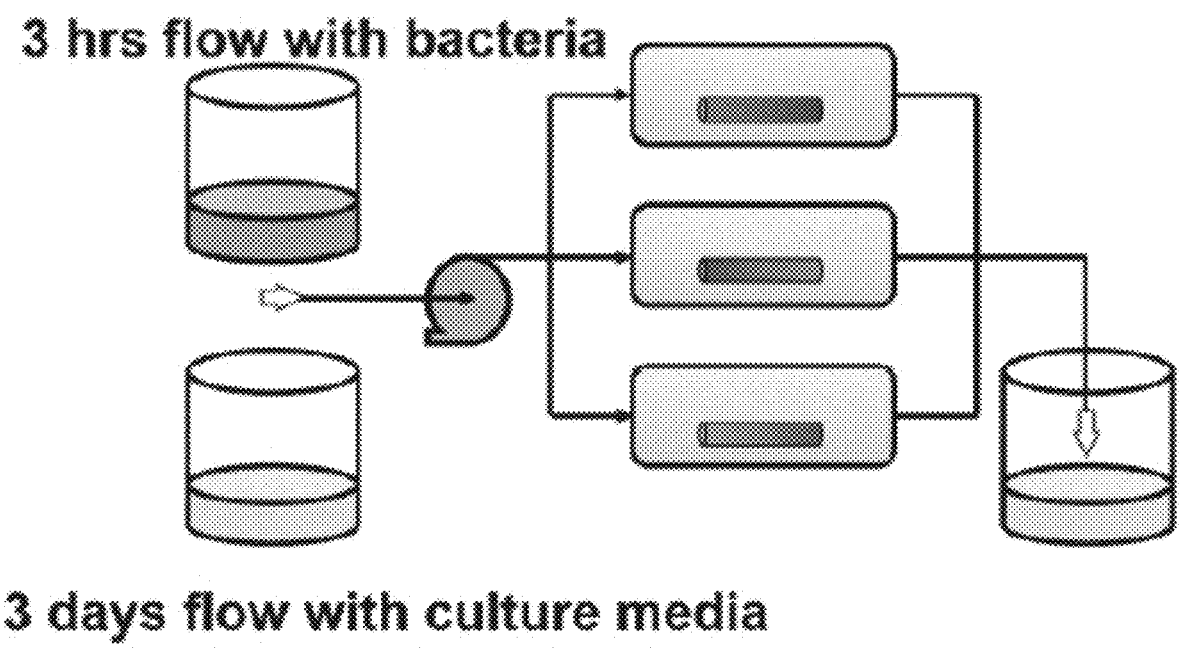
FIG. 5C shows schematic representations of a long-term dynamic bacterial adhesion experiment.
Figure 5D:
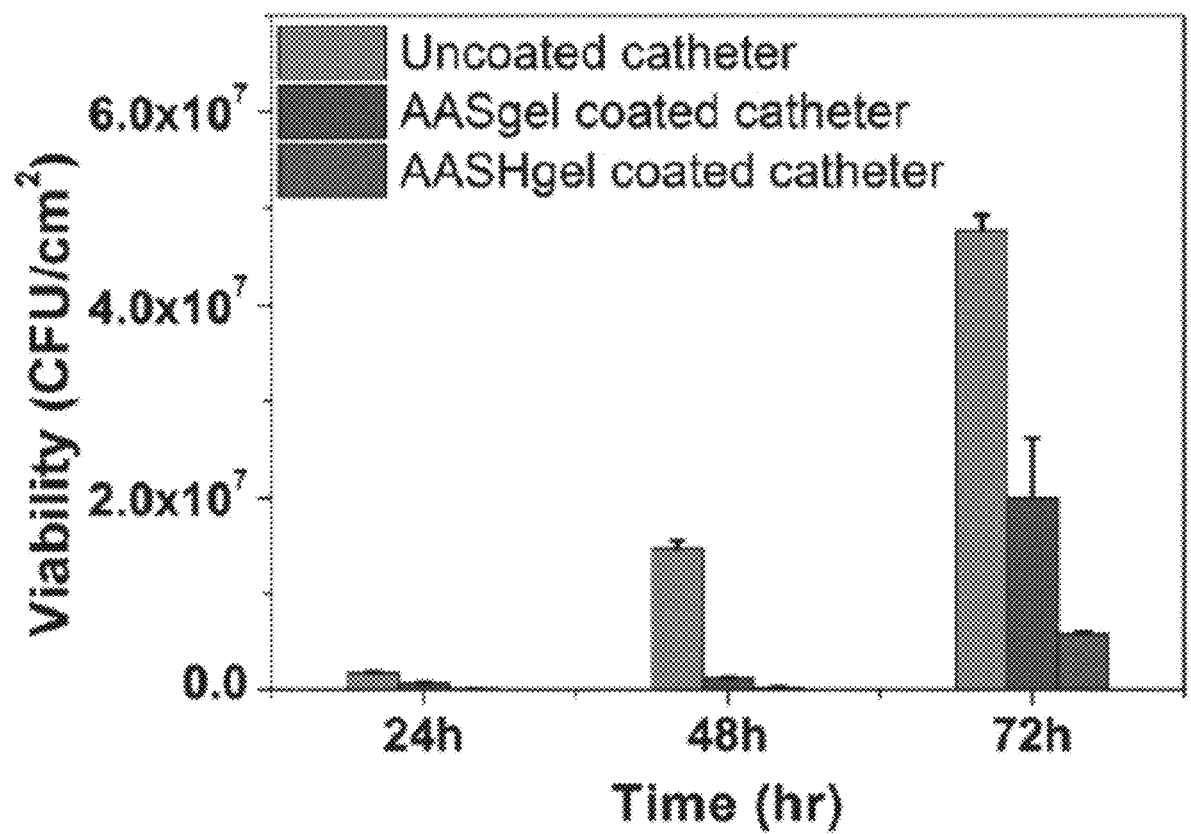
FIG. 5D shows total bacteria adhered to catheter samples after 24, 48, and 72 hours of flow.
Figure 5E:
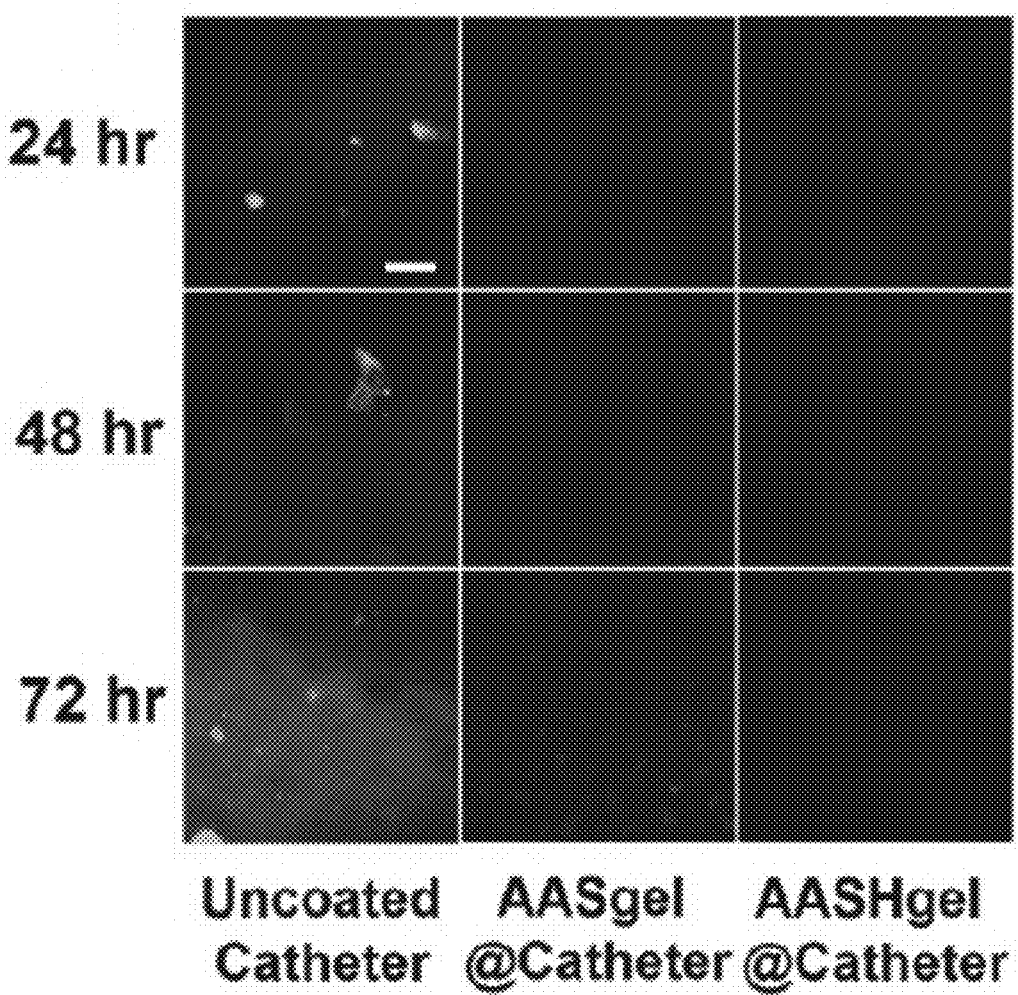
FIG. 5E shows confocal images of bacterial adhesion on samples.
Figure 15:
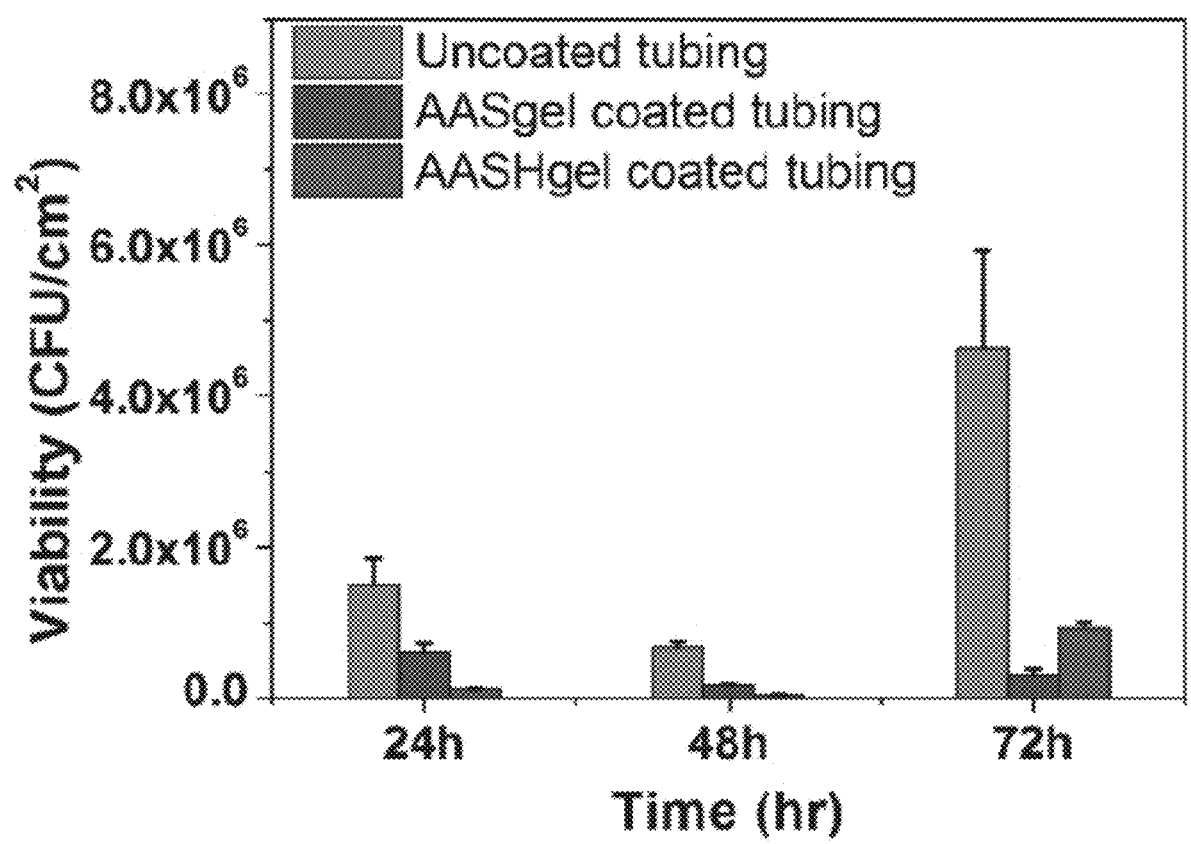
FIG. 15 is a graphical representation showing the total bacteria adhered on silicone tubing samples after 24, 48, and 72 hours of flow.

To test the ability of the coating to achieve long-term inhibition of bacterial growth, bacterial adhesion was evaluated with a parallel flow system (FIG. 5C). The system was designed to mimic the catheter-associated infections that may happen shortly after a catheter is inserted. Commercial catheters and medical grade silicone tubing without coating were used as control. Samples with AASgel coating and chlorinated AASHgel coating were used as anti-fouling and anti-bacterial samples, respectively. *S aureus* was used as the model bacteria. The bacterial suspension containing $10^6$ CFU/mL of *S. aureus* was first pumped into chambers for three hours at 1 mL/min in each chamber to allow bacteria to adhere to sample surface. Sterile medium was then continuously pumped for three days at 1 mL/min in each chamber to allow bacteria growth on the sample surface and unbound bacteria to be removed. Two sample segments were taken out every 24 hours and gently washed three times with PBS buffer. One of the samples was stained with a bacterial viability kit and observed using confocal microscopy. Bacteria on the other sample was washed off into suspension, diluted and plated. The colonies were counted after 16 hours. The bacteria adhered to hydrogel coated catheters was significantly lower compared with uncoated catheter (FIG. 5D). Experiments using coated silicone tubing also showed similar trends (FIG. 15). Confocal imaging showed the catheter surface was covered with bacteria while the samples with hydrogel coating exhibited much less fluorescence (FIG. 5E). Both anti-bacterial and anti-fouling properties have contributed to the low level of bacterial adhesion on the hydrogel-coating. These results suggested hydrogel coated catheters possess promising anti-fouling/anti-bacterial property in infection-causing environments. This may significantly reduce the risk of catheter-related infections.

Discussion of Examples 1 and 2

Reducing biofouling while increasing lubricity of inserted medical catheters is highly desirable to improve their comfort, safety, and long-term use. Disclosed here is a simple method to create thin (~30 µm) conformal lubricating hydrogel coatings on catheters. The key to this method is a three-step process including Shape-forming, Gradient crosslinking and Swell-peeling (SGS). First, the fast gelation of agar was used to form a hydrogel layer conformal to catheters. Next, a surface-bound UV crosslinking of acrylamide mixed in agar in open air was performed, purposely allowing gradual oxygen inhibition of free radicals to generate a gradient of crosslinking density across the hydrogel layer. Finally, the hydrogel was swelled to let the non-crosslinked/loosely attached hydrogel fall off, leaving behind a surface-bound, thin, and mostly uniform hydrogel coating. This method also allowed easy incorporation of different polymerizable monomers to obtain multifunctionality. For example, incorporating an anti-fouling, zwitterionic moiety sulfobetaine in the hydrogel reduced both in vitro protein adsorption and in vivo foreign-body response in mice. Addition of a biocidal N-halamine monomer to the hydrogel coating deactivated both *Staphylococcus aureus* (*S. aureus*) and *Escherichia coli* (*E. coli*) O157:H7 within 30 min of contact and reduced biofilm formation by 90% compared to that of uncoated commercial catheters when challenged with *S. aureus* for three days. The lubricating, anti-biofouling hydrogel coating may bring clinical benefits for urinary and venous catheters, as well as other types of medical devices A conformal and tough hydrogel coating with ~30 µm thickness on catheters was formed through a three-step method of "Shape-forming, Gradient crosslinking, and Swell-peeling." The simulation of mass transfer during UV cross-linking in open air indicated that radicals were distributed in the catheter surface region ranging from 0 to 100 forming a gradient of crosslinking density. The hydrogel coating led to a 10-fold lower surface coefficient of friction which is advantageous for minimizing the discomfort associated with catheter insertion and removal. The robustness of the coating was shown by stretching and rubbing experiments. Incorporating sulfobetaine groups in the hydrogel coating greatly reduced both accumulation of proteins in vitro and foreign-body reaction in vivo. By introducing N-halamine hydantoin acrylamide groups into the hydrogel, over $4 \times 10^{17}$ Cl atoms/$cm^2$ were immobilized on the sample surface coating after bleach chlorination. The coating deactivated over six logs of *S. aureus* and *E. coli* O157:H7 within 30 minutes of contact. The coatings also significantly reduced long-term bacteria adhesion on catheter/tubing samples. After three days of culture, the level of *S. aureus* accumulated on the AASHgel coated catheter was 10-times less compared to uncoated catheters. Capable of suppressing bacteria adhesion and killing adhered bacteria, along with superior mechanical properties such as lubricity and stability, this hydrogel coating has great potential in advancing the next generation catheters and many other medical devices.

Example 3—Efficacy of Conformal Hydrogel Coatings

Materials

[2-(Methacryloyloxy)ethyl]dimethyl-(3-sulfopropyl)ammonium hydroxide (SBMA, Mn=279.35) as a monomer, poly(ethylene glycol)dimethacrylate (PEGDMA, Mn=550) as a crosslinker, and photoinitiator Irgacure 2959 (I-2959), as an initiator, were all purchased from Sigma-Aldrich. HA was synthesized as previously described.

Preparation of Poly(SBMA-HA) Hydrogels with Different Elastic Moduli

Different poly(SBMA-HA) hydrogels were prepared using a previous method with modification. Here, the elastic modulus of polySBMA hydrogels was achieved by the chemical cross-linker percentage. The monomer (SBMA) and HA were first dissolved in deionized (DI) water. The cross linker (PEGDMA) was varied from 0.1%, 0.5%, 1% to 5% (versus monomer w/w), and the initiator (I2959) (final 1% versus monomer w/w) was added and completely dissolved in the above solutions at room temperature. The final concentration of the monomer was 4 M. The solution mixture was then transferred onto a pair of glass plates separated by poly-(tetrafluoroethylene) (PTFE) (with a thickness of 3 mm or 1 mm). Next, the photo-polymerization reaction was carried out at room temperature with 365 nm UV light for 1 h. After the polymerization, the hydrogels were removed from the plates and immersed into 10% of house bleach solution (Clorox, pH was adjusted to 7.0) for 30 min (N-halamine activation). The gel was then taken out and washed with large quantity of DI water (1 L), which was changed every 3 h for 5 days to ensure that non-reacted initiators or monomers and free chlorines were totally removed from the hydrogels.

Determination of Equilibrium Water Content (EWC) of the Hydrogels

The swelling kinetics of the polySBMA hydrogels was tested using a gravimetric method. Prepared swollen hydrogels of the same size were first freeze-dried (Wd) and then immersed in deionized water. At each time interval, the samples were wiped with filter paper to remove the water. The weight of the hydrogels was measured as Wt. The degree of swelling ratio was calculated using the following equation:

$$\text{Swelling ratio (\%)} = \frac{W_t - W_d}{W_d} \times 100\%$$

Figure 17:
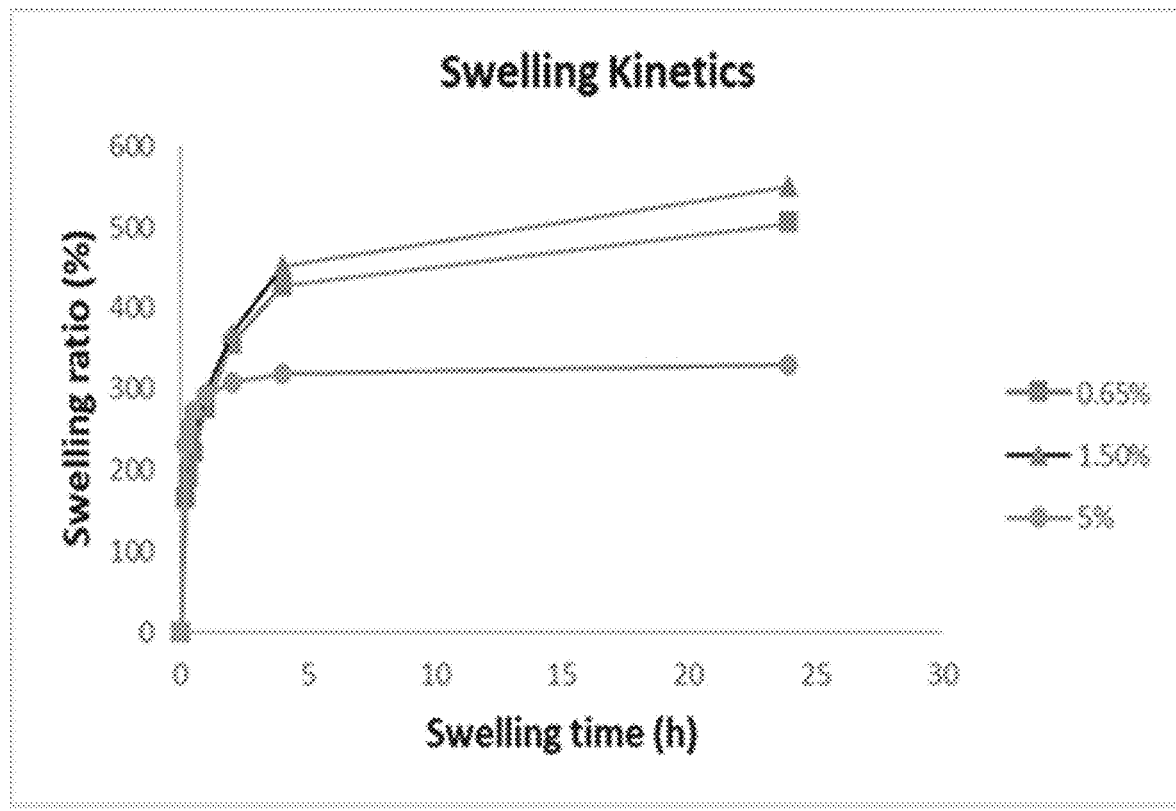
FIG. 17 shows the swelling kinetics of halamine-zwitterion hydrogels with cross-linker concentrations of 0.65%, 1.5%, and 5%.

FIG. 17 shows the swelling kinetics of the polySBMA hydrogels with cross-linker concentrations of 0.65%, 1.5%, and 5%.

Mechanical Testing of Hydrogel

Figure 18A:
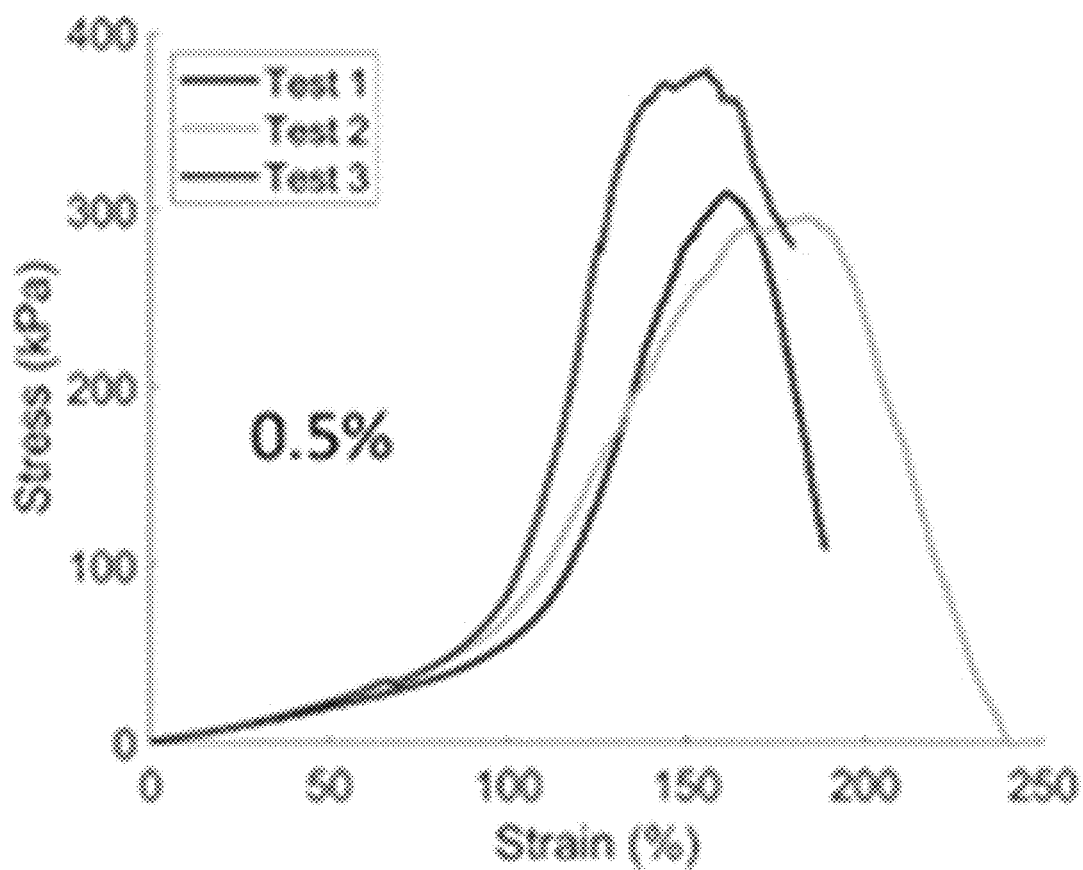
FIGS. 18A-18D show the hydrogels tensile and elastic properties.
Figure 18B:
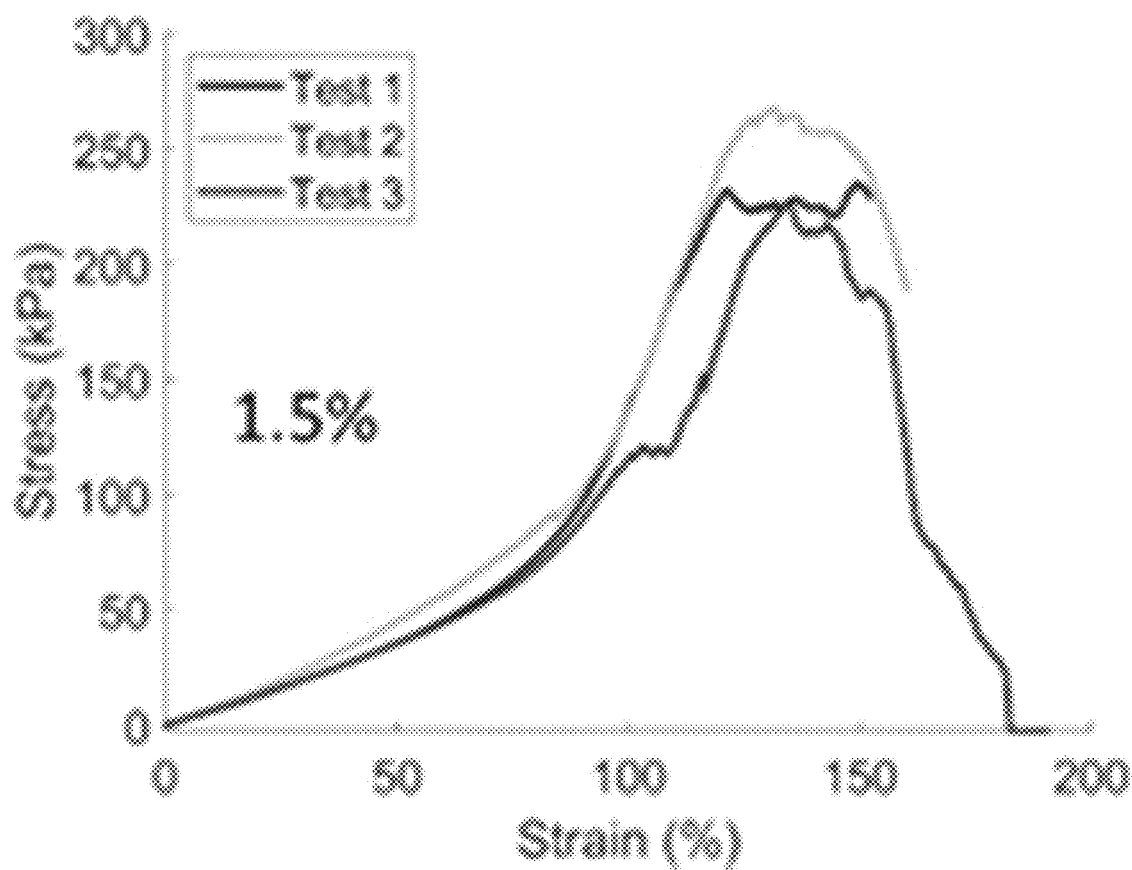
Figure 18C:
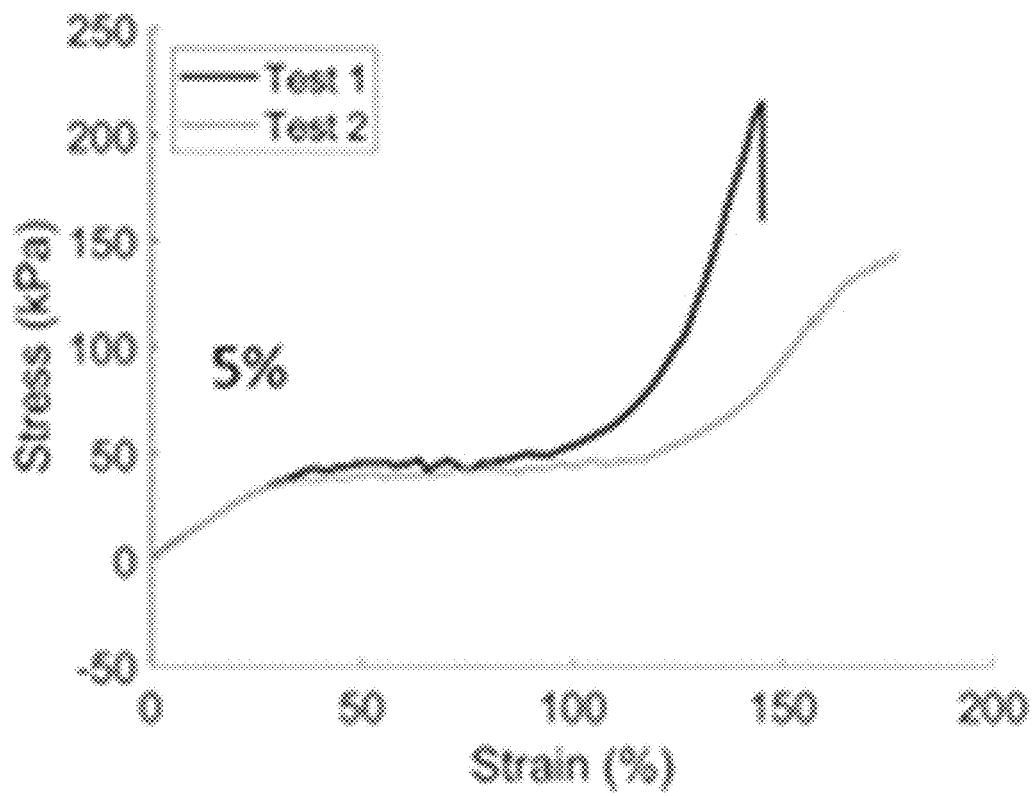
Figure 18D:
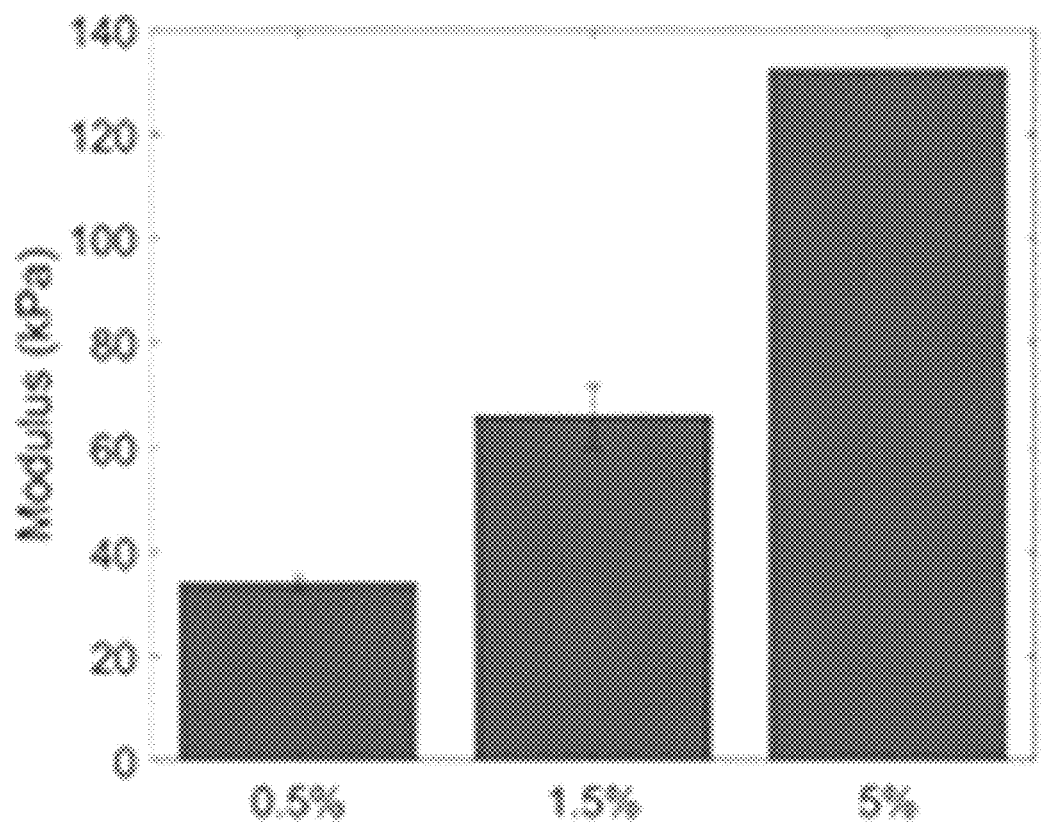

The mechanical properties of the hydrogels were tested by uniaxial tension tests. Hydrogels with different crosslinking densities were loaded in tension using a custom-built tensile tester. Specimens were cut into rectangular specimens with a width of 15 mm and a thickness of 1.5 mm. The specimen length between the two grips of the tensile tester, the gauge length, was 30 mm. The specimens were loaded at 0.5 mm/s. The stress a was determined as the measured tensile force F divided by the initial cross-sectional area AO. The strain was determined by the specimen elongation ΔL divided by the gauge length LO. FIG. 18A shows uniaxial tensile testing properties of hydrogels with a 0.5% cross-linker concentration. FIG. 18B shows uniaxial tensile testing properties of hydrogels with a 1.5% cross-linker concentration. FIG. 18C shows uniaxial tensile testing properties of hydrogels with a 5% cross-linker concentration. FIG. 18D shows elastic moduli extracted from the stress-strain curves of FIG. 18A, FIG. 18B, and FIG. 18C. The moduli were calculated using the linear part of the stress-strain curves.

Storage Stability Test (Titration)

Figure 19:
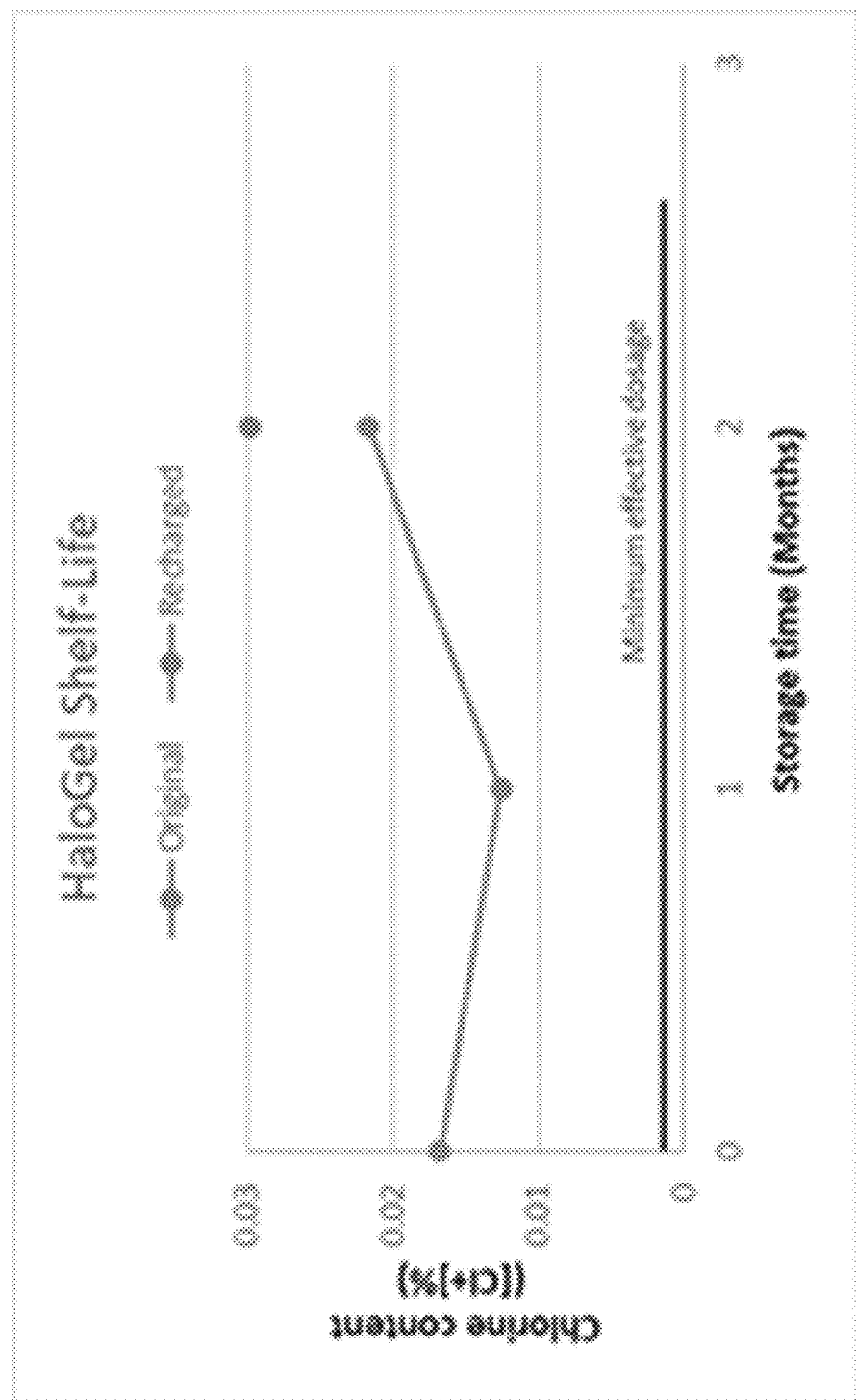
FIG. 19 shows the shelf-life of an HA-SBMA hydrogel at room temperature.

The storage or shelf life stability of the oxidative chlorine bound onto the HaloGel by the chlorination procedure was evaluated. Wound dressings were stored in sealed opaque packaging in a cabinet (dark environment) at room temperature. The stability of the chlorine content over time was measured for up to 2 months. The stabilities of the N-halamine-coated dressings were determined by measuring the amount of remaining chlorine on the samples by using the standard iodometric/thiosulfate titration procedure. The weight percentage of the bound oxidative chlorine was calculated according to the following formula:

$$Cl+\% = 35.45 \times N \times V/(2 \times W) \times 100, \quad (2)$$

where Cl+% is the weight percent of oxidative chlorine on the samples, N and V are the normality (equiv/L) and volume (L) of the titrant ($Na_2S_2O_3$), respectively, and W is the weight of the sample (g) used for the titration. To recharge, the samples were treated with same chlorine bleaching conditions. FIG. 19 and Table 2 below show the shelf-life of HA-SBMA hydrogel at room temperature.

TABLE 2

Shelf-life of HA-SBMA Hydrogel at Room Temperature

| Storage Time | Chlorine Content (%) | |
|---|---|---|
| (Months) | Original | Recharged |
| 0 | 0.0168 | |
| 1 | 0.0126 | |
| 2 | 0.0217 | 0.0298 |

Benchmark Studies of Antimicrobial and Anti-Fouling Functions with Commercial Wound Dressing Products— Anti-Fouling/Anti-Protein Adhesion (Zwitterion)

Protein adsorption tests were carried out using FITC-labeled fibrinogen (1 mg/mL) dissolved in phosphate-buffered saline (PBS), pH 7.4. Halamine-Zwitterion hydrogel dressings were equilibrated in PBS buffer for 30 minutes. The PBS solution was then replaced with fibrinogen solution, which remained in contact for another 30 minutes. After this period, the dressings were gently washed three times with PBS buffer, and fluorescence microscope images were obtained on an EVOS® FL Cell Imaging System. The adsorbed protein was presented as the relative fluorescence intensity by processing the images with ImageJ. The Halamine-Zwitterion hydrogel dressings were compared with the following commercial wound dressings: DuoDerm Extra Thin Adhesive Dressing, and CVS Honey Adhesive Dressing.

Figure 20A:
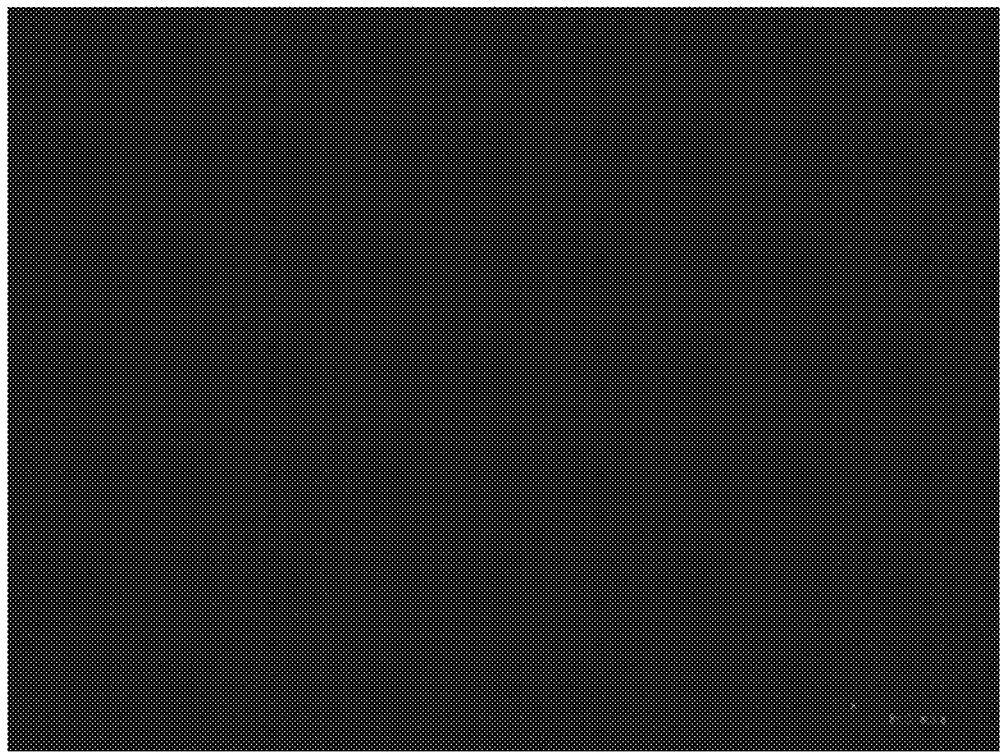
FIGS. 20A-20D show the Fluorescence microscopy images of the hydrogel of the present application compared to commercially available wound dressings.
Figure 20B:
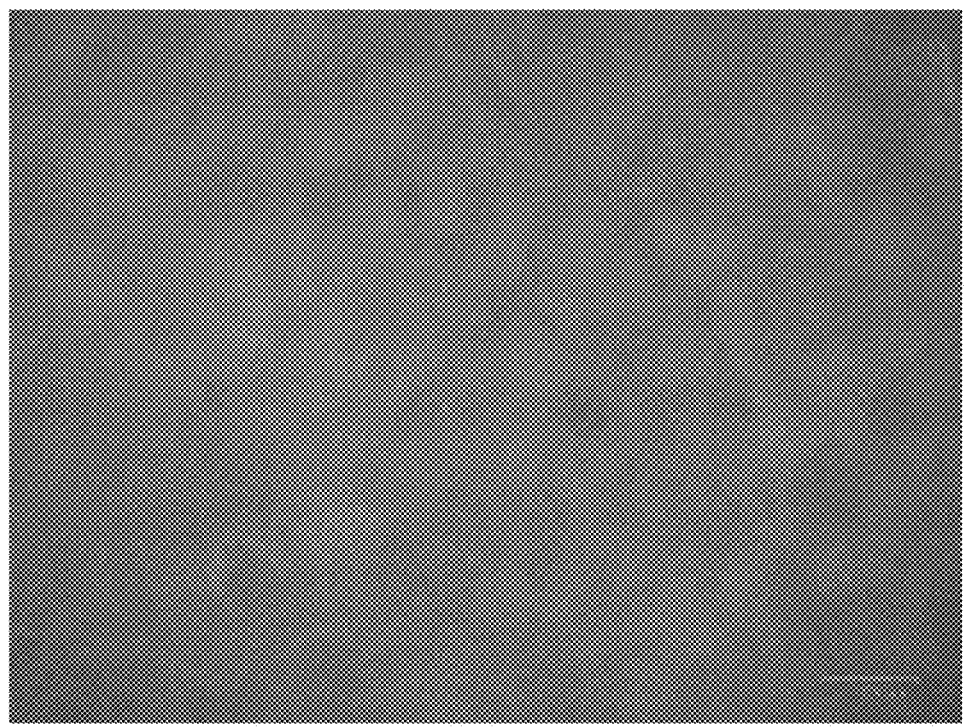
Figure 20C:
Figure 20D:
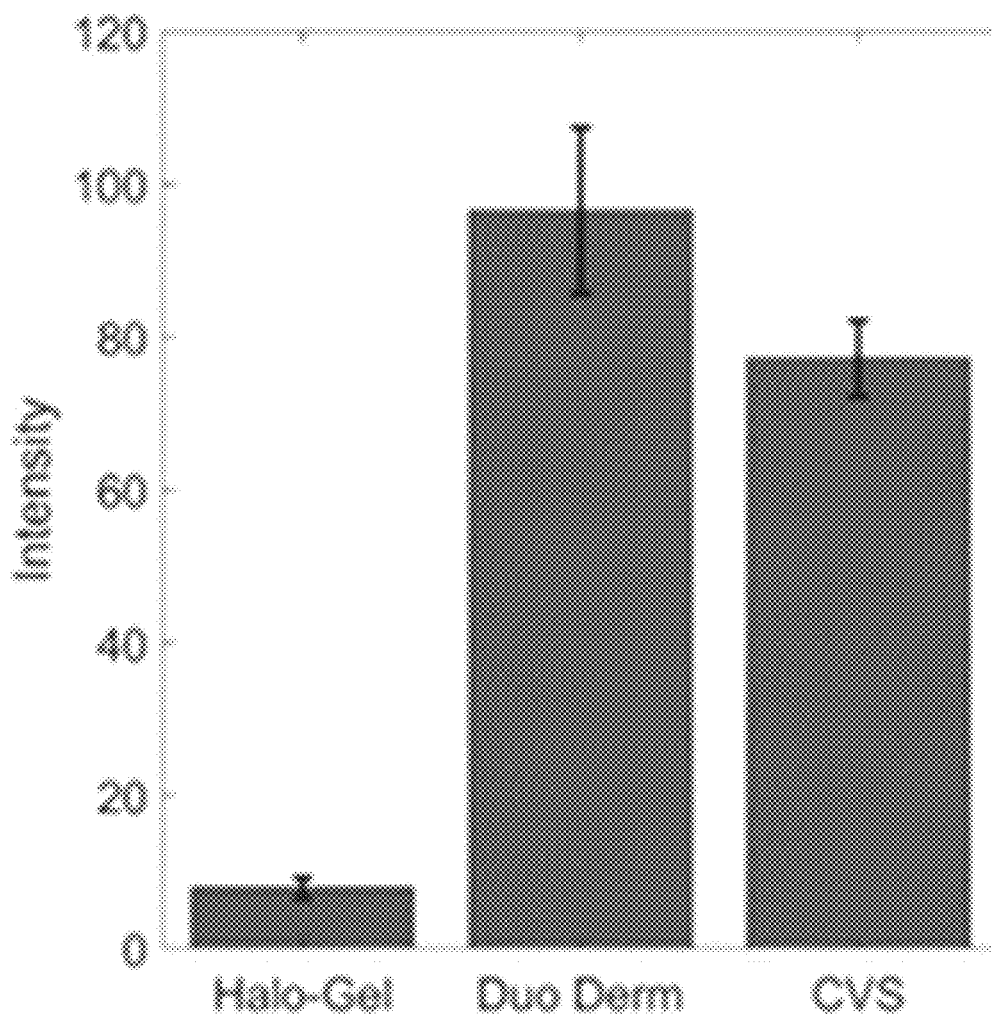

FIG. 20A shows a fluorescence image of protein adhesion to a Halamine-Zwitterion hydrogel dressing. FIG. 20B shows a fluorescence image of protein adhesion to a Duo-Derm Extra Thin Adhesive commercially available wound dressing. FIG. 20C shows a fluorescence image of protein adhesion to a CVS Honey Adhesive commercially available wound dressing. FIG. 20D shows the quantified intensities of the fluorescence images of FIG. 20A, FIG. 20B, and FIG. 20C. Higher fluorescence indicates more protein adhered to a given substrate. FIG. 20A shows very low intensity (i.e., very low protein adhesion to the Halamine-Zwitterion hydrogel dressing), while FIG. 20C shows much higher intensity (i.e., higher protein adhesion to the CVS Honey Adhesive commercially available wound dressing), and FIG. 20B shows even higher intensity (i.e., even higher protein adhesion to the DuoDerm Extra Thin Adhesive commercially available wound dressing). The very low protein adhesion shown in FIG. 20A is preferred over the higher protein adhesion shown in FIG. 20B and FIG. 20C.

In Vitro Antimicrobial Efficacy Testing (N-Halamine Function)

For anti-bacterial tests, strains (as listed in Table 3) were cultured in brain-heart infusion (BHI) buffer for 16 h at 37° C. with 120 rpm rotation. Then the bacteria were washed twice with Butterfield's phosphate buffer (BPB) and adjusted to ~$10^6$ colony forming units (CFU) in either PB buffer or LB medium for the following tests. A "sandwich" testing method was used for anti-bacteria test. Briefly, 50 μL of bacterial suspension was inoculated in the center of a 1 inch hydrogel sample. An identical sample was put on the top and a sterile weight was added to ensure full contact. After contact for 5, 15, or 30 minutes, the samples were placed into 5 mL of $Na_2S_2O_3$ solution (0.05 N) to quench all oxidative chlorines on the surface. All samples were vortexed for 2 minutes to detach all survived bacteria and then serial dilutions were prepared using pH 7, 100 μM phosphate buffer solutions which were plated on trypticase soy agar plates. After the plates were incubated at 37° C. for 24 h, viable bacterial colonies were counted for the biocidal efficacy analysis.

Figure 21A:
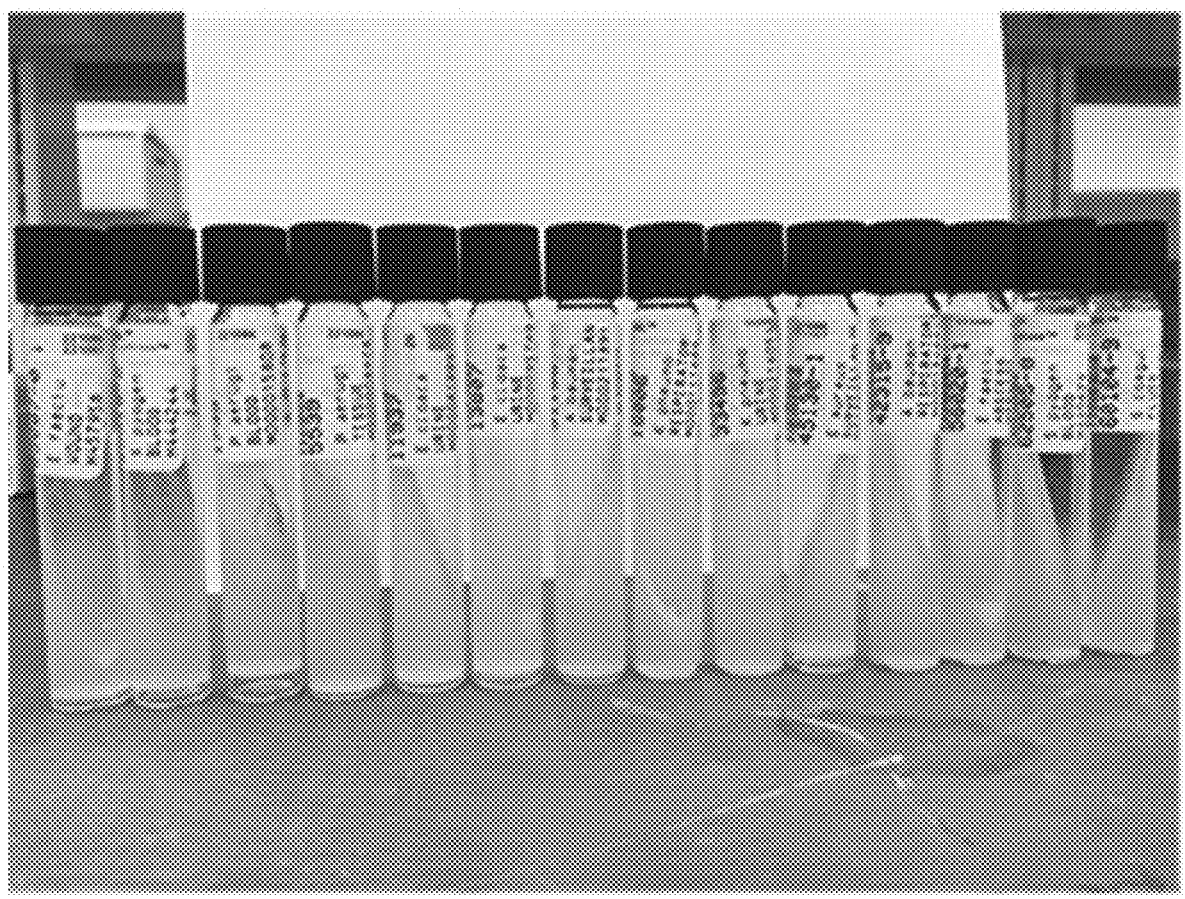
FIGS. 21A-21B show exemplary wound pathogens before and after contact with the hydrogel of the present application.

FIG. 21A shows vials of wound pathogen strains collected from patients' bodily fluids. The patients were soldiers in a field hospital, and the samples were received from Walter Reed Army Institute of Research & Naval Medical Research Center. Fourteen strains were collected, including P. aerugi, E. cloaca, A. bauman, K pneumo, S. aureus, S. coagul, E. faeciu, and S. pyogen. The fluids and tissues from which those strains were collected included blood, tissue, urine, surveillance, respirator, abscess, and wound. The various pathogens were contacted with various wound dressings, with the resulting growth shown on TSA plates.

Figure 21B:
Figure 21C:
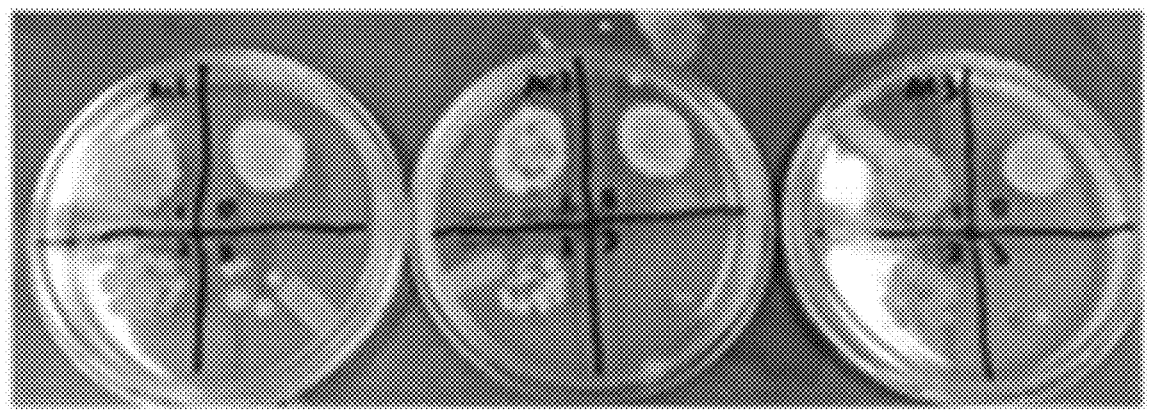
FIG. 21C shows in vitro samples of the wound pathogens of FIG. 21A after 30 minutes of contact time with three commercially available wound dressings.
Figure 21D:
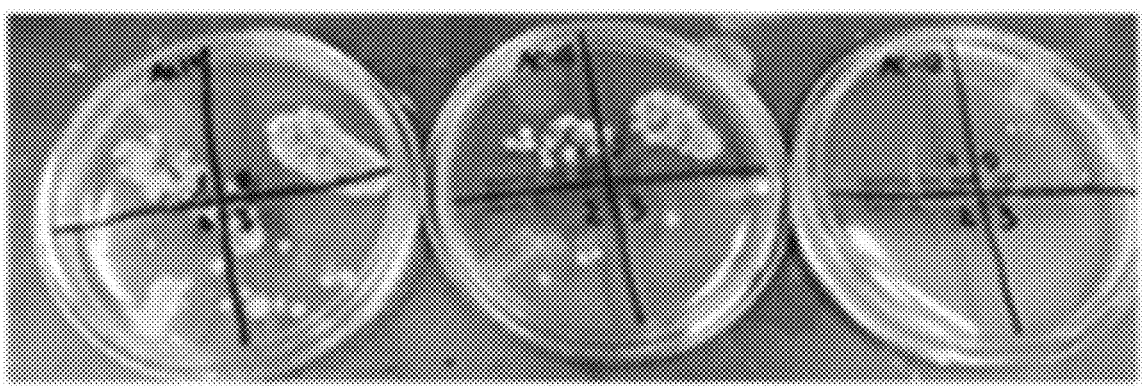
FIG. 21D shows in vitro samples of the wound pathogens of FIG. 21A after 5 minutes (left), 15 minutes (center), and 30 minutes (right) of contact time with a commercially available wound dressing.
Figure 21E:
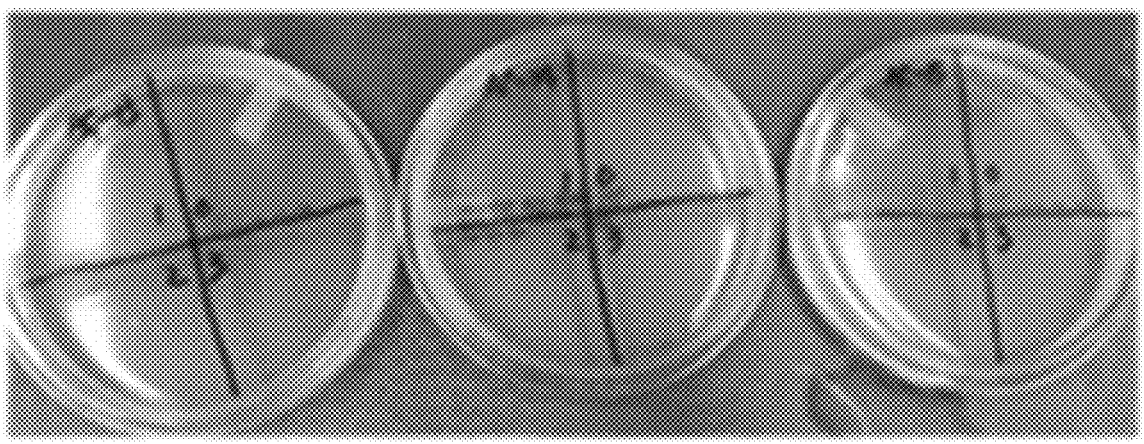
FIG. 21E shows in vitro samples of the wound pathogens of FIG. 21A after 5 minutes (left), 15 minutes (center), and 30 minutes (right) of contact time with a conformal hydrogel coating.

FIG. 21B shows a representative in vitro sample of the wound pathogens of FIG. 21A after 30 minutes of contact time with a wound dressing. FIG. 21C shows in vitro samples of the wound pathogens of FIG. 21A after 30 minutes of contact time with three commercially available wound dressings (from left to right: J&J uncoated gauze, CVS Honey Dressing, and DuoDerm Extra Thin Adhesive Dressing). FIG. 21D shows in vitro samples of the wound pathogens of FIG. 21A after 5 minutes (left), 15 minutes (center), and 30 minutes (right) of contact time with a CVS Silver Antibacterial commercially available wound dressing. FIG. 21E shows in vitro samples of the wound pathogens of FIG. 21A after 5 minutes (left), 15 minutes (center), and 30 minutes (right) of contact time with a conformal hydrogel coating. The conformal hydrogel coating comprising 40% SBMA, 6% HA, and 1.5% cross-linker (UV: 60 min (each side 30 min)) showed particularly favorable results.

Although preferred embodiments have been depicted and described in detail herein, it will be apparent to those skilled in the relevant art that various modifications, additions, substitutions, and the like can be made without departing from the spirit of the present application and these are therefore considered to be within the scope of the present application as defined in the claims which follow.

What is claimed:

1. A substrate having a conformal hydrogel coating prepared by the process of:
    applying an aqueous pre-hydrogel solution to a substrate, wherein the aqueous pre-hydrogel solution comprises a mixture of a monomer with antimicrobial activity, a monomer with antifouling activity, and a polymer selected from the group of agar, chitosan, an N-isopropylacrylamide copolymer, a poloxamer, a poly(ethylene oxide)/poly(lactic acid) block copolymer, poly(ethylene oxide)/poly(propylene oxide) block copolymers,

TABLE 3

Antimicrobial Efficacy Test Against Multiple Antibiotic-Resistant Microorganisms (Bacteria And Fungi).

| Tested samples | Contact time (min) | Survived bacterial number (Log CFU/sample) | | | | | |
|---|---|---|---|---|---|---|---|
| | | MRSA (5.83) | VRE (6.00) | E. coli (5.94) | Pseudomonas (5.68) | Klebsiella (5.98) | Candida (7.02) |
| J&J gauze | 30 | 4.63 | 5.75 | 5.08 | 4.98 | 4.98 | 6.25 |
| CVS ™ Honey | 30 | 5.08 | 5.64 | 5.20 | 3.33 | 3.33 | 5.68 |
| DuoDerm ™ Gel | 30 | 4.98 | 5.72 | 5.20 | 4.60 | 4.60 | 5.75 |
| CVS Silver | 5 | 4.08 | 4.75 | 3.60 | 3.51 | 3.83 | 5.45 |
| alginate | 15 | 3.83 | 3.68 | 3.56 | 3.98 | 3.56 | 5.11 |
| | 30 | 1.60 | 3.55 | 2.60 | 3.90 | 2.72 | 4.88 |
| Zwitterion- | 5 | 0 | 0 | 0 | 0 | 0 | 0 |
| halamine hydrogel | 15 | 0 | 0 | 0 | 0 | 0 | 0 |
| dressing | 30 | 0 | 0 | 0 | 0 | 0 | 0 |

| Abbreviation | Detailed description |
|---|---|
| MRSA | Methicillin-resistant Staphylococcus aureus MRSA USA300 wild type |
| VRE | Vancomycin-Resistant Enterococcus faecium ATCC BAA-2316 |
| Pseudomonas | Pseudomonas aeruginosa ATCC 15442 |
| E. coli | Escherichia coli ATCC 25922 |
| Klebsiella | Klebsiella pneumoniae ATCC 700721 |
| Candida | Candida albicans (Robin) Berkhout ATCC 90028 | alginate, dextran, and copolymers thereof, which mixture when polymerized together forms a hydrogel;
polymerizing the aqueous pre-hydrogel solution, thereby forming a coated substrate having a conformal hydrogel coating and a non-conformal hydrogel coating;
contacting the coated substrate with a swelling agent; and
removing the non-conformal hydrogel coating from the coated substrate, thereby leaving the conformal hydrogel coating on the substrate to form the hydrogel-coated substrate.

2. A coated substrate comprising:
a substrate; and
a conformal hydrogel coating on the substrate, wherein the conformal hydrogel coating comprises an antimicrobial agent, a zwitterionic antifouling agent, and a polymer,
wherein the antimicrobial agent, the zwitterionic antifouling agent, and the polymer are polymerized together, and
wherein the polymer is selected from the group of agar, chitosan, an N-isopropylacrylamide copolymer, a poloxamer, a poly(ethylene oxide)/poly(lactic acid) block copolymer, poly(ethylene oxide)/poly(propylene oxide) block copolymers, alginate, dextran, and copolymers thereof.

3. The coated substrate of claim 2, wherein the substrate is selected from the group consisting of silicone, latex, rubber, polyethylene, polyether ketone, polyurethane, polyester, a nylon polymer, a block copolymer of polyether and polyester polymers, a thermoplastic hydrocarbon polymer, copolymers thereof, and combinations thereof.

4. The coated substrate of claim 2, wherein the substrate is a catheter, a stent, a pump, a bandage, gauze, a suture, or an implantable device.

5. The coated substrate of claim 2, wherein the antimicrobial agent is selected from the group consisting of N-halamine, hydantoin acrylamide, 2,2,6,6-tetramethyl-4-piperidinyl methacrylate, N-halimides, N-halamides, and combinations thereof.

6. The coated substrate of claim 2, wherein the antifouling agent is a zwitterionic moiety selected from the group consisting of sulfobetaine, [2-methacryloyloxy)ethyl] dimethyl-(3-sulfopropyl) ammonia hydroxide, carboxybetaine methacrylate, methacryloyloxyethyl phosphorylcholine, serine methacrylate, lysine methacrylamide, ornithine methacrylamide, 3-[[2-(Methacryloyloxy)ethyl]-dimethylammonio]propane-1-sulfonate, 3-[[2-(Methacryloyloxy)ethyl] dimethylammonio]propionate, 3-[(3-Acrylamidopropyl) dimethylammonio]propanoate, sulfobetaine acrylate, sulfobetaine methacrylamide, sulfobetaine acrylamide, carboxybetaine acrylate, carboxybetaine acrylamide, carboxybetaine methacrylamide, serine acrylate, lysine acrylamide, ornithine acrylamide, and combinations thereof.

7. The coated substrate of claim 2, wherein the conformal hydrogel coating has a thickness from about 10 μm to about 200 μm.

8. The coated substrate according to claim 2, wherein the conformal coating further comprises a cross-linking agent that is polymerized with the antimicrobial agent, the zwitterionic antifouling agent, and the polymer.

9. The coated substrate according to claim 8, wherein the cross-linking agent is selected from the group of poly (ethylene glycol)dimethacrylate, tetramethylethylenediamine, carboxybetaine diacrylamide, carboxybetaine diacrylate, and combinations thereof.

10. The coated substrate according to claim 2, wherein the conformal hydrogel coating has a coefficient of friction that is lower than a coefficient of friction of the substrate.

11. The coated substrate according to claim 2, wherein the conformal hydrogel coating remains attached to the substrate when the coated substrate is mechanically stretched up to three times its original length.

12. A hydrogel coating comprising a N-halamine antimicrobial agent, a zwitterionic antifouling agent, and a polymer
wherein the antimicrobial agent, zwitterionic antifouling agent, and the polymer are polymerized together, and
wherein the polymer is selected from the group of agar, chitosan, an N-isopropylacrylamide copolymer, a poloxamer, a poly(ethylene oxide)/poly(lactic acid) block copolymer, poly(ethylene oxide)/poly(propylene oxide) block copolymers, alginate, dextran, and copolymers thereof.

13. The hydrogel coating according to claim 12 further comprising a cross-linking agent that is polymerized with the antimicrobial agent, the zwitterionic antifouling agent, and the polymer.

14. The hydrogel coating according to claim 13, wherein the cross-linking agent is selected from the group of poly (ethylene glycol)dimethacrylate, tetramethylethylenediamine, carboxybetaine diacrylamide, carboxybetaine diacrylate, and combinations thereof.

* * * * *